US011749412B2

(12) United States Patent
Florissi et al.

(10) Patent No.: US 11,749,412 B2
(45) Date of Patent: *Sep. 5, 2023

(54) DISTRIBUTED DATA ANALYTICS

(71) Applicant: EMC IP Holding Company LLC, Hopkinton, MA (US)

(72) Inventors: Patricia Gomes Soares Florissi, Briarcliff Manor, NY (US); Michal Ziv Ukelson, Lehavim (IL); Ran Dach, Kiryat Yam (IL); Arnon Benshahar, Tel Aviv (IL); Ehud Gudes, Beer-Sheva (IL)

(73) Assignee: EMC IP Holding Company LLC, Hopkinton, MA (US)

( * ) Notice: Subject to any disclaimer, the term of this patent is extended or adjusted under 35 U.S.C. 154(b) by 623 days.

This patent is subject to a terminal disclaimer.

(21) Appl. No.: 16/921,303

(22) Filed: Jul. 6, 2020

(65) Prior Publication Data

US 2020/0335223 A1    Oct. 22, 2020

Related U.S. Application Data

(63) Continuation of application No. 15/719,231, filed on Sep. 28, 2017, now Pat. No. 10,706,970, which is a
(Continued)

(51) Int. Cl.
*G01N 33/48* (2006.01)
*G01N 33/50* (2006.01)
(Continued)

(52) U.S. Cl.
CPC .......... *G16H 50/70* (2018.01); *G06F 16/182* (2019.01); *G06F 16/436* (2019.01); *G16H 50/20* (2018.01); *G06Q 50/22* (2013.01)

(58) Field of Classification Search
CPC ...... G16H 50/70; G16H 50/20; G06F 16/182; G06F 16/436; G06Q 50/22
See application file for complete search history.

(56) References Cited

U.S. PATENT DOCUMENTS 5,813,009 A    9/1998  Johnson et al.
6,112,225 A    8/2000  Kraft et al.
(Continued)

FOREIGN PATENT DOCUMENTS

CN    104731595 A      6/2015
WO    2012103189 A1    8/2012

OTHER PUBLICATIONS

I. Z. Kiss et al., "Disease Contact Tracing In Random and Clustered Networks," Proceedings of The Royal Society B, Biological Sciences, Jun. 21, 2005, pp. 1407-1414.
(Continued)

*Primary Examiner* — Russell S Negin
(74) *Attorney, Agent, or Firm* — Ryan, Mason & Lewis, LLP

(57) ABSTRACT

An apparatus in one embodiment comprises a distributed data processing system in which multiple processing devices communicate with one another over at least one network. The distributed data processing system is configured to obtain reads of biological samples of respective sample sources, with each of the biological samples containing genomic material from a plurality of distinct microorganisms within an environment of a corresponding one of the sample sources, and to perform distributed data analytics to characterize an actual or potential outbreak of at least one of a disease, an infection and a contamination that involves genomic material from multiple ones of the distinct microorganisms in one or more of the sample sources. Performing distributed data analytics illustratively comprises performing local analytics in respective ones of a plurality of data
(Continued)

zones, and performing global analytics utilizing results of the local analytics performed in the respective data zones.

20 Claims, 62 Drawing Sheets

Related U.S. Application Data continuation-in-part of application No. 15/281,248, filed on Sep. 30, 2016, now Pat. No. 10,528,875, said application No. 15/281,248 is a continuation-in-part of application No. 14/983,932, filed on Dec. 30, 2015, now Pat. No. 10,311,363.

(60) Provisional application No. 62/400,767, filed on Sep. 28, 2016, provisional application No. 62/143,685, filed on Apr. 6, 2015, provisional application No. 62/143,404, filed on Apr. 6, 2015.

(51) Int. Cl.
| | |
|---|---|
| *G16H 50/70* | (2018.01) |
| *G16H 50/20* | (2018.01) |
| *G06F 16/182* | (2019.01) |
| *G06F 16/435* | (2019.01) |
| *G06Q 50/22* | (2018.01) |

(56) References Cited

U.S. PATENT DOCUMENTS

| | | |
|---|---|---|
| 6,154,742 A | 11/2000 | Herriot |
| 6,385,652 B1 | 5/2002 | Brown et al. |
| 6,516,350 B1 | 2/2003 | Lumelsky et al. |
| 6,879,729 B2 | 4/2005 | Kamath et al. |
| 7,010,163 B1 | 3/2006 | Weiss |
| 7,499,915 B2 | 3/2009 | Chandrasekar et al. |
| 7,657,537 B1 | 2/2010 | Corbett |
| 7,904,909 B1 | 3/2011 | Reiner et al. |
| 7,934,018 B1 | 4/2011 | Lavallee et al. |
| 7,934,248 B1 | 4/2011 | Yehuda et al. |
| 7,953,843 B2 | 5/2011 | Cherkasova |
| 8,224,825 B2 | 7/2012 | Wang et al. |
| 8,392,564 B1 | 3/2013 | Czajkowski et al. |
| 8,499,331 B1 | 7/2013 | Yehuda et al. |
| 8,706,798 B1 | 4/2014 | Suchter et al. |
| 8,732,118 B1 | 5/2014 | Cole et al. |
| 8,806,061 B1 | 8/2014 | Lobo et al. |
| 8,873,836 B1 | 10/2014 | Dietrich et al. |
| 8,886,649 B2 | 11/2014 | Zhang et al. |
| 8,904,506 B1 | 12/2014 | Canavor et al. |
| 8,938,416 B1 | 1/2015 | Cole et al. |
| 9,020,802 B1 | 4/2015 | Florissi et al. |
| 9,031,992 B1 | 5/2015 | Florissi et al. |
| 9,130,832 B1 | 9/2015 | Boe et al. |
| 9,158,843 B1 | 10/2015 | Florissi et al. |
| 9,229,952 B1 | 1/2016 | Meacham et al. |
| 9,235,446 B2 | 1/2016 | Bruno et al. |
| 9,239,711 B1 | 1/2016 | Mistry |
| 9,280,381 B1 | 3/2016 | Florissi et al. |
| 9,298,613 B2 | 3/2016 | Kim et al. |
| 9,338,218 B1 | 5/2016 | Florissi et al. |
| 9,361,263 B1 | 6/2016 | Florissi et al. |
| 9,374,660 B1 | 6/2016 | Tilles |
| 9,418,085 B1 | 8/2016 | Shih et al. |
| 9,451,012 B1 | 9/2016 | Neill et al. |
| 9,489,233 B1 | 11/2016 | Florissi et al. |
| 9,538,332 B1 | 1/2017 | Mendelson |
| 9,613,124 B2 | 4/2017 | Rabinowitz et al. |
| 9,659,057 B2 | 5/2017 | Tian |
| 9,665,660 B2 | 5/2017 | Wensel |
| 9,678,497 B2 | 6/2017 | Karypis et al. |
| 9,697,262 B2 | 7/2017 | Chandramouli et al. |
| 9,747,127 B1 | 8/2017 | Florissi et al. |
| 9,747,128 B1 | 8/2017 | Vijendra et al. |
| 9,767,149 B2 | 9/2017 | Ozcan et al. |
| 9,805,170 B2 | 10/2017 | Keyes et al. |
| 9,832,068 B2 | 11/2017 | McSherry et al. |
| 9,838,410 B2 | 12/2017 | Muddu et al. |
| 9,848,041 B2 | 12/2017 | Einkauf et al. |
| 9,922,334 B1 | 3/2018 | Rothman |
| 9,996,662 B1 | 6/2018 | Florissi et al. |
| 10,015,106 B1 | 7/2018 | Florissi et al. |
| 10,114,923 B1 | 10/2018 | Florissi et al. |
| 10,122,806 B1 | 11/2018 | Florissi et al. |
| 10,127,352 B1 | 11/2018 | Florissi et al. |
| 10,148,736 B1 | 12/2018 | Lee et al. |
| 10,250,708 B1 | 4/2019 | Carver et al. |
| 10,270,707 B1 | 4/2019 | Florissi et al. |
| 10,277,668 B1 | 4/2019 | Florissi |
| 10,311,363 B1 | 6/2019 | Florissi et al. |
| 10,331,380 B1 | 6/2019 | Florissi et al. |
| 10,348,810 B1 | 7/2019 | Florissi et al. |
| 10,366,111 B1 | 7/2019 | Florissi et al. |
| 10,374,968 B1 | 8/2019 | Duerk et al. |
| 10,404,787 B1 | 9/2019 | Florissi et al. |
| 10,425,350 B1 | 9/2019 | Florissi |
| 10,496,926 B2 | 12/2019 | Florissi et al. |
| 10,505,863 B1 | 12/2019 | Florissi et al. |
| 10,509,684 B2 | 12/2019 | Florissi et al. |
| 10,511,659 B1 | 12/2019 | Florissi et al. |
| 10,515,097 B2 | 12/2019 | Florissi et al. |
| 10,528,875 B1 | 1/2020 | Florissi et al. |
| 10,541,936 B1 | 1/2020 | Florissi |
| 10,541,938 B1 | 1/2020 | Timmerman et al. |
| 10,656,861 B1 | 5/2020 | Florissi et al. |
| 10,664,856 B2 | 5/2020 | Robbin et al. |
| 10,706,970 B1 | 7/2020 | Florissi et al. |
| 10,776,404 B2 | 9/2020 | Florissi et al. |
| 10,791,063 B1 | 9/2020 | Florissi et al. |
| 10,812,341 B1 | 10/2020 | Campello De Souza et al. |
| 10,860,622 B1 | 12/2020 | Florissi |
| 10,944,688 B2 | 3/2021 | Florissi |
| 10,984,889 B1 | 4/2021 | Florissi et al. |
| 10,986,168 B2 | 4/2021 | Florissi et al. |
| 10,999,353 B2 | 5/2021 | Florissi |
| 2002/0056025 A1 | 5/2002 | Qiu et al. |
| 2002/0073167 A1 | 6/2002 | Powell et al. |
| 2002/0087576 A1 | 7/2002 | Geiger et al. |
| 2002/0129123 A1 | 9/2002 | Johnson et al. |
| 2003/0005140 A1 | 1/2003 | Dekel et al. |
| 2003/0212741 A1 | 11/2003 | Glasco |
| 2004/0025058 A1 | 2/2004 | Kuriya et al. |
| 2004/0060032 A1 | 3/2004 | McCubbrey |
| 2004/0247198 A1 | 12/2004 | Ghosh et al. |
| 2005/0010712 A1 | 1/2005 | Kim et al. |
| 2005/0076291 A1 | 4/2005 | Yee et al. |
| 2005/0102354 A1 | 5/2005 | Hollenbeck et al. |
| 2005/0114476 A1 | 5/2005 | Chen et al. |
| 2005/0132297 A1 | 6/2005 | Milic-Frayling et al. |
| 2005/0153686 A1 | 7/2005 | Kall et al. |
| 2005/0165925 A1 | 7/2005 | Dan et al. |
| 2005/0257400 A1 | 11/2005 | Sommerer et al. |
| 2005/0266420 A1 | 12/2005 | Pusztai et al. |
| 2005/0278761 A1 | 12/2005 | Gonder et al. |
| 2006/0002383 A1 | 1/2006 | Jeong et al. |
| 2006/0074967 A1 | 4/2006 | Shaburov |
| 2006/0112244 A1 | 5/2006 | Buah et al. |
| 2006/0122927 A1 | 6/2006 | Huberman et al. |
| 2006/0126865 A1 | 6/2006 | Blamey et al. |
| 2006/0173628 A1 | 8/2006 | Sampas et al. |
| 2007/0026426 A1 | 2/2007 | Fuernkranz et al. |
| 2007/0076703 A1 | 4/2007 | Yoneda et al. |
| 2007/0088703 A1 | 4/2007 | Kasiolas et al. |
| 2007/0174541 A1 | 7/2007 | Chandrasekaran et al. |
| 2007/0179753 A1 | 8/2007 | Barajas et al. |
| 2007/0209002 A1 | 9/2007 | Terada et al. |
| 2008/0027954 A1 | 1/2008 | Gan et al. |
| 2008/0028086 A1 | 1/2008 | Chetuparambil et al. |
| 2008/0077607 A1 | 3/2008 | Gatawood et al. |
| 2008/0155100 A1 | 6/2008 | Ahmed et al. |
| 2008/0184245 A1 | 7/2008 | St-Jean |
| 2008/0260119 A1 | 10/2008 | Marathe et al. |
| 2008/0279167 A1 | 11/2008 | Cardei et al. |

(56) References Cited

U.S. PATENT DOCUMENTS

| | | |
|---|---|---|
| 2009/0062623 A1 | 3/2009 | Cohen et al. |
| 2009/0070404 A1 | 3/2009 | Mazzaferri |
| 2009/0076851 A1 | 3/2009 | Rao |
| 2009/0150084 A1 | 6/2009 | Colwell et al. |
| 2009/0198389 A1 | 8/2009 | Kirchhof-Falter et al. |
| 2009/0310485 A1 | 12/2009 | Averi et al. |
| 2009/0319188 A1 | 12/2009 | Otto |
| 2010/0005077 A1 | 1/2010 | Krishnamurthy et al. |
| 2010/0042809 A1 | 2/2010 | Schenfeld et al. |
| 2010/0057563 A1 | 3/2010 | Rauber et al. |
| 2010/0076845 A1 | 3/2010 | Ramer et al. |
| 2010/0076856 A1 | 3/2010 | Mullins |
| 2010/0122065 A1 | 5/2010 | Dean et al. |
| 2010/0131639 A1 | 5/2010 | Narayana et al. |
| 2010/0131700 A1 | 5/2010 | Castillo |
| 2010/0153915 A1 | 6/2010 | Schneider |
| 2010/0184093 A1 | 7/2010 | Donovan et al. |
| 2010/0229178 A1 | 9/2010 | Ito |
| 2010/0241714 A1 | 9/2010 | Aono et al. |
| 2010/0250646 A1 | 9/2010 | Dunagan et al. |
| 2010/0290468 A1 | 11/2010 | Lynam et al. |
| 2010/0293334 A1 | 11/2010 | Xun et al. |
| 2010/0299437 A1 | 11/2010 | Moore |
| 2011/0020785 A1 | 1/2011 | Lowery, Jr. et al. |
| 2011/0029999 A1 | 2/2011 | Foti |
| 2011/0103364 A1 | 5/2011 | Li |
| 2011/0144932 A1 | 6/2011 | Alles |
| 2011/0145828 A1 | 6/2011 | Takahashi et al. |
| 2011/0208703 A1 | 8/2011 | Fisher et al. |
| 2011/0314002 A1 | 12/2011 | Oliver et al. |
| 2012/0030599 A1 | 2/2012 | Butt et al. |
| 2012/0047266 A1 | 2/2012 | Minert |
| 2012/0059707 A1 | 3/2012 | Goenka et al. |
| 2012/0071774 A1 | 3/2012 | Osorio et al. |
| 2012/0102409 A1 | 4/2012 | Fan et al. |
| 2012/0182891 A1 | 7/2012 | Lee et al. |
| 2012/0191699 A1 | 7/2012 | George et al. |
| 2012/0198020 A1 | 8/2012 | Parker et al. |
| 2012/0209526 A1 | 8/2012 | Imhof |
| 2012/0215555 A1 | 8/2012 | Sharma et al. |
| 2012/0215562 A1 | 8/2012 | James et al. |
| 2012/0215919 A1 | 8/2012 | Labat et al. |
| 2013/0035956 A1 | 2/2013 | Carmeli et al. |
| 2013/0044925 A1 | 2/2013 | Kozuka et al. |
| 2013/0054670 A1 | 2/2013 | Keyes et al. |
| 2013/0117321 A1 | 5/2013 | Fischer et al. |
| 2013/0194928 A1 | 8/2013 | Iqbal |
| 2013/0246460 A1 | 9/2013 | Maltbie et al. |
| 2013/0252631 A1 | 9/2013 | Alizadeh-Shabdiz et al. |
| 2013/0282897 A1 | 10/2013 | Siegel et al. |
| 2013/0290249 A1 | 10/2013 | Merriman et al. |
| 2013/0291118 A1 | 10/2013 | Li et al. |
| 2013/0318257 A1 | 11/2013 | Lee et al. |
| 2013/0326538 A1 | 12/2013 | Gupta et al. |
| 2013/0346229 A1 | 12/2013 | Martin et al. |
| 2013/0346543 A1 | 12/2013 | Benantar et al. |
| 2013/0346988 A1 | 12/2013 | Bruno et al. |
| 2014/0012843 A1 | 1/2014 | Soon-Shiong |
| 2014/0025393 A1 | 1/2014 | Wang et al. |
| 2014/0032240 A1 | 1/2014 | Lougheed et al. |
| 2014/0032518 A1 | 1/2014 | Cohen et al. |
| 2014/0047048 A1 | 2/2014 | Ail et al. |
| 2014/0075161 A1 | 3/2014 | Zhang et al. |
| 2014/0081984 A1 | 3/2014 | Sitsky et al. |
| 2014/0082178 A1 | 3/2014 | Boldyrev et al. |
| 2014/0143251 A1 | 5/2014 | Wang et al. |
| 2014/0173331 A1 | 6/2014 | Martin et al. |
| 2014/0173618 A1 | 6/2014 | Neuman et al. |
| 2014/0181176 A1 | 6/2014 | Swamy et al. |
| 2014/0188596 A1 | 7/2014 | Nangle, III |
| 2014/0201153 A1 | 7/2014 | Vijayan et al. |
| 2014/0214752 A1 | 7/2014 | Rash et al. |
| 2014/0215007 A1 | 7/2014 | Rash et al. |
| 2014/0278808 A1 | 9/2014 | Iyoob et al. |
| 2014/0279201 A1 | 9/2014 | Iyoob et al. |
| 2014/0280298 A1 | 9/2014 | Petride et al. |
| 2014/0280363 A1 | 9/2014 | Heng et al. |
| 2014/0280604 A1 | 9/2014 | Ahiska et al. |
| 2014/0280695 A1 | 9/2014 | Sharma et al. |
| 2014/0280880 A1 | 9/2014 | Tellis et al. |
| 2014/0280990 A1 | 9/2014 | Dove et al. |
| 2014/0310258 A1 | 10/2014 | Tian |
| 2014/0310718 A1 | 10/2014 | Gerphagnon et al. |
| 2014/0320497 A1 | 10/2014 | Vojnovic et al. |
| 2014/0324647 A1 | 10/2014 | Iyoob et al. |
| 2014/0325041 A1 | 10/2014 | Xu et al. |
| 2014/0333638 A1 | 11/2014 | Kaminski et al. |
| 2014/0337061 A1 | 11/2014 | Olson et al. |
| 2014/0344340 A1 | 11/2014 | Tang et al. |
| 2014/0358999 A1 | 12/2014 | Rabinowitz et al. |
| 2014/0365518 A1 | 12/2014 | Calo et al. |
| 2014/0365662 A1 | 12/2014 | Dave et al. |
| 2014/0372611 A1 | 12/2014 | Matsuda et al. |
| 2014/0379722 A1 | 12/2014 | Mysur et al. |
| 2015/0006619 A1 | 1/2015 | Banadaki et al. |
| 2015/0012657 A1 | 1/2015 | Botti et al. |
| 2015/0019710 A1 | 1/2015 | Shaashua et al. |
| 2015/0039586 A1 | 2/2015 | Kerschbaum et al. |
| 2015/0039667 A1 | 2/2015 | Shah et al. |
| 2015/0058843 A1 | 2/2015 | Holler et al. |
| 2015/0066646 A1 | 3/2015 | Sriharsha et al. |
| 2015/0081877 A1 | 3/2015 | Sethi et al. |
| 2015/0088786 A1 | 3/2015 | Anandhakrishnan |
| 2015/0092561 A1 | 4/2015 | Sigoure |
| 2015/0120791 A1 | 4/2015 | Gummaraju et al. |
| 2015/0121371 A1 | 4/2015 | Gummaraju et al. |
| 2015/0127769 A1 | 5/2015 | Word |
| 2015/0169683 A1 | 6/2015 | Chandramouli et al. |
| 2015/0170616 A1 | 6/2015 | Corpet et al. |
| 2015/0178052 A1 | 6/2015 | Gupta et al. |
| 2015/0193583 A1 | 7/2015 | McNair et al. |
| 2015/0201036 A1 | 7/2015 | Nishiki et al. |
| 2015/0222723 A1 | 8/2015 | Adapalli et al. |
| 2015/0249618 A1 | 9/2015 | Golander |
| 2015/0254344 A1 | 9/2015 | Kulkarni et al. |
| 2015/0254558 A1 | 9/2015 | Arnold et al. |
| 2015/0262268 A1 | 9/2015 | Padmanabhan et al. |
| 2015/0264122 A1 | 9/2015 | Shau et al. |
| 2015/0269230 A1 | 9/2015 | Kardes et al. |
| 2015/0277791 A1 | 10/2015 | Li et al. |
| 2015/0278513 A1 | 10/2015 | Krasin et al. |
| 2015/0294256 A1 | 10/2015 | Mahesh et al. |
| 2015/0295781 A1 | 10/2015 | Maes |
| 2015/0302075 A1 | 10/2015 | Schechter et al. |
| 2015/0319144 A1 | 11/2015 | Barton et al. |
| 2015/0326644 A1 | 11/2015 | Yahalom et al. |
| 2015/0334548 A1 | 11/2015 | Liu et al. |
| 2015/0339210 A1 | 11/2015 | Kopp et al. |
| 2015/0355946 A1 | 12/2015 | Kang |
| 2015/0369618 A1 | 12/2015 | Barnard et al. |
| 2015/0381709 A1 | 12/2015 | Word |
| 2016/0004827 A1 | 1/2016 | Silva et al. |
| 2016/0006628 A1 | 1/2016 | Herring et al. |
| 2016/0020967 A1 | 1/2016 | Thubert et al. |
| 2016/0034828 A1 | 2/2016 | Sarawgi et al. |
| 2016/0063191 A1 | 3/2016 | Vesto et al. |
| 2016/0072726 A1 | 3/2016 | Soni et al. |
| 2016/0087909 A1 | 3/2016 | Chatterjee et al. |
| 2016/0088023 A1 | 3/2016 | Handa et al. |
| 2016/0098021 A1 | 4/2016 | Zornio et al. |
| 2016/0098472 A1 | 4/2016 | Appleton |
| 2016/0098662 A1 | 4/2016 | Voss et al. |
| 2016/0103433 A1 | 4/2016 | Sahni et al. |
| 2016/0112531 A1 | 4/2016 | Milton et al. |
| 2016/0117373 A1 | 4/2016 | Dang et al. |
| 2016/0123941 A1 | 5/2016 | Bowers et al. |
| 2016/0125056 A1 | 5/2016 | Knezevic et al. |
| 2016/0132576 A1 | 5/2016 | Qi et al. |
| 2016/0142326 A1 | 5/2016 | Akiyoshi |
| 2016/0170882 A1 | 6/2016 | Choi et al. |
| 2016/0171072 A1 | 6/2016 | Jagtiani et al. |
| 2016/0179642 A1 | 6/2016 | Cai |
| 2016/0179979 A1 | 6/2016 | Aasman et al. |
| 2016/0182305 A1 | 6/2016 | Martin et al. |

(56) References Cited

U.S. PATENT DOCUMENTS

| | | |
|---|---|---|
| 2016/0182327 A1 | 6/2016 | Coleman, Jr. et al. |
| 2016/0183313 A1 | 6/2016 | Vallabhu et al. |
| 2016/0188594 A1 | 6/2016 | Ranganathan |
| 2016/0196324 A1 | 7/2016 | Haviv et al. |
| 2016/0205106 A1 | 7/2016 | Yacoub et al. |
| 2016/0241893 A1 | 8/2016 | Allhands et al. |
| 2016/0246981 A1 | 8/2016 | Nakagawa et al. |
| 2016/0254941 A1 | 9/2016 | Liu et al. |
| 2016/0260023 A1 | 9/2016 | Miserendino, Jr. et al. |
| 2016/0261727 A1 | 9/2016 | Yang et al. |
| 2016/0267132 A1 | 9/2016 | Castellanos et al. |
| 2016/0269228 A1 | 9/2016 | Franke et al. |
| 2016/0274978 A1 | 9/2016 | Strohmenger et al. |
| 2016/0283551 A1 | 9/2016 | Fokoue-Nkoutche et al. |
| 2016/0323377 A1 | 11/2016 | Einkauf et al. |
| 2016/0328661 A1 | 11/2016 | Reese et al. |
| 2016/0337473 A1 | 11/2016 | Rao |
| 2016/0350157 A1 | 12/2016 | Necas |
| 2017/0006135 A1 | 1/2017 | Siebel et al. |
| 2017/0032263 A1 | 2/2017 | Yuan et al. |
| 2017/0053008 A1 | 2/2017 | Frenkel et al. |
| 2017/0083573 A1 | 3/2017 | Rogers et al. |
| 2017/0109299 A1 | 4/2017 | Belair et al. |
| 2017/0116289 A1 | 4/2017 | Deshmukh et al. |
| 2017/0149630 A1 | 5/2017 | Feller et al. |
| 2017/0155707 A1 | 6/2017 | Rash et al. |
| 2017/0187785 A1 | 6/2017 | Johnson et al. |
| 2017/0220646 A1 | 8/2017 | Schechter et al. |
| 2017/0272458 A1 | 9/2017 | Muddu et al. |
| 2017/0323028 A1 | 11/2017 | Jonker et al. |
| 2017/0337135 A1 | 11/2017 | Hu et al. |
| 2017/0346690 A1 | 11/2017 | Dorado et al. |
| 2018/0054355 A1 | 2/2018 | Balser et al. |
| 2018/0101583 A1 | 4/2018 | Li et al. |
| 2018/0109934 A1 | 4/2018 | Grube |
| 2018/0181957 A1 | 6/2018 | Crabtree et al. |
| 2018/0189296 A1 | 7/2018 | Ashour et al. |
| 2018/0232262 A1 | 8/2018 | Chowdhury et al. |
| 2018/0240062 A1 | 8/2018 | Crabtree et al. |
| 2018/0308585 A1 | 10/2018 | Holmes et al. |
| 2019/0018965 A1 | 1/2019 | Hoscheit et al. |
| 2019/0026146 A1 | 1/2019 | Peffers et al. |
| 2019/0130122 A1 | 5/2019 | Barnes et al. |
| 2019/0149418 A1 | 5/2019 | Bertsche et al. |
| 2019/0149479 A1 | 5/2019 | Florissi et al. |
| 2019/0173666 A1 | 6/2019 | Ardashev et al. |
| 2019/0176335 A1 | 6/2019 | Shivaram et al. |
| 2019/0179672 A1 | 6/2019 | Christidis et al. |
| 2019/0206090 A1 | 7/2019 | Ray et al. |
| 2019/0207759 A1 | 7/2019 | Chan et al. |
| 2019/0208004 A1 | 7/2019 | Florissi |
| 2019/0214848 A1 | 7/2019 | Waffner |
| 2019/0244243 A1 | 8/2019 | Goldberg et al. |
| 2019/0253134 A1 | 8/2019 | Coleman et al. |
| 2019/0361845 A1 | 11/2019 | Faith et al. |
| 2019/0363995 A1 | 11/2019 | Florissi |

OTHER PUBLICATIONS

C. Seibold et al., "Modeling Epidemics On A Regular Tree Graph," Letters In Biomathematics, 2016, vol. 3, No. 1, pp. 59-74.
G. Pavlopoulos et al., "Using Graph Theory To Analyze Biological Networks," BioData Mining, Apr. 2011, 27 pages.
M. J. Keeling et al., "Networks and Epidemic Models," J.R. Soc. Interface, Jun. 2005, pp. 295-307.
V.K. Vavilapalli et al., "Apache Hadoop YARN: Yet Another Resource Negotiator," Proceedings of the 4th Annual Symposium on Cloud Computing (SOCC), Article No. 5, Oct. 2013, 16 pages.
A.C. Murthy et al., "Apache Hadoop YARN: Moving beyond MapReduce and Batch Processing with Apache Hadoop 2," Addison-Wesley Professional, Mar. 29, 2014, 78 pages.
Global Alliance for Genomics and Health, "Beacons," https://genomicsandhealth.org/work-products-demonstration-projects/beacons, Jun. 27, 2014, 2 pages.
Data Working Group, "Global Alliance Genomics API," http://ga4gh.org/#documentation, Dec. 28, 2015, 2 pages.
Aaron Krol, "Beacon Project Cracks the Door for Genomic Data Sharing," http://www.bio-itworld.com/2015/8/14/beacon-project-cracks-door-genomic-data-sharing.html, Aug. 14, 2015, 3 pages.
Wikipedia, "Apache Spark," https://en.wikipedia.org/wiki/Apache_Spark, Apr. 10, 2017, 6 pages.
M.K. Gardner et al., "Parallel Genomic Sequence-Searching On An Ad-Hoc Grid: Experiences, Lessons Learned, and Implications," Proceedings of the 2006 ACM/IEEE SC/06 Conference, IEEE Computer Society, 2006, 14 pages.
A.G. Craig et al., "Ordering of Cosmid Clones Covering the Herpes Simplex Virus Type I (HSV-I) Genome: A Test Case For Fingerprinting By Hybridisation," Nucleic Acids Research, vol. 18, 1990, pp. 2653-2660.
T.R. Golub et al., "Molecular classification of Cancer: Class Discovery and Class Prediction By Gene Expression Monitoring," Science, vol. 286, Oct. 15, 1999, pp. 531-537.
D. Singh et al., "Gene Expression Correlates of Clinical Prostate Cancer Behavior," Cancer Cell, vol. 1, Mar. 2002, pp. 203-209.
P.P. Jayaraman et al., "Analytics-as-a-Service in a Multi-Cloud Environment Through Semantically-Enabled Hierarchical Data Processing," Software: Practice and Experience, Aug. 2017, pp. 1139-1156, vol. 47, No. 8.
J.Y.L. Lee et al., "Sufficiency Revisited: Rethinking Statistical Algorithms in the Big Data Era," The American Statistician, Dec. 15, 2016, 22 pages.
S. Wang et al., "Genome Privacy: Challenges, Technical Approaches to Mitigate Risk, and Ethical Considerations in the United States," Annals of the New York Academy of Sciences, Jan. 2017, pp. 73-83, vol. 1387, No. 1.
K. Xu et al., "Privacy-Preserving Machine Learning Algorithms for Big Data Systems," IEEE 35th International Conference on Distributed Computing Systems (ICDCS), Jun. 29-Jul. 2, 2015, pp. 318-327.
Dell, "Dell Boomi Platform: Connect Every Part of Your Business to Transform How You do Business," https://marketing.boomi.com/rs/777-AVU-348/images/Boomi-Integration-Cloud.pdf, 2017, 4 pages.
X. Wu et al., "Privacy Preserving Data Mining Research: Current Status and Key Issues," Proceedings of the 7th International Conference on Computational Science, Part III: ICCS 2007, May 2007, pp. 762-772.
A.P. Kulkarni et al., "Survey on Hadoop and Introduction to YARN," International Journal of Emerging Technology and Advanced Engineering, May 2014, pp. 82-87, vol. 4, No. 5.
R.R. Miller et al., "Metagenomics for Pathogen Detection in Public Health," Genome Medicine, Sep. 20, 2013, 14 pages, vol. 5, No. 81.
T. Thomas et al., "Metagenomics—A Guide from Sampling to Data Analysis," Microbial Informatics and Experimentation, Oct. 13, 2012, 12 pages, vol. 2, No. 3.
E.R. Ganser et al., "A Technique for Drawing Directed Graphs," IEEE Transactions on Software Engineering, Mar. 1993, pp. 214-230, vol. 19, No. 3.
J. Leskovec, "Graphs Over Time: Densification Laws, Shrinking Diameters and Possible Explanations," Proceedings of the Eleventh ACM SIGKDD International Conference on Knowledge Discovery in Data Mining, Aug. 21-24, 2005, pp. 177-187.
H. Zha et al., "Bipartite Graph Partitioning and Data Clustering," Proceedings of the Tenth International Conference on Information and Knowledge Management, Oct. 5-10, 2001, pp. 25-32.
A. Oghabian et al., "Biclustering Methods: Biological Relevance and Application in Gene Expression Analysis," PLOS One, Mar. 20, 2014, 10 pages, vol. 9, No. 3.
S. Ryza, "How To: Tune Your Apache Spark Jobs," https://blog.cloudera.com/blog/2015/03/how-to-tune-your-apache-spark-jobs-part-1/, Mar. 9, 2015, 23 pages.
T. White, "Hadoop: The Definitive Guide," O'Reilly Media, Inc., Fourth Edition, Sebastopol, CA, Apr. 2015, 756 pages.
L. Shashank, "Spark On Yarn," https://www.slideshare.net/datamantra/spark-on-yarn-54201193, Oct. 21, 2015, 47 pages.
D. Ucar et al., "Combinatorial Chromatin Modification Patterns in the Human Genome Revealed by Subspace Clustering," Nucleic Acids Research, May 1, 2011, pp. 4063-4075, vol. 39, No. 10.

(56) References Cited

OTHER PUBLICATIONS

S. Wohl et al., "Genomic Analysis of Virtual Breaks," Author Manuscript, HHS Public Access, Jan. 2017, 29 pages.

DISTRIBUTED DATA ANALYTICS

RELATED APPLICATIONS

The present application is a continuation of U.S. patent application Ser. No. 15/719,231, filed Sep. 28, 2017 and entitled "Distributed Data Analytics," which is incorporated by reference herein in its entirety, and which is a continuation-in-part of U.S. patent application Ser. No. 15/281,248, filed Sep. 30, 2016, now U.S. Pat. No. 10,528,875, and entitled "Methods and Apparatus Implementing Data Model for Disease Monitoring, Characterization and Investigation," which is incorporated by reference herein in its entirety, and which is a continuation-in-part of U.S. patent application Ser. No. 14/983,932, filed Dec. 30, 2015, now U.S. Pat. No. 10,311,363, and entitled "Reasoning on Data Model for Disease Monitoring, Characterization and Investigation," which is incorporated by reference herein in its entirety, and which claims priority to U.S. Provisional Patent Application Ser. No. 62/143,404, entitled "World Wide Hadoop Platform," and U.S. Provisional Patent Application Ser. No. 62/143,685, entitled "Bioinformatics," both filed Apr. 6, 2015, and incorporated by reference herein in their entirety. U.S. patent application Ser. No. 15/719,231 also claims priority to U.S. Provisional Application Ser. No. 62/400,767, filed Sep. 28, 2016 and entitled "Data Analytics," which is incorporated by reference herein in its entirety.

The present application is also related to the following additional U.S. patent applications, each of which is incorporated by reference herein in its entirety:

Ser. No. 14/983,914, filed Dec. 30, 2015, now U.S. Pat. No. 10,114,923, and entitled "Metagenomics-Based Biological Surveillance System using Big Data Profiles,"

Ser. No. 14/983,920, filed Dec. 30, 2015 and entitled "Automated Metagenomic Epidemiological Investigation,"

Ser. No. 14/983,943, filed Dec. 30, 2015 and entitled "Distributed Data Processing Platform for Metagenomic Epidemiological Investigation,"

Ser. No. 14/983,952, filed Dec. 30, 2015 and entitled "Distributed Data Processing Platform for Biological Surveillance using Big Data Profiles,"

Ser. No. 14/983,958, filed Dec. 30, 2015 and entitled "Metagenomics-Based Biological Surveillance System with Distributed Sequencing Centers,"

Ser. No. 14/983,971, filed Dec. 30, 2015 and entitled "Automated Metagenomic Monitoring and Characterization,"

Ser. No. 14/983,981, filed Dec. 30, 2015, now U.S. Pat. No. 9,996,662, and entitled "Metagenomics-Based Characterization using Genomic and Epidemiological Comparisons,"

Ser. No. 14/983,991, filed Dec. 30, 2015, now U.S. Pat. No. 10,127,352, and entitled "Distributed Data Processing Platform for Metagenomic Monitoring and Characterization,"

Ser. No. 14/984,004, filed Dec. 30, 2015 and entitled "Distributed Data Processing Platform for Biological Surveillance using Genomic and Epidemiological Comparisons,"

Ser. No. 14/982,341, filed Dec. 29, 2015, now U.S. Pat. No. 10,015,106, and entitled "Multi-Cluster Distributed Data Processing Platform,"

Ser. No. 14/982,351, filed Dec. 29, 2015, now U.S. Pat. No. 10,270,707, and entitled "Distributed Catalog Service for Multi-Cluster Data Processing Platform," and Ser. No. 14/982,355, filed Dec. 29, 2015, now U.S. Pat. No. 10,277,668, and entitled "Beacon-Based Distributed Data Processing Platform."

FIELD

The field relates generally to information processing systems, and more particularly to information processing systems that implement distributed processing across a plurality of processing nodes.

BACKGROUND

Conventional genomics processing is often based on culture-based isolation sequencing in which a biological sample is subject to dilution with a growth medium and then incubated to promote isolation and growth of particular desired cells. The resulting culture is then subject to sequencing which produces a sequencing result comprising genomic reads of only one or more specifically cultured organisms. Such culture-based isolation sequencing is problematic in that not all organisms can be effectively cultured. For example, some organisms may not survive the culture environment, or may be fundamentally altered by the culture environment. As a more particular example of the latter type of problem, culture-based isolation sequencing can in some cases lead to genomic mutation accumulation which alters an original pathogen sequence during culture growth time. Culture-based isolation sequencing also tends to be a lengthy and costly process. Moreover, culture-based isolation sequencing is in many cases performed in geographically-dispersed laboratories or other facilities that do not have adequate accessibility to sequencing results from other similar facilities. It can therefore be very difficult under conventional practice to predict an outbreak of a disease, infection or contamination across different geographic regions.

SUMMARY

Illustrative embodiments of the present invention provide information processing systems that are configured to process biological data derived from metagenomics sequencing of biological samples in multiple distinct data zones, such as different geographic regions. For example, some embodiments provide metagenomics-based biological surveillance systems that can be used to accurately and efficiently predict, detect, track or otherwise characterize an outbreak of a disease, infection or contamination across multiple geographic regions or other types of data zones defined by other types of boundaries. Such arrangements can be advantageously configured to provide metagenomics-based biological surveillance functionality in a decentralized and privacy-preserving manner, so as to overcome the above-noted drawbacks of conventional culture-based isolation sequencing.

In one embodiment, an apparatus comprises a distributed data processing system in which multiple processing devices communicate with one another over at least one network. The distributed data processing system is configured to obtain reads of biological samples of respective sample sources, with each of the biological samples containing genomic material from a plurality of distinct microorganisms within an environment of a corresponding one of the sample sources, and to perform distributed data analytics to characterize an actual or potential outbreak of at least one of a disease, an infection and a contamination that involves genomic material from multiple ones of the distinct microorganisms in one or more of the sample sources. Performing distributed data analytics illustratively comprises performing local analytics in respective ones of a plurality of data zones, and performing global analytics utilizing results of the local analytics performed in the respective data zones. Each of the data zones may comprise, for example, one or more sequencing centers utilized to generate a corresponding subset of the reads within that data zone. The local analytics performed in a given one of the data zones utilize reads of one or more of the biological samples sequenced in the one or more sequencing centers of the given data zone. The local analytics performed in the given data zone comprise analyzing the reads of the one or more biological samples against a local set of known gene units.

These and other illustrative embodiments include, without limitation, methods, apparatus, systems, and processor-readable storage media.

DETAILED DESCRIPTION

Illustrative embodiments of the present invention will be described herein with reference to exemplary information processing systems and associated computers, servers, storage devices and other processing devices. It is to be appreciated, however, that embodiments of the invention are not restricted to use with the particular illustrative system and device configurations shown. Accordingly, the term "information processing system" as used herein is intended to be broadly construed, so as to encompass, for example, processing systems comprising cloud computing and storage systems, as well as other types of processing systems comprising various combinations of physical and virtual processing resources. An information processing system may therefore comprise, for example, a plurality of data centers each comprising one or more clouds hosting multiple tenants that share cloud resources.

Figure 1:
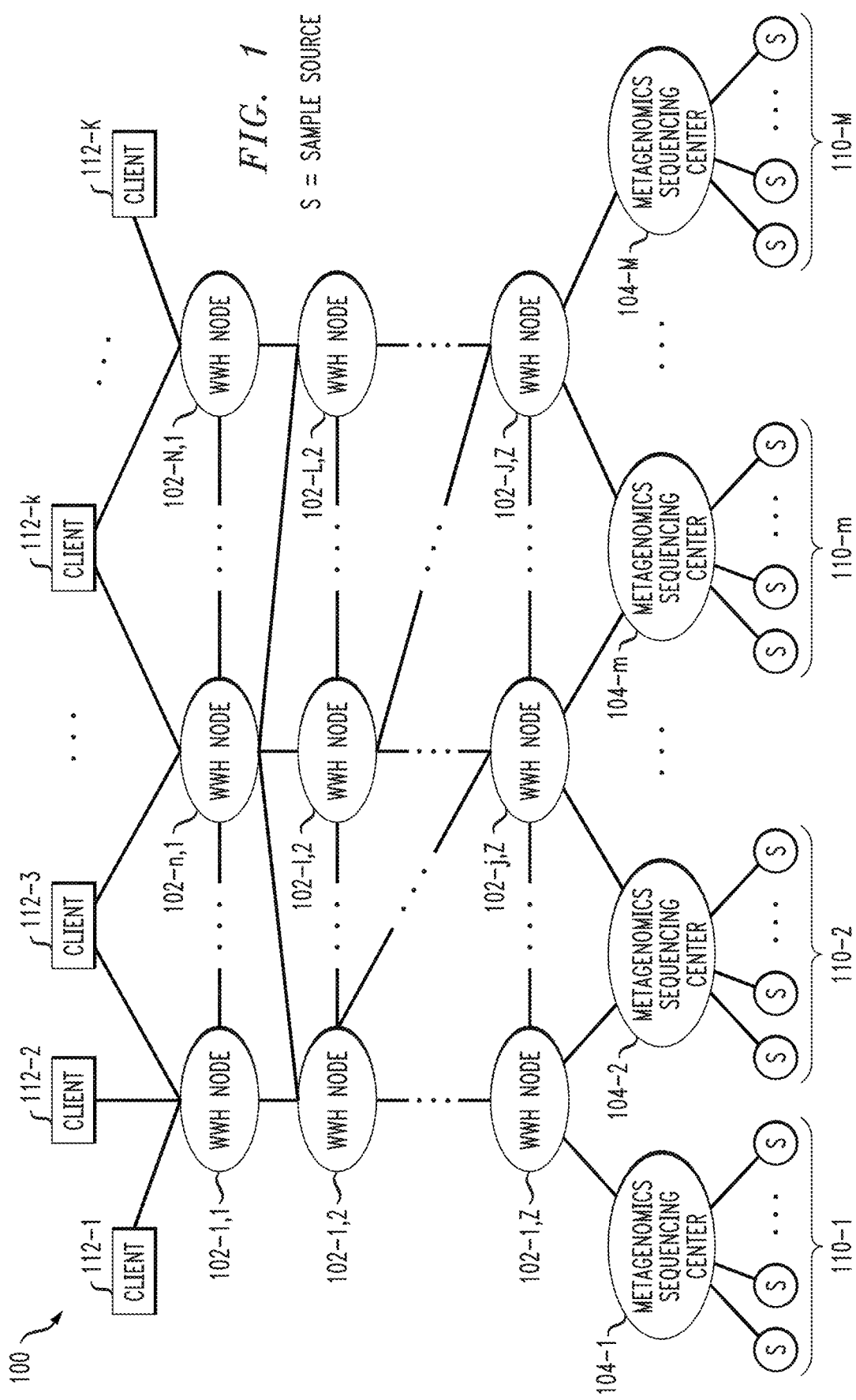
FIG. 1 is a block diagram of an information processing system configured as a metagenomics-based biological surveillance system in an illustrative embodiment of the invention.

FIG. 1 shows an information processing system configured as a metagenomics-based biological surveillance system 100 in an illustrative embodiment. The metagenomics-based biological surveillance system 100 comprises a plurality of processing nodes 102. The processing nodes 102 are arranged in multiple interconnected layers, including a first layer comprising processing nodes individually denoted as 102-1,1 . . . **102-*n*,1 . . . 102-N,1**, a second layer comprising processing nodes individually denoted as 102-1,2 ... 102-1,2 ... 102-L,2, and a Z-th layer comprising processing nodes individually denoted as 102-1,Z ... 102-j,Z ... 102-J,Z. Accordingly, this arrangement comprises Z layers of processing nodes 102, with the first, second and Z-th layers comprising N, L and J processing nodes, respectively. A wide variety of other arrangements of one or more layers of processing nodes 102 can be used in other embodiments. For example, the processing nodes in some embodiments are arranged in multiple distributed processing node clusters associated with respective distinct geographic regions or other types of data zones.

Each of the processing nodes 102 communicates either directly or via one or more other ones of the processing nodes 102 with one or more metagenomics sequencing centers, individually denoted as 104-1, 104-2, ... 104-m, ... 104-M. The processing nodes 102 are configured to communicate with one another and with their associated metagenomics sequencing centers 104 over one or more networks that are not explicitly shown.

Although the FIG. 1 embodiment and other embodiments herein advantageously utilize metagenomics sequencing centers, other embodiments can utilize other types of sequencing centers. Accordingly, embodiments of the invention are not limited to use with metagenomics sequencing. For example, some embodiments can utilize information obtained through culture-based isolation sequencing or other mechanisms, in place of or in addition to information obtained through metagenomics sequencing.

The processing nodes 102 are illustratively implemented as respective worldwide data nodes, and more particularly as respective worldwide Hadoop (WWH) nodes, although numerous alternative processing node types can be used in other embodiments. The WWH nodes are assumed to be configured to perform operations in accordance with any framework supported by an Apache Hadoop YARN ("Yet Another Resource Negotiator") cluster on one or more corresponding portions of metagenomics sequencing results received from one or more of the metagenomics sequencing centers 104. Examples of frameworks supported by the Hadoop YARN platform include MapReduce, Spark, Hive, MPI and numerous others. Apache Hadoop YARN is also referred to as Hadoop 2.0, and is described in, for example, V. K. Vavilapalli et al., "Apache Hadoop YARN: Yet Another Resource Negotiator," Proceedings of the 4th Annual Symposium on Cloud Computing, SOCC '13, pp. 5:1-5:16, ACM, New York, N.Y., USA, 2013, which is incorporated by reference herein.

In the FIG. 1 embodiment, the processing nodes 102 may collectively implement a multi-cluster distributed data processing platform. Such a platform may comprise a WWH platform that includes a plurality of potentially geographically-distributed YARN clusters each comprising a corresponding cluster of distributed data processing nodes. The WWH platform is illustratively configured for worldwide scale, geographically-dispersed computations and other types of cluster-based processing based on locally-accessible data resources.

The acronym WWH as used herein is additionally or alternatively intended to refer to a "worldwide herd" arrangement where the term "herd" in this context illustratively connotes multiple geographically-distributed Hadoop platforms. More generally, WWH is used to denote a worldwide data processing platform potentially comprising multiple clusters.

Additional details regarding WWH platforms that can be used in the FIG. 1 embodiment and other embodiments of the present invention are disclosed in U.S. patent application Ser. No. 14/982,341, filed Dec. 29, 2015 now U.S. Pat. No. 10,015,106, and entitled "Multi-Cluster Distributed Data Processing Platform," and U.S. patent application Ser. No. 14/982,351, filed Dec. 29, 2015, now U.S. Pat. No. 10,270,707, and entitled "Distributed Catalog Service for Multi-Cluster Data Processing Platform," both commonly assigned herewith and incorporated by reference herein.

Illustrative embodiments disclosed in these two patent applications provide information processing systems that are configured to execute distributed applications over multiple distributed data processing node clusters associated with respective distinct data zones. Each data zone in a given embodiment illustratively comprises a Hadoop YARN cluster configured to support multiple distributed data processing frameworks, such as MapReduce and Spark. These and other similar arrangements disclosed herein can be advantageously configured to provide analytics functionality in a decentralized and privacy-preserving manner, so as to overcome the above-noted drawbacks of conventional systems. This is achieved in some embodiments by orchestrating execution of distributed applications across the multiple YARN clusters. Computations associated with data available locally within a given YARN cluster are performed within that cluster. Accordingly, instead of moving data from local sites to a centralized site, computations are performed within the local sites where the needed data is available. This provides significant advantages in terms of both performance and privacy. Additional advantages are provided in terms of security, governance, risk and compliance.

In one embodiment, a method comprises initiating a first application in a first one of a plurality of distributed processing node clusters associated with respective data zones, each of the clusters being configured to perform processing operations utilizing local data resources locally accessible within its corresponding data zone, and determining a plurality of data resources to be utilized by the application. The method further includes identifying for each of the plurality of data resources to be utilized by the application whether the data resource is a local data resource that is locally accessible within the data zone of the first distributed processing node cluster or a remote data resource that is not locally accessible within the data zone of the first distributed processing node cluster.

For one or more of the plurality of data resources that are identified as local data resources, processing operations are performed utilizing the local data resources in the first cluster in accordance with the first application.

For one or more of the plurality of data resources that are identified as remote data resources, respective additional applications are initiated in one or more additional ones of the plurality of distributed processing node clusters and processing operations are performed utilizing the remote data resources in the corresponding one or more additional clusters in accordance with the one or more additional applications.

The process is repeated recursively for each additional application until all processing required by the first application is complete.

Processing results from the first cluster and the one or more additional clusters are aggregated and the aggregated processing results are provided to a client.

In another embodiment, a method comprises implementing a first portion of a distributed catalog service for a given one of a plurality of distributed processing node clusters associated with respective data zones, each of the clusters being configured to perform processing operations utilizing local data resources locally accessible within its corresponding data zone. The method further comprises receiving in the first portion of the distributed catalog service a request to identify for each of a plurality of data resources to be utilized by an application initiated in the given cluster whether the data resource is a local data resource or a remote data resource relative to the given cluster, and providing from the first portion of the distributed catalog service a response to the request. The first portion of the distributed catalog service in combination with additional portions implemented for respective additional ones of the plurality of distributed processing node clusters collectively provide the distributed catalog service with capability to resolve local or remote status of data resources in the data zones of each of the clusters responsive to requests from any other one of the clusters.

It is to be appreciated that a wide variety of other types of processing nodes 102 can be used in other embodiments. Accordingly, the use of WWH nodes in the FIG. 1 embodiment and other embodiments disclosed herein is by way of illustrative example only, and should not be construed as limiting in any way.

For example, additional or alternative types of processing node functionality that may be incorporated in at least a subset of the processing nodes of an information processing system in illustrative embodiments are described in U.S. Pat. No. 9,020,802, entitled "Worldwide Distributed Architecture Model and Management," and U.S. Pat. No. 9,158,843, entitled "Addressing Mechanism for Data at World Wide Scale," which are commonly assigned herewith and incorporated by reference herein.

Each of the metagenomics sequencing centers 104 in the system 100 is associated with a corresponding set of sample sources 110, individually denoted as sample source sets 110-1, 110-2, . . . 110-$m$, . . . 110-M. The sample sources each provide one or more biological samples to the corresponding metagenomics sequencing center for metagenomics sequencing. Results of the metagenomics sequencing performed on a given biological sample are illustratively provided by the metagenomics sequencing center to an associated one of the processing nodes 102 for additional processing associated with provision of biological surveillance functionality within the system 100.

The sample sources of each of the sets 110 of sample sources are individually identified using the letter S in FIG. 1. Although these sample sources are illustratively shown as being external to the metagenomics sequencing centers 104, this is by way of example only and it is assumed in some embodiments that at least a subset of the sample sources of a given set 110 are within the corresponding metagenomics sequencing center 104. Accordingly, a given metagenomics sequencing center can perform metagenomics sequencing operations using a combination of internal and external local sample sources.

The results of the metagenomics sequencing performed by a given one of the metagenomics sequencing centers 104 illustratively comprise results of reading the genomic material of one or more organisms in each of a plurality of biological samples obtained from corresponding ones of the sample sources 110. For example, the genetic material of a particular organism in a biological sample may comprise billions of base pairs. This genetic material may therefore be separated into readable chunks each of about 50 to 1000 base pairs in length. Such readable chunks are examples of what are more generally referred to as "reads" of a given biological sample. The biological sample can comprise a single organism or multiple organisms within a given environment from which the sample is taken. For example, a biological sample may be taken from a patient.

It should be understood that the above-noted reads are merely examples of what are more generally referred to herein as "metagenomics sequencing results." Such results can take different forms in different embodiments, as will be readily appreciated by those skilled in the art. For example, such metagenomics sequencing results can comprise reads that have been processed in a variety of different ways within a metagenomics sequencing center before being provided to one of more of the processing nodes 102 for additional processing. Numerous other types of metagenomics sequencing results can be used in other embodiments.

In some embodiments, the reads of biological samples are subject to mapping operations in the processing nodes 102 or the metagenomics sequencing centers 104. For example, one or more reads of a given biological sample may be subject to mapping based on string resemblance to target genomic sequences. Such a mapping arrangement is illustratively used to generate what is referred to herein as a hit abundance score vector for the given biological sample. Multiple such hit abundance score vectors generated for different biological samples are combined into a hit abundance score matrix that is processed by multiple ones of the processing nodes 102 in characterizing a disease, infection or contamination, or otherwise providing metagenomics-based biological surveillance functionality within the system 100, as will be described in more detail below.

Each of the processing nodes 102 is coupled directly or indirectly via one or more other ones of the processing nodes 102 to one or more clients 112. By way of example, the set of clients 112 may include one or more desktop computers, laptop computers, tablet computers, mobile telephones or other types of communication devices or other processing devices in any combination. The clients are individually denoted in the figure as clients 112-1, 112-2, 112-3, . . . 112-$k$, . . . 112-K.

The variables J, K, L, M, N and Z used in FIG. 1 denote arbitrary values, as embodiments of the invention can be configured using any desired number of processing nodes 102, processing node layers, metagenomics sequencing centers 104 and clients 112. For example, some embodiments may include multiple metagenomics sequencing centers 104 and multiple clients 112 but only a single processing node 102, or multiple processing nodes 102 and clients 112 but only a single metagenomics sequencing center 104. Numerous alternative arrangements are possible, including embodiments in which a single system element combines functionality of at least a portion of a processing node and functionality of at least a portion of a metagenomics sequencing center. Thus, alternative embodiments in which the functions of a WWH node and a metagenomics sequencing center are at least partially combined into a common processing entity are possible.

The processing nodes 102 in some embodiments are implemented at least in part as respective analysis nodes. The analysis nodes may comprise respective computers in a cluster of computers associated with a supercomputer or other high performance computing (HPC) system. The term "processing node" as used herein is intended to be broadly construed, and such nodes in some embodiments may comprise respective compute nodes in addition to or in place of providing analysis node functionality.

The system 100 may include additional nodes that are not explicitly shown in the figure. For example, the system 100 may comprise one or more name nodes. Such name nodes may comprise respective name nodes of a Hadoop Distributed File System (HDFS), although other types of name nodes can be used in other embodiments. Particular objects or other stored data of a storage platform can be made accessible to one or more of the processing nodes 102 via a corresponding name node. For example, such name nodes can be utilized to allow the processing nodes 102 to address multiple HDFS namespaces within the system 100.

Each of the processing nodes 102 and metagenomics sequencing centers 104 is assumed to comprise one or more databases for storing metagenomics sequencing results and additional or alternative types of data.

Databases associated with the processing nodes 102 or the metagenomics sequencing centers 104 and possibly other elements of the system 100 can be implemented using one or more storage platforms. For example, a given storage platform can comprise any of a variety of different types of storage including network-attached storage (NAS), storage area networks (SANs), direct-attached storage (DAS), distributed DAS and software-defined storage (SDS), as well as combinations of these and other storage types.

A given storage platform may comprise storage arrays such as VNX® and Symmetrix VMAX® storage arrays, both commercially available from EMC Corporation. Other types of storage products that can be used in implementing a given storage platform in an illustrative embodiment include software-defined storage products such as ScaleIO™ and ViPR®, server-based flash storage devices such as DSSD™, cloud storage products such as Elastic Cloud Storage (ECS), object-based storage products such as Atmos, scale-out all-flash storage arrays such as XtremIO™, and scale-out NAS clusters comprising Isilon® platform nodes and associated accelerators in the S-Series, X-Series and NL-Series product lines, all from EMC Corporation. Combinations of multiple ones of these and other storage products can also be used in implementing a given storage platform in an illustrative embodiment.

Additionally or alternatively, a given storage platform can implement multiple storage tiers. For example, a storage platform can comprise a 2 TIERS™ storage system from EMC Corporation.

These and other storage platforms can be part of what is more generally referred to herein as a processing platform comprising one or more processing devices each comprising a processor coupled to a memory.

A given processing device may be implemented at least in part utilizing one or more virtual machines or other types of virtualization infrastructure such as Docker containers or other types of Linux containers (LXCs). The processing nodes 102 and metagenomics sequencing centers 104, as well as other system components, may be implemented at least in part using processing devices of such processing platforms.

Communications between the various elements of system 100 may take place over one or more networks. These networks can illustratively include, for example, a global computer network such as the Internet, a wide area network (WAN), a local area network (LAN), a satellite network, a telephone or cable network, a cellular network, a wireless network implemented using a wireless protocol such as WiFi or WiMAX, or various portions or combinations of these and other types of communication networks.

As a more particular example, some embodiments may utilize one or more high-speed local networks in which associated processing devices communicate with one another utilizing Peripheral Component Interconnect express (PCIe) cards of those devices, and networking protocols such as InfiniBand, Gigabit Ethernet or Fibre Channel. Numerous alternative networking arrangements are possible in a given embodiment, as will be appreciated by those skilled in the art.

It is to be appreciated that the particular arrangement of system elements shown in FIG. 1 is for purposes of illustration only, and that other arrangements of additional or alternative elements can be used in other embodiments. For example, numerous alternative system configurations can be used to implement metagenomics-based surveillance functionality as disclosed herein.

The operation of the system 100 will now be described in further detail with reference to the flow diagram of FIG. 2. The process as shown includes steps 200 through 204, and is suitable for use in the system 100 but is more generally applicable to other types of metagenomics-based biological surveillance systems.

In step 200, a first processing node is configured for communication with one or more additional processing nodes and with one or more of a plurality of geographically-distributed metagenomics sequencing centers via one or more networks. Each of the metagenomics sequencing centers is assumed to be configured to perform metagenomics sequencing on biological samples from respective sample sources in a corresponding data zone. In the context of the FIG. 1 embodiment, a first one of the WWH nodes 102 is configured for communication with one or more additional ones of the WWH nodes 102 and with one or more of the metagenomics sequencing centers 104. Each of the metagenomics sequencing centers 104 is configured to perform metagenomics sequencing on biological samples from its corresponding locally-accessible one of the sets 110 of sample sources. The sample sources providing the biological samples that are processed in the metagenomics sequencing centers illustratively comprise one or more of water sources, food sources, agricultural sources and clinical sources, as well as additional or alternative sources, in any combination.

In step 202, metagenomics sequencing results obtained from one or more of the metagenomics sequencing centers are processed in the first processing node. Again, in the context of the FIG. 1 embodiment, a given one of the WWH nodes 102 can process metagenomics sequencing results from one or more of the metagenomics sequencing centers 104. The processing of the metagenomics sequencing results in the given WWH node may comprise, for example, determining if genomic material in the metagenomics sequencing results is present in one or more known genomes.

The given WWH node and at least a subset of the remaining WWH nodes 102 can collectively form multiple YARN clusters with each such cluster being associated with a corresponding one of the metagenomics sequencing centers 104. Each of the WWH nodes 102 in such an arrangement is configured to perform operations in accordance with at least one supported framework of its YARN cluster on one or more corresponding portions of the metagenomics sequencing results.

The metagenomics sequencing results for a given one of the biological samples may comprise a complete sequencing of the biological sample performed without utilization of a culture-based pathogen isolation process. The complete sequencing in such an arrangement may comprise a set of reads for all organisms in the sample. Alternatively, the metagenomics sequencing results for a given one of the biological samples may comprise a subset of reads for the given biological sample that are determined to match existing reads from other samples. In some embodiments, the metagenomics sequencing results for a given one of the biological samples may comprise a subset of reads for the given biological sample that excludes any reads that match a human genome.

The processing of the metagenomics sequencing results may illustratively comprise generating a hit abundance score vector for a given one of the biological samples, with the hit abundance score vector comprising a plurality of entries corresponding to respective occurrence frequencies of at least one read of the given biological sample in respective target genomic sequences.

In some embodiments, the entries of the hit abundance score vector generated for the given one of the biological samples may each be normalized based at least in part on a length of the corresponding one of the target genomic sequences.

Additionally or alternatively, the occurrence frequency in a given one of the entries of the hit abundance score vector generated for the given one of the biological samples may comprise a cumulative occurrence frequency comprising a combination of respective individual occurrence frequencies for respective ones of a plurality of individual reads of the given biological sample in a corresponding one of the target genomic sequences. The plurality of individual reads may exclude reads associated with one or more host genomic sequences.

In step 204, surveillance functionality relating to at least one designated biological issue is provided on behalf of one or more requesting clients based at least in part on the processing of metagenomics sequencing results performed by the first processing node and related processing performed by one or more of the additional processing nodes. For example, with reference to the FIG. 1 embodiment, a given one of the WWH nodes 102 can provide surveillance functionality to one or more of the clients 112 based on its processing of metagenomics sequencing results from one of more of the metagenomics sequencing centers 104 in combination with related processing performed by one or more other WWH nodes 102 utilizing metagenomics sequencing results from one or more other metagenomics sequencing centers 104.

The surveillance functionality relating to at least one designated biological issue may comprise characterization of at least one of a disease, an infection and a contamination. For example, the characterization of at least one of a disease, an infection and a contamination may comprise characterizing the disease, infection or contamination as involving genomic material from multiple ones of the biological samples sequenced by different ones of the metagenomics sequencing centers 104.

Provision of the surveillance functionality in some embodiments may involve generating a hit abundance score matrix, and performing a biclustering operation on the hit abundance score matrix. The hit abundance score matrix in such an embodiment may comprise, for example, a plurality of the hit abundance score vectors, with either the rows or the columns of the hit abundance score matrix corresponding to respective different ones of the biological samples and the other of the rows and columns of the hit abundance score matrix corresponding to respective different ones of the target genomic sequences.

The biclustering operation may be performed on the hit abundance score matrix by processing the hit abundance score matrix in the form of a bipartite graph in which a first set of nodes represents respective ones of the biological samples, a second set of nodes represents respective ones of the target genomic sequences, and edges between nodes in the first set and nodes in the second set represent hit abundance scores of the hit abundance score vectors of the hit abundance score matrix.

Numerous other types of surveillance functionality not necessarily involving hit abundance matrices and biclustering may be provided in other embodiments.

Figure 2:
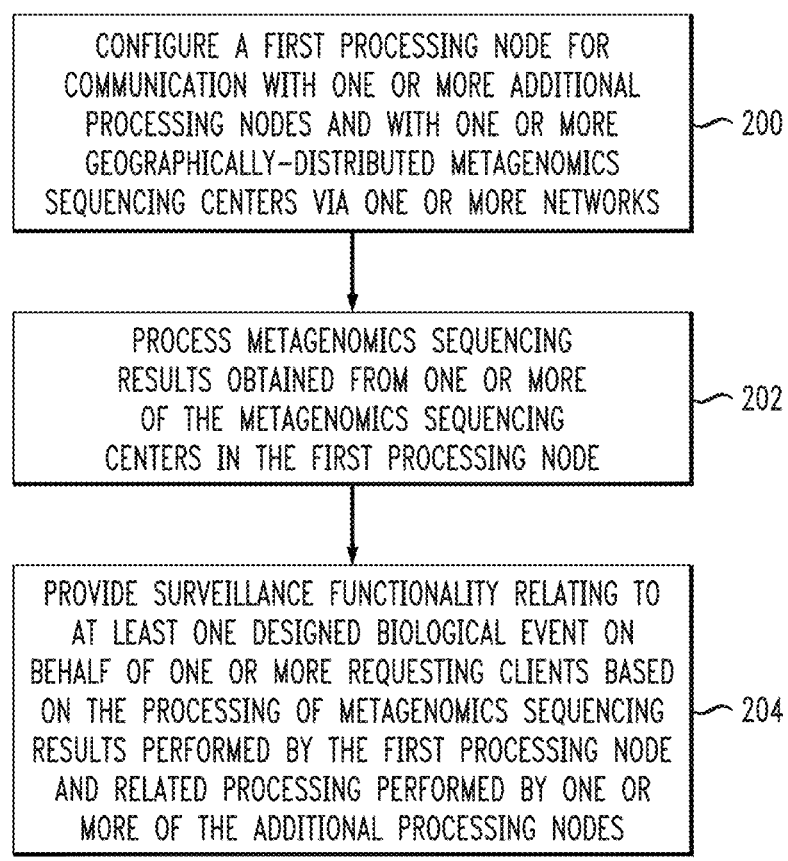
FIG. 2 is a flow diagram of an exemplary process implemented in the metagenomics-based biological surveillance system of FIG. 1.

The particular processing operations and other system functionality described in conjunction with the flow diagram of FIG. 2 are presented by way of illustrative example only, and should not be construed as limiting the scope of the invention in any way. Alternative embodiments can use other types of processing operations for implementing metagenomics-based biological surveillance functionality. For example, the ordering of the process steps may be varied in other embodiments, or certain steps may be performed concurrently with one another rather than serially. Also, one or more of the process steps may be repeated periodically for different types of surveillance functionality, or multiple instances of the process can be performed in parallel with one another on different WWH nodes or other types of processing nodes implemented within a given metagenomics-based surveillance system.

It is to be appreciated that functionality such as that described in conjunction with the flow diagram of FIG. 2 can be implemented at least in part in the form of one or more software programs stored in memory and executed by a processor of a processing device such as a computer or server. As will be described below, a memory or other storage device having executable program code of one or more software programs embodied therein is an example of what is more generally referred to herein as a "processor-readable storage medium."

Additional details relating to the operation of metagenomics-based biological surveillance systems will now be described with reference to the FIG. 1 embodiment as well as other illustrative embodiments.

Figure 3:
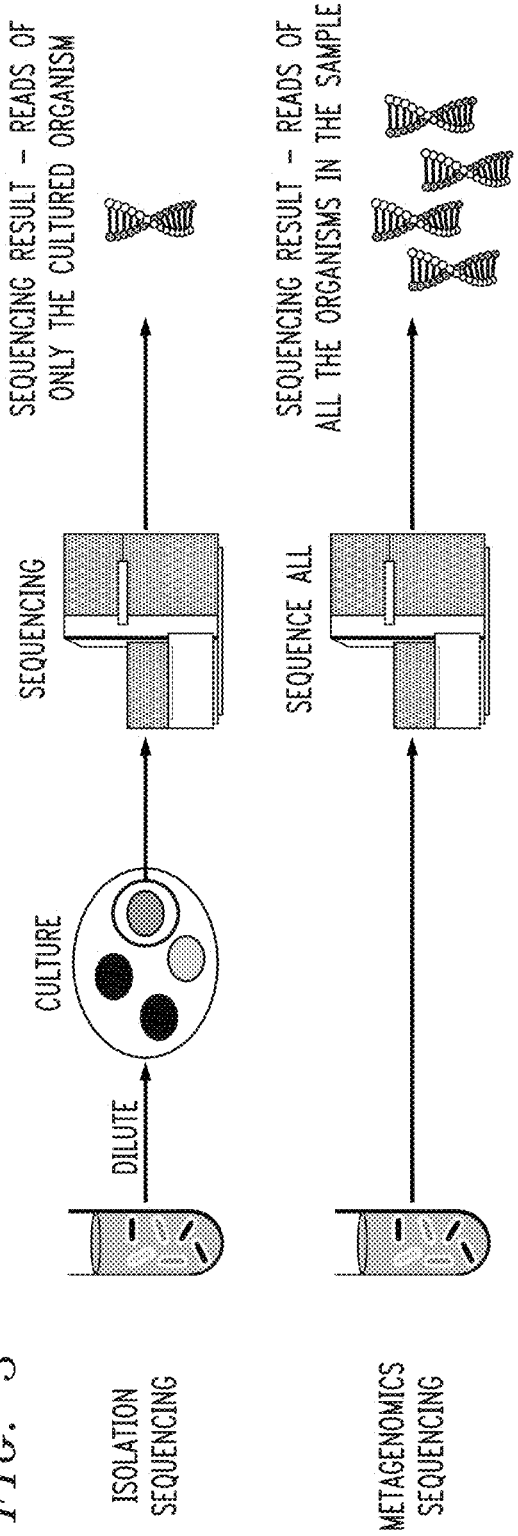
FIG. 3 illustrates distinctions between example metagenomics sequencing used in the metagenomics-based biological surveillance system of FIG. 1 and culture-based isolation sequencing.

FIG. 3 illustrates distinctions between example metagenomics sequencing used in the metagenomics-based biological surveillance system of FIG. 1 and culture-based isolation sequencing.

The upper portion of the figure illustrates culture-based isolation sequencing. As mentioned previously, in accordance with typical culture-based isolation sequencing, a biological sample is subject to dilution with a growth medium and then incubated to promote isolation and growth of particular desired cells. The resulting culture is then subject to sequencing which produces a sequencing result comprising genomic reads of only one or more specifically cultured organisms. Such culture-based isolation sequencing suffers from a number of significant drawbacks as outlined elsewhere herein.

The lower portion of the figure illustrates metagenomics sequencing such as that which is performed in one of the metagenomics sequencing centers 104 on a given biological sample obtained from a sample source in the corresponding one of the sample source sets 110. The metagenomics sequencing process advantageously avoids the drawbacks of culture-based isolation sequencing. More particularly, the metagenomics sequencing results for a given one of the biological samples as illustrated in the lower portion of FIG. 3 comprises a complete sequencing of the biological sample performed without utilization of a culture-based pathogen isolation process. The complete sequencing in this particular embodiment is assumed to comprise a set of reads for all organisms in the sample.

It should be noted that the metagenomics sequencing result for a given biological sample obtained from a single sample source may comprise millions of short reads. As noted above, the sample sources providing the biological samples that are processed in the metagenomics sequencing centers 104 in the FIG. 1 embodiment illustratively comprise one or more of water sources, food sources, agricultural sources and clinical sources, as well as additional or alternative sources, in any combination. For example, the sample source can comprise a patient, a specimen, or an environment.

Figure 4:
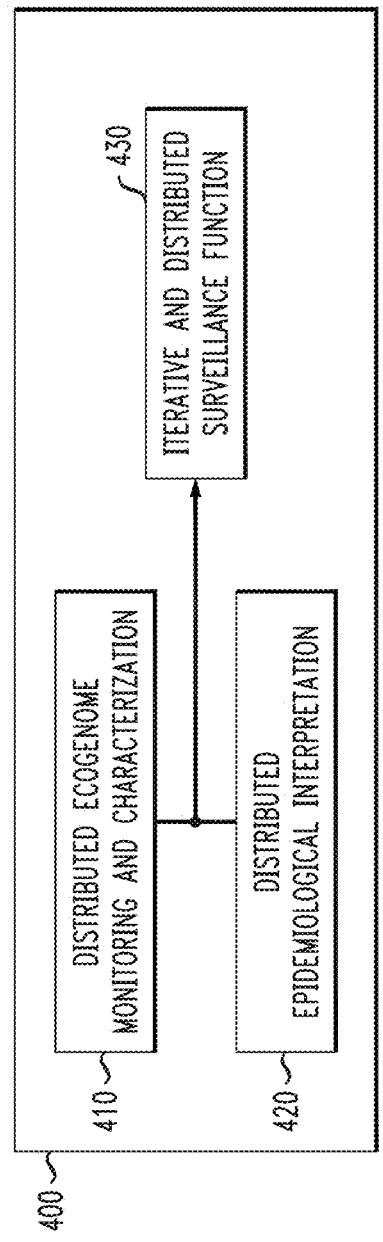
FIG. 4 illustrates an example of collective processing of a genomic comparison component and an epidemiologic comparison component to further characterize a disease, infection or contamination.

FIG. 4 illustrates an example of collective processing of a genomic comparison component and an epidemiologic comparison component to further characterize a disease, infection or contamination. More particularly, in this embodiment, a metagenomics-based biological surveillance system 400 includes a distributed ecogenome monitoring and characterization block 410 and a distributed epidemiological interpretation block 420. The blocks 410 and 420 are assumed to operate at least in part in parallel with one another utilizing metagenomics sequencing results obtained from multiple ones of the metagenomics sequencing centers 104. Outputs of the blocks 410 and 420 are utilized as inputs to an iterative and distributed surveillance function block 430 of the surveillance system 400.

In some implementations of the system 400, the distributed ecogenome monitoring and characterization block 410 is used to provide functionality such as vaccine discovery and early warnings. This may illustratively involve characterizing a disease, infection or contamination as comprising genetic material from various gene units or other target genomic sequences. The distributed epidemiological interpretation block 420 can be utilized to detect spreading patterns and place of origin. For example, epidemiologic investigation may be utilized to establish a connection between two patients in a transmission tree or other type of graph based on a comparative index between those patients.

The iterative and distributed surveillance function block 430 can utilize such information from the blocks 410 and 420 to perform functions such as deploying the vaccine or controlling spread.

The FIG. 4 embodiment is an example of an arrangement that utilizes a genomic comparison component in combination with an epidemiological comparison component. In some arrangements of this type, results of metagenomics sequencing performed on biological samples from respective sample sources are obtained, and particular ones of the biological samples that are related to a disease, infection or contamination are identified based at least in part on the results of metagenomics sequencing. A genomic comparison component may then be generated comprising hit abundance score vectors for respective ones of the identified samples. Additionally, an epidemiologic comparison component is generated, illustratively comprising a graph in which nodes corresponding to patients are connected in the graph based at least in part on patient comparative indexes. Portions of the genomic comparison component are collectively processed with portions of the epidemiologic comparison component to further characterize the disease, infection or contamination. A profile of the disease, infection or contamination, possibly in a data model of the type described elsewhere herein, can then be updated based at least in part on the further characterization. Also, one or more patient comparative indexes may be updated based at least in part on the further characterization. This process can be iteratively repeated for additional results of metagenomics sequencing performed on additional biological samples from respective additional sample sources.

The collective processing of portions of the genomic comparison component with portions of the epidemiologic comparison component may comprise combining portions of the genomic comparison component with portions of the epidemiologic comparison component to further characterize the disease, infection or contamination.

Additionally or alternatively, such collective processing may comprise generating an outbreak tree or other type of outbreak graph for the disease, infection or contamination utilizing both the genomic comparison component and the epidemiologic comparison component. In some embodiments, a community contact detection algorithm may be applied as a preprocessing operation prior to generating the outbreak graph.

As another example, the collective processing referred to above may comprise utilizing one or more of the portions of the epidemiologic comparison component in a preprocessing operation to reduce a biclustering sample space of the genomic comparison component. Such a preprocessing operation can more particularly utilize epidemiological data including at least one of time ranges, community contacts and symptoms to isolate subsets of samples to be subject to a biclustering operation.

As a further example, the collective processing of portions of the genomic comparison component with portions of the epidemiologic comparison component may comprise providing feedback from profile searching of a hit abundance score vector of a new biological sample against hit abundance score vectors of previous biological samples. In such an embodiment, if a match is found between the hit abundance score vector of the new biological sample and one of the hit abundance score vectors of the previous biological samples, the new biological sample may be subject to re-clustering based at least in part on the matching one of the previous biological samples.

It is also possible in these and other embodiments to associate a particular patient with a particular disease, infection or contamination based at least in part on statistical decision making utilizing respective portions of the genomic comparison component and the epidemiologic comparison component.

The above-described features of embodiments involving processing of both genomic comparison component and the epidemiologic comparison component are presented as illustrative examples only, and should not be considered as limiting in any way.

Figure 5:
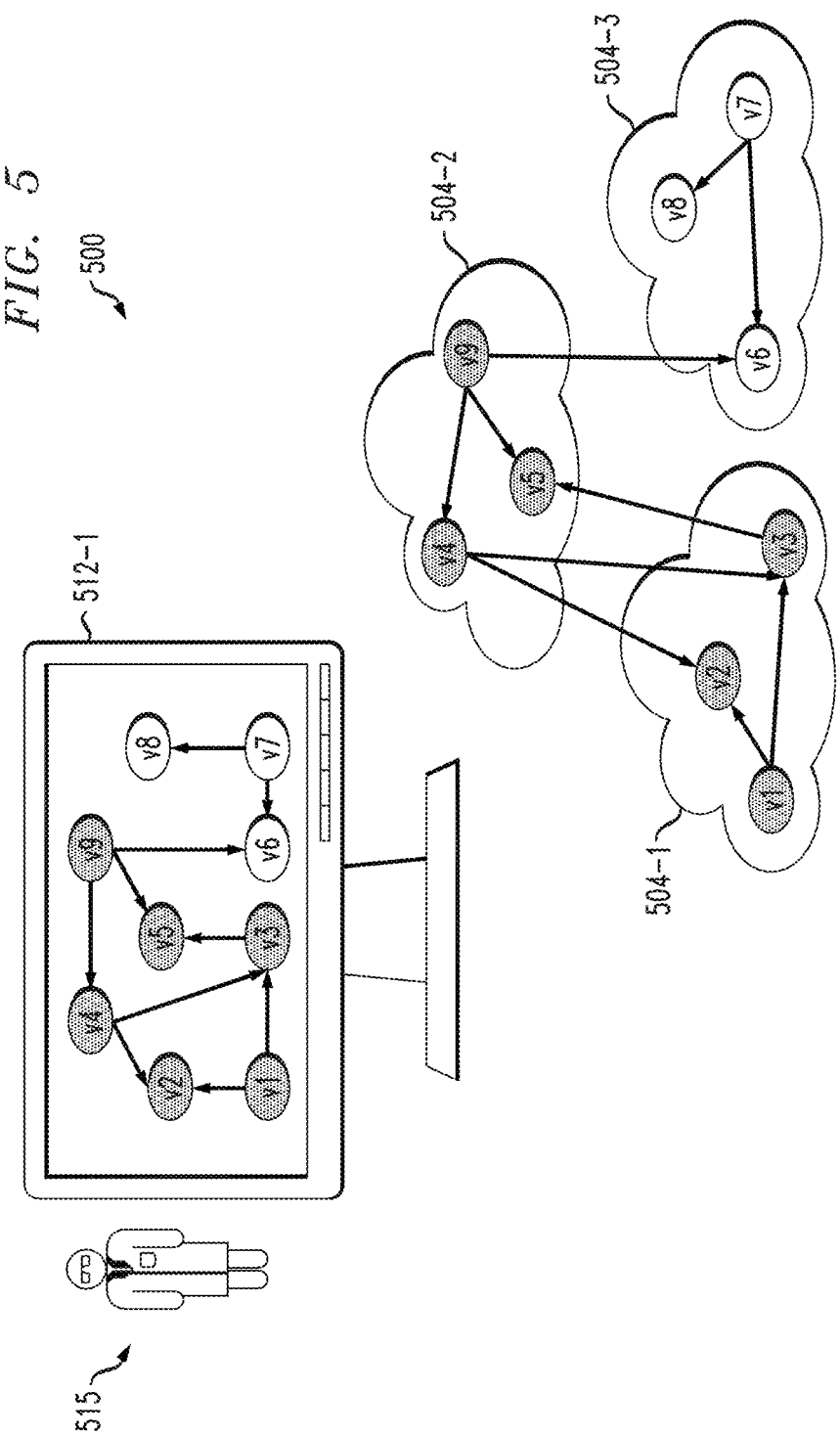
FIG. 5 illustrates the generation of global view information using metagenomics sequencing results from multiple metagenomics sequencing centers in different geographic regions.

FIG. 5 illustrates the generation of global view information using metagenomics sequencing results from multiple metagenomics sequencing centers in different geographic regions.

In the FIG. 5 embodiment, a metagenomics-based biological surveillance system 500 comprises first, second and third metagenomics sequencing centers 504-1, 504-2 and 504-3. Each of the metagenomics sequencing centers 504 is configured to perform metagenomics sequencing on biological samples from respective sample sources in a corresponding data zone. These metagenomics sequencing centers are further assumed to be geographically distributed relative to one another. For example, each may correspond to a different one of a plurality of data centers distributed worldwide.

A clinician, researcher or other user 515 associated with a client 512-1 in this embodiment receives global view information that is generated using local view information associated with respective ones of the sequencing centers 504. The global view information is more particularly presented to the user 515 via a graphical user interface (GUI) of a computer terminal of the client 512-1.

The metagenomics sequencing centers 504 of the system 500 are configured to perform metagenomics sequencing on respective sets of biological samples. For example, the first metagenomics sequencing center 504-1 is configured to perform metagenomics sequencing on a first set of biological samples. Metagenomics sequencing results from the first metagenomics sequencing center 504-1 are processed with additional metagenomics sequencing results from the other metagenomics sequencing centers 504-2 and 504-3 for respective additional sets of biological samples. The first and additional sets of biological samples may comprise, for example, patient samples from clinical sample sources. The metagenomics sequencing centers 504 are also assumed to have access to respective sets of local epidemiological data relating to the patient samples local to each of the centers.

The processing of metagenomics sequencing results in this embodiment is illustratively performed in conjunction with the associated epidemiological data accessible to respective ones of the first and additional metagenomics sequencing centers 504-1, 504-2 and 504-3 in order to generate the global view information that is provided to the client 512-1. The global view information illustratively characterizes epidemiological relationships between the metagenomics sequencing results from the first and additional metagenomics sequencing centers 504-1, 504-2 and 504-3.

For example, as illustrated in FIG. 5, each of the metagenomics sequencing centers 504 has access to a different portion of a graph, and the global view information provided to the client 512-1 comprises a complete graph. More particularly, sequencing centers 504-1, 504-2 and 504-3 have access to respective local portions of the graph that include respective sets of nodes {v1, v2, v3}, {v4, v5, v9} and {v6, v7, v8}. The global view information comprises the complete graph that includes all of these sets of nodes and their associated interconnections.

By way of example, the nodes of the complete graph may correspond to respective biological samples sequenced by respective ones of the metagenomics sequencing centers 504 with the edges between the nodes are weighted by sample-to-sample comparison scores of the metagenomics sequencing results.

Numerous other types and arrangements of graphs may be used in these and other embodiments. The term "graph" as used herein is intended to be broadly construed so as to encompass other similar arrangements such as trees.

As another example, the global view information may comprise a global epidemiological tree generated utilizing a plurality of local epidemiological trees provided as respective portions of the metagenomics sequencing results from different ones of the first and additional metagenomics sequencing centers 504. Again, such trees are considered examples of what are more generally referred to herein as "graphs."

A global epidemiological tree of this type may comprise a transmission tree in which each node corresponds to a different biological sample and a directed edge from one node to another node within the transmission tree is indicative of an epidemiological relationship between those two nodes. Another example of a graph of this type will be described below in conjunction with FIG. 30.

The global epidemiological tree may alternatively comprise, for example, a phylogenic tree in which the biological samples correspond to respective leaf nodes and are hierarchically clustered within the phylogenic tree.

In the FIG. 5 embodiment, the processing of metagenomics sequencing results from multiple ones of the sequencing centers 504 can be repeated periodically in order to update the global view information provided to the client 512-1.

For example, the processing may be periodically repeated in accordance with a sliding time window. In conjunction with a given repetition of the processing one or more nodes corresponding to new biological samples falling within the sliding time window may be added to the graph and one or more nodes corresponding to previous biological samples falling outside the sliding time window may be removed from the graph.

In some embodiments, a given one of the metagenomics sequencing centers 504 generates the global view information responsive to a topological query from a requesting client. Additionally or alternatively, at least portions of the global view information can be generated in one or more WWH nodes of the system that are in communication with the metagenomics sequencing centers.

The global view information may characterize an actual or potential outbreak of a disease, an infection or a contamination. Accordingly, the global view information may be used in some embodiments to predict a spread pattern for an actual or potential outbreak of a disease, an infection or a contamination. This may be facilitated in some embodiments by applying a community contact detection algorithm in conjunction with generating the global view information.

The global view information can additionally or alternatively be used for other purposes, such as identifying failures in one or more preventive or sanitary controls.

The FIG. 5 embodiment may be viewed as one possible example of an automation of at least a portion of the distributed epidemiological interpretation block 420 of FIG. 4. Accordingly, it may be used separate from or in combination with distributed ecogenome monitoring and characterization.

It is to be appreciated that the FIG. 5 embodiment and other embodiments herein can be implemented using a WWH application running on a WWH platform. In such an arrangement, metagenomics sequencing results may be obtained in a first processing node from one or more metagenomics sequencing centers in a first data zone associated with the first processing node, and the first processing node configured for communication with one or more additional processing nodes via one or more networks. In such an arrangement, each of the additional processing nodes may obtain additional metagenomics sequencing results from one or more metagenomics sequencing centers in respective additional data zones associated with the additional processing nodes. The additional metagenomics sequencing results are received in the first processing node from the one or more additional processing nodes via the one or more networks. The metagenomics sequencing results obtained from the one or more metagenomics sequencing centers in the first data zone are processed with the additional metagenomics sequencing results from the one or more metagenomics sequencing centers in the respective additional data zones to generate the global view information. Such global view information characterizing relationships between the metagenomics sequencing results from the metagenomics sequencing centers in the first and additional data zones. The global view information is then provided to a requesting client.

In an embodiment of this type, each of at least a subset of the processing nodes comprises at least one WWH node configured to perform operations in accordance with at least one supported framework of a YARN cluster on one or more corresponding portions of the metagenomics sequencing results. Such WWH nodes of a WWH platform are considered examples of what are more generally referred to herein as "wordwide data nodes" or still more generally as "processing nodes."

By way of example, a WWH application running on a WWH platform may be used to automate the generation of a global epidemiological tree or other type of global view information from multiple local epidemiological trees or other types of local view information associated with respective sequencing centers. Each such sequencing center may be associated with a different WWH node and corresponding YARN cluster in a multi-cluster distributed data processing platform.

A WWH platform can be used to automatically infer the connections between the local partial views of the different sequencing centers 504 in the FIG. 5 embodiment. In such an arrangement, for example, each of the sequencing centers 504 can have an associated WWH node with the multiple WWH nodes cooperating with one another to compile and deliver the global view information to the client.

Each WWH node associated with a corresponding one of the metagenomics sequencing centers 504 illustratively computes the local portion of the graph for that sequencing center. This includes the computations for all nodes and edges residing within the corresponding cloud of that sequencing center as illustrated in FIG. 5. The edges between the different local portions can be computed by a particular one of the WWH nodes based on information provided by other ones of the WWH nodes.

Such functionality may include operations such as graph computation based on comparative metagenomics, and dynamic graph recalculation including node addition and deletion. The WWH platform in embodiments of the type described above facilitates the automation of the process by permitting processing results from one WWH node to be aggregated with processing results from other WWH nodes and by providing the corresponding aggregated results back to the requesting client.

In some embodiments, a metagenomics-based biological surveillance system is configured to leverage Big Data profiles and associated Big Data analytics in processing metagenomics sequencing results in order to more accurately and efficiently predict, detect, track or otherwise characterize an outbreak of a disease, infection or contamination across multiple geographic regions or other types of data zones.

For example, in an illustrative embodiment involving use of Big Data profiles, a metagenomics-based biological surveillance system is configured to obtain results of metagenomics sequencing performed on biological samples from respective sample sources, to generate hit abundance score vectors for respective ones of the samples based at least in part on the metagenomics sequencing results, to obtain epidemiological data relating to at least one of a disease, infection or contamination characterized by one or more of the hit abundance score vectors, and to generate patient comparative indexes based at least in part on the epidemiological data. The system is further configured to obtain one or more Big Data profiles relating to one or more of the hit abundance score vectors and one or more of the comparative indexes, and to provide surveillance functionality utilizing a combination of the hit abundance score vectors and the patient comparative indexes based at least in part on information derived from the one or more Big Data profiles.

The hit abundance score vectors and the patient comparative indexes may be periodically or otherwise updated based at least in part on the one or more Big Data profiles. This may involve, for example, increasing or decreasing a given one of the comparative indexes in accordance with information derived from the one or more Big Data profiles.

A given one of the Big Data profiles may comprise at least one of location information, climate information, environment information and social media information associated with at least one of the hit abundance score vectors and the patient comparative indexes.

In some embodiments, the surveillance functionality comprises implementing a machine learning training process that associates particular ones of the hit abundance score vectors and the patient comparative indexes with particular types of information derived from the one or more Big Data profiles. Such surveillance functionality illustratively comprises detecting at least one characteristic of an actual outbreak of a particular disease, infection or contamination. Additionally or alternatively, the surveillance functionality may comprise predicting at least one characteristic of potential outbreak of a particular disease, infection or contamination, such as a location and an affected population of the potential outbreak.

The surveillance functionality in these and other embodiments may be configured to bound a search space of the hit abundance score vectors and the patient comparative indexes based at least in part on the information derived from the one or more Big Data profiles. For example, the hit abundance score vector search space may be bounded by limiting the search space to hit abundance score vectors associated with sample sources that are within a designated proximity to a location derived from the one or more Big Data profiles. This yields a more efficient search with increased precision.

These and other embodiments can be implemented utilizing distributed data processing nodes, such as WWH nodes arranged in multiple clusters associated with respective sequencing centers. Such WWH nodes are illustratively configured to perform operations in accordance with at least one supported framework of a YARN cluster on corresponding portions of metagenomics sequencing results.

In WWH embodiments that utilize Big Data profiles, a multi-cluster WWH platform can be configured to compute portions of Big Data profiles relating to climate, environment, social media and numerous other types of information and to characterize relationships of the Big Data profiles with other profiles maintained within the platform. Such embodiments can continuously iterate and produce additional output results as Big Data profiles are updated or otherwise modified.

The use of Big Data profiles and associated profile characteristics advantageously allows for more accurate and efficient computation of hit abundance score vectors, comparative indexes and other types of information utilized in providing biological surveillance functionality in illustrative embodiments disclosed herein. For example, portions of a Big Data profile relating to climate, environment or social media can be used to increase or decrease the comparative index between two patients.

Figure 6:
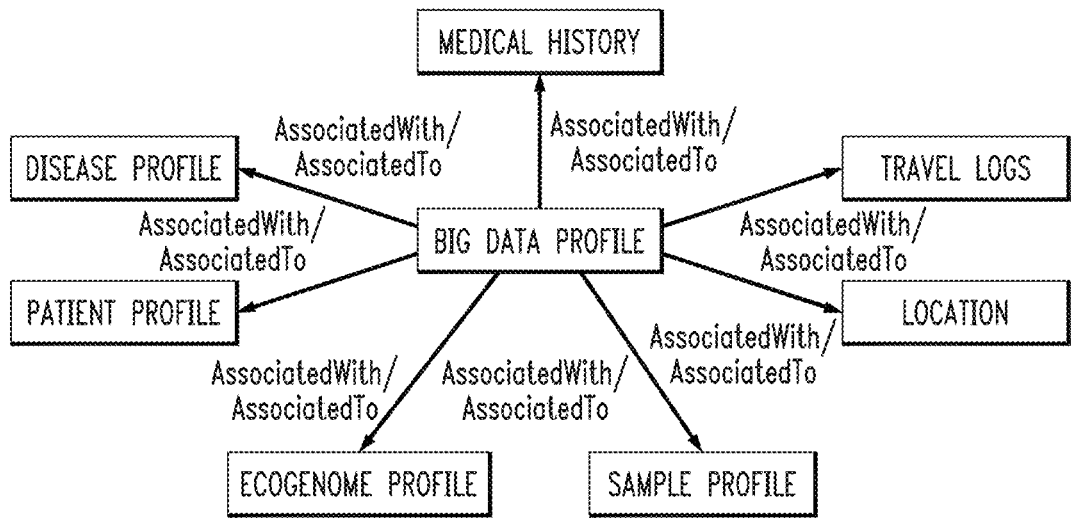
FIGS. 6-8 show examples of relationships between Big Data profiles and associated information elements in illustrative embodiments.
Figure 7:
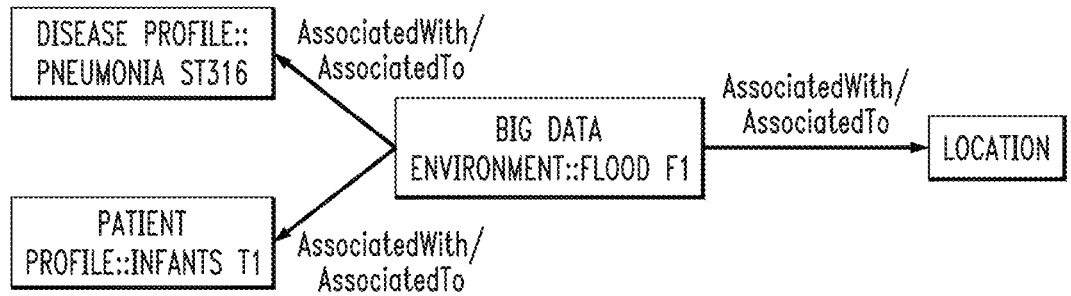
Figure 8:
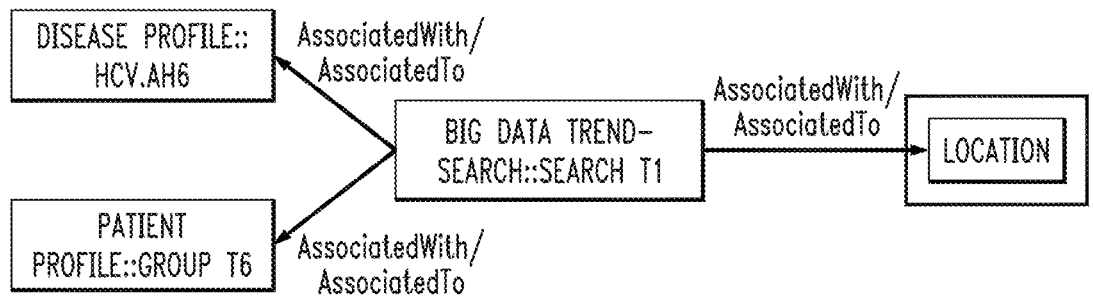

FIGS. 6-8 show examples of relationships between Big Data profiles and associated information elements in illustrative embodiments.

With reference initially to FIG. 6, a given Big Data profile is associated with a plurality of other profiles, including a disease profile, a medical history profile, travel logs, location information, a sample profile, an ecogenome profile and a patient profile.

FIGS. 7 and 8 each illustrates association between particular information of a Big Data profile and particular types of information in disease, patient and location profiles.

The associations between the Big Data profiles and other types of profiles as illustrated in FIGS. 6-8 can be based at least in part on machine learning or other types of automated training. For example, the Big Data environment relating to a flood F1 can be trained to be statistically associated with a particular disease such as pneumonia ST316 and a particular patient profile such as infants T1 as shown in FIG. 7. Based on the training data that is assembled from multiple sources, prediction can be made regarding types of diseases that have the potential to emerge, and affected populations, locations, etc. This kind of prediction can provide important benefits to public health authorities.

These are only examples, and numerous other types of Big Data profiles and other associated profiles can be used in other embodiments.

Additional details regarding Big Data profiles and associated Big Data analytics that can be implemented in illustrative embodiments of the present invention are described in U.S. Pat. No. 9,031,992, entitled "Analyzing Big Data," which is commonly assigned herewith and incorporated by reference herein.

The example profiles and corresponding associations illustrated in FIGS. 6-8 are illustratively configured in accordance with a data model.

In some embodiments, metagenomics sequencing results from a plurality of metagenomics sequencing centers associated with respective data zones are processed and a data model is configured based at least in part on the metagenomics sequencing results. One or more reasoning operations can then be performed over the data model to infer relationships between entities of the data model that are not directly expressed by the data model, and the data model updated based at least in part on the inferred relationships. These operations can be repeated utilizing additional metagenomics sequencing results that are obtained from one or more of the metagenomics sequencing centers.

Portions of the data model illustratively comprise respective profiles each characterizing at least one of a disease, infection or contamination based at least in part on the metagenomics sequencing results. For example, a given one of the profiles characterizing at least one of a disease, an infection and a contamination may comprise a characterization of the disease, infection or contamination as involving genomic material from multiple ones of a plurality of biological samples sequenced in different ones of the data zones by corresponding different ones of the metagenomics sequencing centers.

The data model in some embodiments may be in the form of a graph in which nodes correspond to respective profiles and edges between the nodes denote relationships between the corresponding profiles.

Updating the data model based at least in part on the inferred relationships may include one or more of updating a node corresponding to one of the profiles, adding a node corresponding to a new profile, deleting a node corresponding to an existing profile, and inserting one or more additional edges between respective pairs of the profiles of the graph.

The performance of one or more reasoning operations over the data model may involve applying a graph traversal tool to the graph in conjunction with the performance of the one or more reasoning operations.

Numerous other types of data models can be used in other embodiments, including models not based on graphs.

For example, data models in illustrative embodiments can be configured to utilize combinations of one or more of metagenomes, ecogenomes, pan-genomes and other types of genomic information to characterize diseases, infections or contaminations. Such data models are advantageously configured to characterize a disease, infection or contamination as being associated with a combination of genomes that when present together in each of one or more samples yield a certain set of conditions.

This approach accommodates genome plasticity as well as a wide variety of known and unknown diseases, infections or contaminations that can be characterized as a combination of genomic sequences of microbial genomes observed in the past. The data model in a given embodiment can include model elements for core genomes, including multiple species or strains, as well as for units of accessory genes that are horizontally co-transferred such as plasmids, phages, pathogenicity islands, and integrons. Such a data model is configured to recognize that accessory genes can be horizontally transferred across different strains of the same species, or across different species (e.g., as in the case of antimicrobial resistance).

The data models may be implementation-independent so as to be suitable for use on any genomic processing framework to support processing operations associated with reasoning, analyzing and dynamically classifying diseases, infections or contaminations as they emerge. This includes polymicrobial diseases, infections or contaminations that may be caused by combinations of viruses, bacteria, fungi and parasites. For example, one microorganism when present may provide a niche for other pathogenic microorganisms to colonize, or may otherwise predispose a host to colonization by other microorganisms. As another example, two or more non-pathogenic microorganisms when present together in a given sample may be identified as the cause of a disease, infection or contamination. The data models used in the illustrative embodiments are advantageously configured to support such characterizations.

Additional examples of data models utilized in illustrative embodiments will be described below with reference to FIGS. 31 through 78.

Some embodiments perform metagenomics processing utilizing what are referred to herein as "gene units" where a given gene unit illustratively comprises a portion of an assembly or other processing of one or more samples. Each such assembly or processing may result in many gene units each potentially thousands to tens of thousands of nucleotides in length. It should be noted that a "gene unit" as the term is utilized herein is intended to be broadly construed so as to encompass, for example, arrangements of genomic information that do not meet the formal definition of a gene as they are not necessarily verified or fully annotated. Accordingly, a given "gene unit" herein may but need not comprise a gene or other particular functional entity within a given genome. Gene units are considered to be an example of what is more generally referred to herein as "target genomic sequences." Such target genomic sequences may be part of an ecogenome, a pan-genome or a metagenome, or other arrangements and groupings of genetic information.

In some embodiments, gene units comprise locally-available pre-processed sequenced genomic data of a given metagenomics sequencing center, such as assembled pathogen gene units collected locally and not yet shared with global databases. Gene units may be augmented with metadata such as patient symptoms, time and location.

As mentioned previously, the metagenomics sequencing applied to a given sample results in what are referred to herein as "reads." Such reads may be utilized to generate a sample profile. For example, a sample profile can be generated by aligning the reads of a given sample to multiple gene units. The sample profile may therefore comprise a set of alignment histograms relative to respective gene units. Examples of such alignment histograms will be described below in conjunction with FIGS. 9 through 12.

It was noted above that each of the metagenomics sequencing centers 104 may comprise one or more databases for storing metagenomics sequencing results and additional or alternative types of data. For example, in some embodiments, it is assumed that each of the metagenomics sequencing centers 104 has both a sample database and a gene unit database, although other types and arrangements of databases can be used.

The sample profile in some embodiments comprises what is referred to herein as a "global" sample profile in that alignment histograms are generated for the reads of the sample against gene units from different ones of the metagenomics sequencing centers 104. This is in contrast to a "local" sample profile which includes alignment histograms that are generated for the reads of the sample against only one or more gene units that are present in the local gene unit database of the single metagenomics sequencing center 104 that performed the metagenomics sequencing on the sample.

The above-noted sample database of a given one of the metagenomics sequencing centers may comprise local sample profiles, global sample profiles or both local and global sample profiles for each of the samples that are sequenced by that center.

More particularly, the sample database of a given one of the metagenomics sequencing centers 104 illustratively comprises, for each of the samples processed in that center, the set of reads for the sample, at least one sample profile for the sample, and a metadata file. The reads are the outputs of the metagenomics sequencing applied to the sample, and as indicated above there may be millions of reads for each sample. The sample profile may comprise a global sample profile generated using metagenomics sequencing results from multiple metagenomics sequencing centers. Such a global sample profile may therefore change each time any processing relating to the sample or its reads is performed within the biological surveillance system, and is influenced by variables such as the sequencing centers used, the content of the gene units that exist in the gene unit databases of those sequencing centers, and the specific algorithms used to calculate the alignment histograms. The metadata file illustratively contains any additional information that may have been obtained about the source of the sample or the sample itself, such as patient symptoms, time and location.

The above-noted gene unit database of a given one of the metagenomics sequencing centers 104 may comprise an accumulated set of assembled or partially-assembled gene units that have been observed from samples collected locally in the given metagenomics sequencing center over some period of time or since the center started its activity. The gene units may not be unique to a specific sample and could in fact be assembled based on merging several samples together. The gene unit database in some embodiments comprises a local pathogen database or other types of local databases.

Accordingly, the gene unit database can include data from multiple sources, including data from metagenomics sequencing of multiple samples, possibly including sequencing samples that are collected locally for other purposes. It may include data that has not yet been shared with global databases such as NCBI, GenBank and others. Additionally or alternatively, the gene unit database can include copies of gene units that already exist in one or more of these global databases.

At least a subset of the gene units in the gene unit database may each have an associated metadata file that includes information such as the time and place of data collection, patient symptom measurements, etc. For example, some gene units may aggregate patient symptom measurements from multiple samples.

As noted above, a given sample profile may comprise a set of alignment histograms relative to respective gene units. Such an alignment histogram illustratively shows for each position of a nucleotide in a given gene unit the number of reads of the sample that map to that position. The positions are also referred to as "genomic sequence positions."

Figure 9:
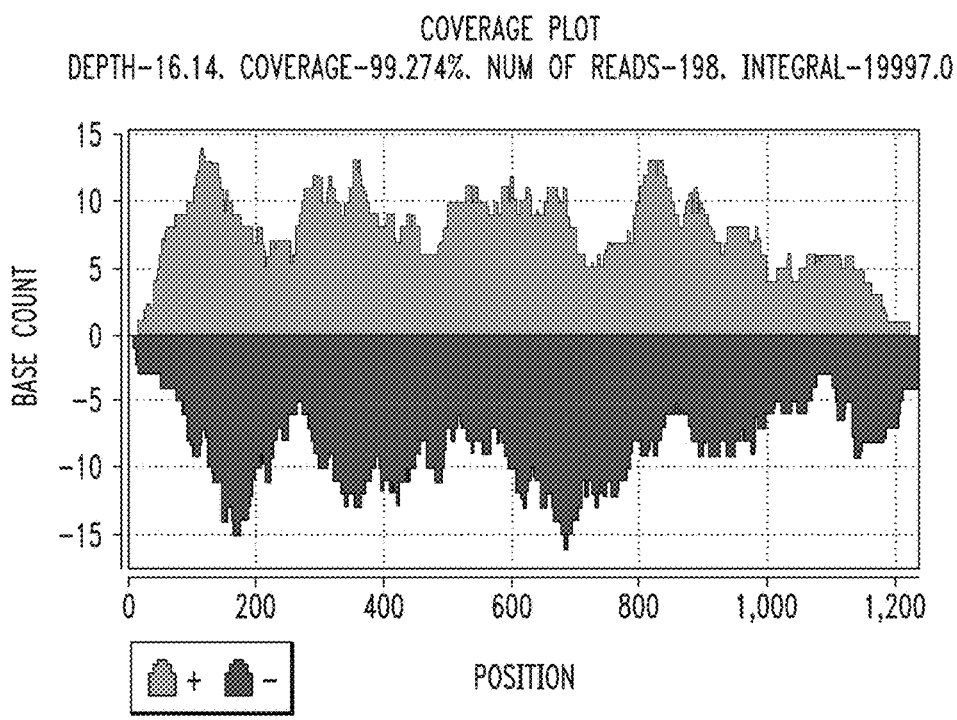
FIGS. 9, 10 and 11 show examples of alignment histograms utilized in metagenomics-based biological surveillance systems in illustrative embodiments.
Figure 10:
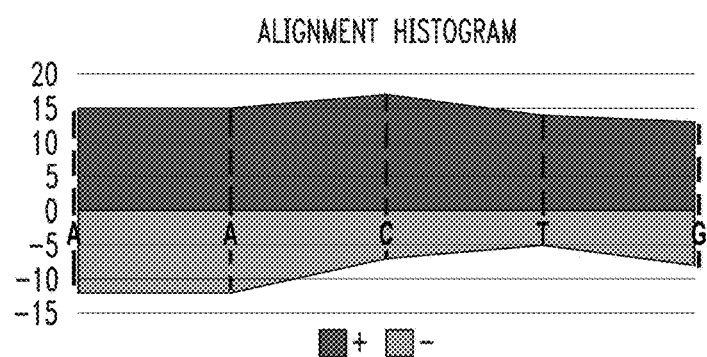
Figure 11:
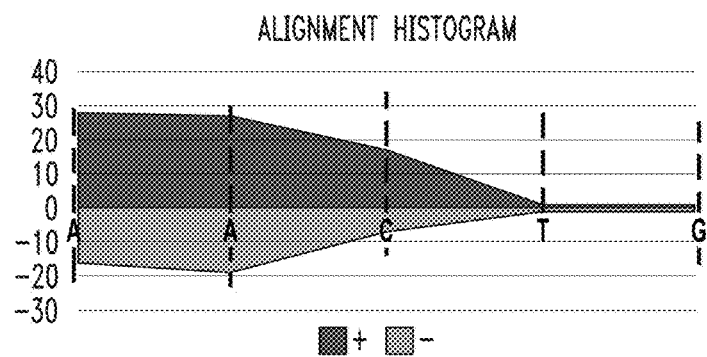

FIGS. 9, 10 and 11 show examples of alignment histograms utilized in metagenomics-based biological surveillance systems in illustrative embodiments.

Referring initially to FIG. 9, an example alignment histogram for a given sequenced sample plots base count as a function of position. More particularly, the x-axis represents the gene unit genomic sequence positions, and the y-axis represents how many reads were mapped to each position. The positive (+) area of the histogram above the x-axis shows the base counts for reads that originated from the leading or "regular" DNA strand in the sample, and the negative (−) area of the histogram below the x-axis shows the base counts for reads that originated from the complementary strand in the sample. The sign of the base counts in the negative area does not have any meaning and should be ignored. This type of alignment histogram showing separate counts for regular and complementary strands on opposite sides of the x-axis is also referred to as a "stacking" histogram.

As seen in the figure, the alignment histogram includes several parameters including depth, coverage, integral and number of reads. These parameters will each be explained in more detail below.

FIG. 10 shows a simplified example of a shorter-length version of an alignment histogram of the type illustrated in FIG. 9, with five positions along the x-axis. For each position in the gene unit, the alignment histogram counts the number of reads from the sample that are aligned to that position. As noted above, each sample includes reads from the regular and complementary DNA strands, and the corresponding counts for those reads are separated in the respective positive and negative areas above and below the x-axis. The five positions in the FIG. 10 example are denoted A, A, C, T, G, where A, T, G and C denote respective nucleotide bases of adenine, thymine, guanine and cytosine.

The depth, coverage, integral and number of reads parameters characterize the correlation between the reads of a sample and a gene unit. The number of reads represents the total number of reads that were mapped to the gene unit.

Depth is the average count per position of the reads aligned to positions in the gene unit. For example, with reference to the alignment histogram of FIG. 10, the total count for each of the five positions on both regular and complementary strands is given by A-25, A-25, C-24, T-17 and G-18. This results in an average count per position or depth of 21.8.

Coverage is the percentage of the gene unit that is covered by the sample reads, or in other words, the percentage of the gene unit positions that have reads aligned to them or a number of reads over a certain threshold aligned to them. In the FIG. 10 example, the coverage is 100% assuming a threshold of 10 reads. In some cases, the coverage can be low even though the depth is not low. Another version of the FIG. 10 example is shown in FIG. 11, and has the same depth of 21.8, but only 60% coverage.

Integral is the total area of the histogram, and represents the total of the base counts on each strand over the positions in the gene unit. For example, with reference again to the FIG. 10 example, the integral is the sum of the counts A-25, A-25, C-24, T-17 and G-18, which yields an integral of 109. Dividing the integral by the length of the gene unit yields the depth, which is 21.8 in this example.

The depth, coverage and integral of the alignment histogram are illustratively computed as follows:

$$\text{Depth: } \frac{\sum_{0 \le i \le n} |HistR[i]| + |HistC[i]|}{n}$$

$$\text{Coverage: } \frac{\sum_{0 \le i \le n} X_i}{n} * 100,$$

$$\text{such that } X_i = \begin{cases} 1, & |HistR[i]| + |HistC[i]| > t \\ 0, & \text{else} \end{cases}$$

$$\text{Integral: } \sum_{0 \le i \le n} |HistR[i]| + |HistC[i]|$$

In the above computations, HistR[i] and HistC[i] represent how many reads were mapped to base i on the regular strand and on the complementary strand, respectively, and |HistR|=|HistC|=n, where n is the length of the gene unit, and t denotes the above-described coverage threshold.

Alignment histograms and related parameters of the type described above can be provided to a client such as a given one of the clients 112 in the FIG. 1 embodiment via a GUI. Similar GUIs can be used to present corresponding sample profiles, abundance vectors, abundance matrices or other types of information based on metagenomics processing results to a given system user.

Figure 12:
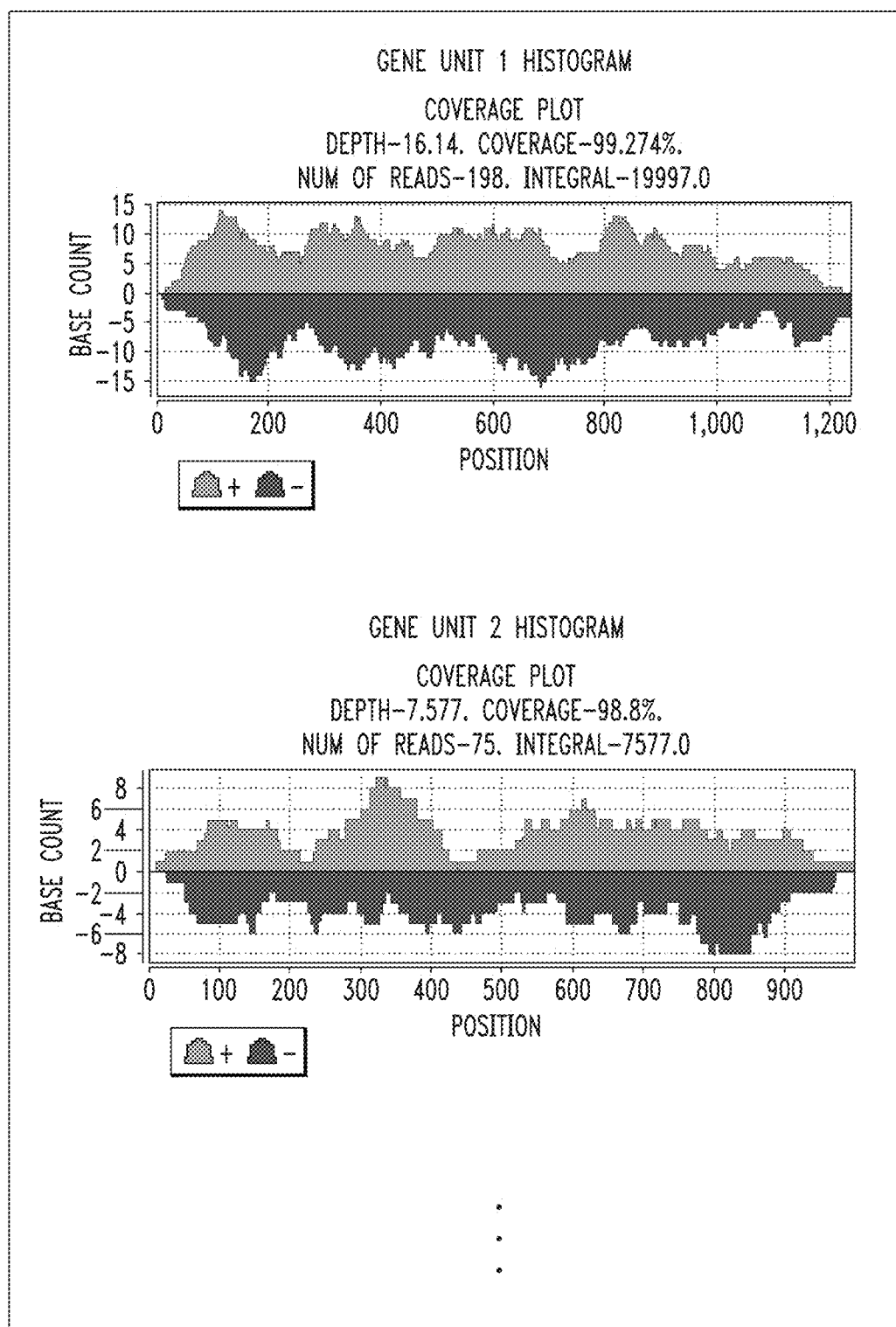
FIG. 12 shows a sample profile based on multiple alignment histograms in an illustrative embodiment.

FIG. 12 shows an example of a sample profile based on multiple alignment histograms in an illustrative embodiment. In this embodiment, the sample profile is a local sample profile denoted Sample Profile 1, assumed to be constructed for a corresponding sample denoted Sample 1. Sample Profile 1 includes first and second alignment histograms of the type shown in FIG. 9, one relative to Gene Unit 1 and another relative to Gene Unit 2, and may include similar alignment histograms for each of one or more additional gene units. As Sample Profile 1 is assumed to be a local sample profile, both of the gene units Gene Unit 1 and Gene Unit 2 are assumed to be part of the local gene unit database of the metagenomics sequencing center that performed the metagenomics sequencing on the sample. Each of the alignment histograms may be viewed as a corresponding "line" of the sample profile. The sample profile in some embodiments is created within a monitoring stage of the corresponding metagenomics sequencing center. For example, such a monitoring stage may be part of the distributed ecogenome monitoring and characterization block 410 of FIG. 4. Each line in the sample profile represents the results of application of a mapping process between the reads of the samples and a gene unit entry in the gene unit database of the specific sequencing center.

In addition to the alignment histogram, a given line in the sample profile can contain related information such as one or more of the above-noted parameters including depth, coverage, integral and number of reads.

Figure 13:
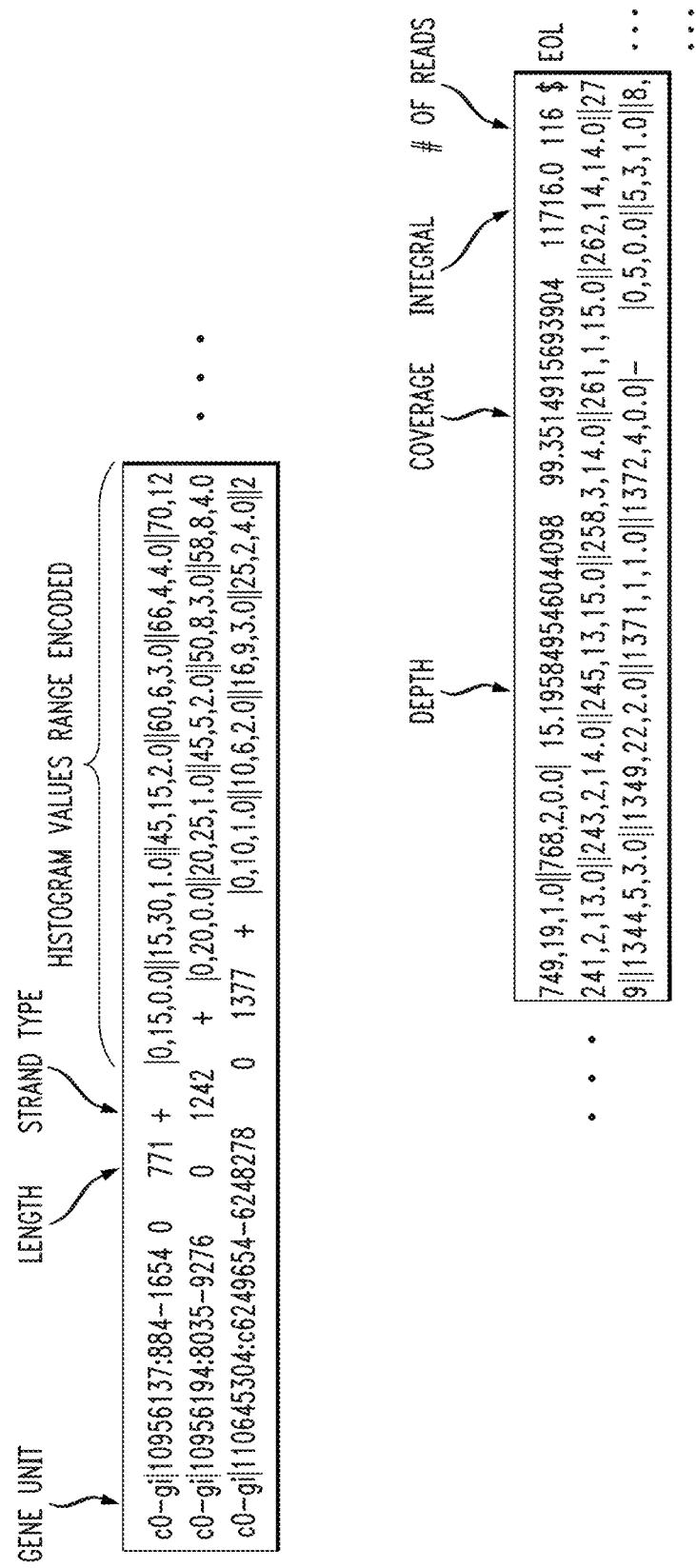
FIG. 13 shows one possible file format for a sample profile of the type shown in FIG. 12.

FIG. 13 shows one possible file format for a sample profile of the type shown in FIG. 12. In this example file format, a sample profile file includes a gene unit identifier, a gene unit length, a strand type, histogram values, depth, coverage, integral and number of reads. The notation EOL denotes the end of a given line of the file format. It is assumed in this embodiment that the histogram values are range encoded for compression.

A particular row in this example format corresponds to a single gene unit and has the following format:
<ID><start><end><strand type><hist><depth><coverage><integral><#of reads>.

In this row, <ID> is a gene unit identifier, <start> is a starting index, <end> is an end index (<end>−<start>=gene unit length), <strand type> is either "+" for the leading or regular DNA strand, or "−" for the complementary DNA strand, <hist> is a compressed histogram representation ("|range, value|"), and <depth>, <coverage>, <integral> and <#of reads> are histogram parameters as previously described.

Again, the above histogram file format is only an example, and numerous alternative file formats can be used for sample profiles in other embodiments.

Sample profiles of the type described above are utilized to generate hit abundance score vectors in illustrative embodiments. Hit abundance score vectors are also referred to herein as "abundance vectors." These abundance vectors are utilized in generating corresponding hit abundance score matrices, also referred to herein as "abundance matrices," in conjunction with the provision of metagenomics-based surveillance functionality such as characterization of a disease, infection or contamination. For example, abundance vectors in some embodiments form respective rows of an abundance matrix.

Figure 14:
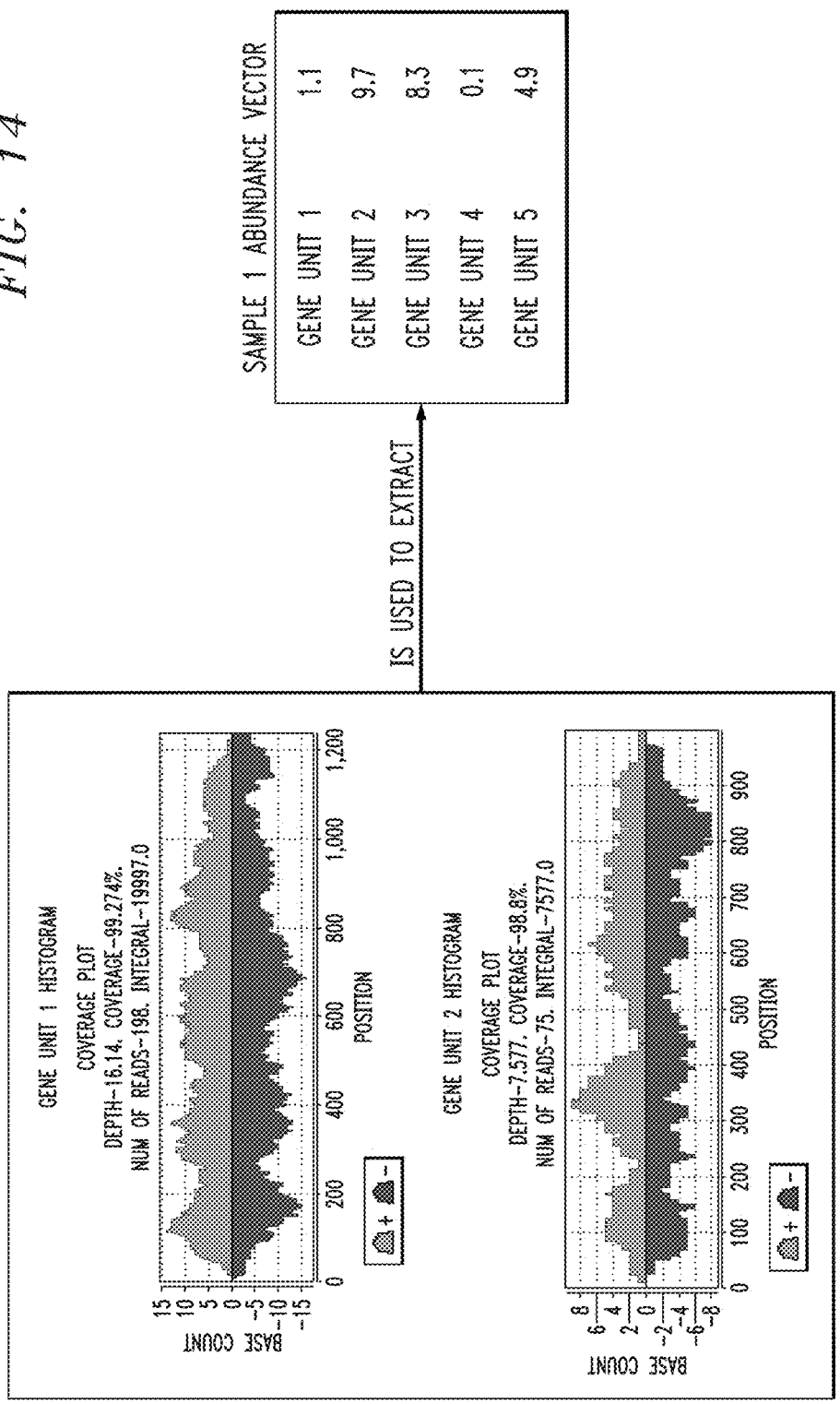
FIG. 14 illustrates generation of a hit abundance score vector for a sample profile of the type shown in FIG. 12.

Referring now to FIG. 14, generation of an example abundance vector is illustrated for a sample profile of the type shown in FIG. 12. As shown in the figure, Sample Profile 1 is used to extract an abundance vector. It is assumed for this embodiment that the Sample Profile 1 includes alignment histograms for Gene Unit 1 and Gene Unit 2 as previously described, as well as three additional gene units, denoted Gene Unit 3, Gene Unit 4 and Gene Unit 5. The five gene units utilized in generating Sample Profile 1 are denoted in the context of the present example as GU-1, GU-2, GU-3, GU-4 and GU-5, respectively.

It should be noted that the abundance vector can be built in many different ways from a given sample profile. For example, different abundance vectors can be built based on respective different ones of the depth, coverage and integral parameters previously described. Combinations of these and other parameters can also be used to construct an abundance vector. In the FIG. 14 example, it is assumed that the abundance vector is generated for Sample 1 using the depth parameter. More particularly, the abundance vector comprises a plurality of entries with each such entry corresponding to a different gene unit and indicating how abundant that gene unit was in the reads of the sample.

The abundance vector in the present example is illustratively denoted as the Sample 1 Abundance Vector or AV1, and has the following format:

AV1=[1.1 9.7 8.3 0.1 4.9]

This particular example of an abundance vector has as its five entries the corresponding depth values determined from the respective alignment histograms for the respective gene units GU-1, GU-2, GU-3, GU-4 and GU-5. These individual entries are as follows:

AV1[1]=1.1
AV1[2]=9.7

AV1[3]=8.3
AV1[4]=0.1
AV1[5]=4.9

Again, numerous other types of abundance vectors may be generated using the techniques disclosed herein.

It was assumed in the context of the present example that Sample Profile 1 from which the abundance vector AV1 is extracted is a local sample profile.

A global sample profile may be constructed in some embodiments by aggregating a plurality of local sample profiles each of which is based on a set of gene units locally accessible to a corresponding one of a plurality of metagenomics sequencing centers.

It is possible that a given gene unit may appear in multiple local sample profiles. In this case, the alignment histogram between the sample reads and the gene unit should be exactly or substantially the same in each of the multiple local sample profiles. Accordingly, the global sample profile can be configured to include only a single entry for the repeated gene unit, and may be supplemented with additional information indicating the number of metagenomics sequencing centers for which that gene unit was utilized in generating a corresponding portion of a local sample profile.

If the gene unit is present in only one sequencing center, the local sample profile based on that gene unit is added to the global sample profile.

Similarity between two gene units A and B in different sequencing centers can be measured in different ways. For example, similarity between A and B can be based on A and B exhibiting a sufficiently low number of single nucleotide polymorphisms (SNPs) between them, or similar lengths or other features.

In the generation of local or global sample profiles, gene units may be combined into one or more groups of similar gene units and the local or global sample profile can have a single entry for each such group of gene units rather than a single entry for each gene unit. Such arrangements may involve the sharing of gene units between multiple metagenomics sequencing centers in order to facilitate grouping of similar gene units. Publically available gene units from global databases such as NCBI, GenBank and others can be used for this purpose. Other embodiments can be configured to simply assume that the gene units are unique between metagenomics sequencing centers.

It is possible in some embodiments to use a general representation of a cluster of genes that is globally shared. Every gene unit that is sufficiently similar to the cluster can be tagged as being a gene unit of that cluster without the tagging metagenomics sequencing center being aware of other gene units that are tagged in the same way.

Additional details of illustrative embodiments will now be described with reference to FIGS. 15 through 28.

Figure 15:
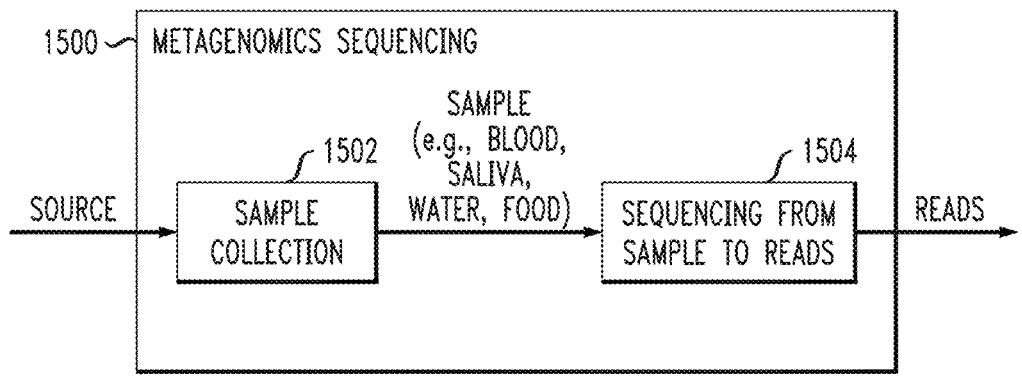
FIG. 15 illustrates generation of reads from a sample in an illustrative embodiment.
Figure 16:
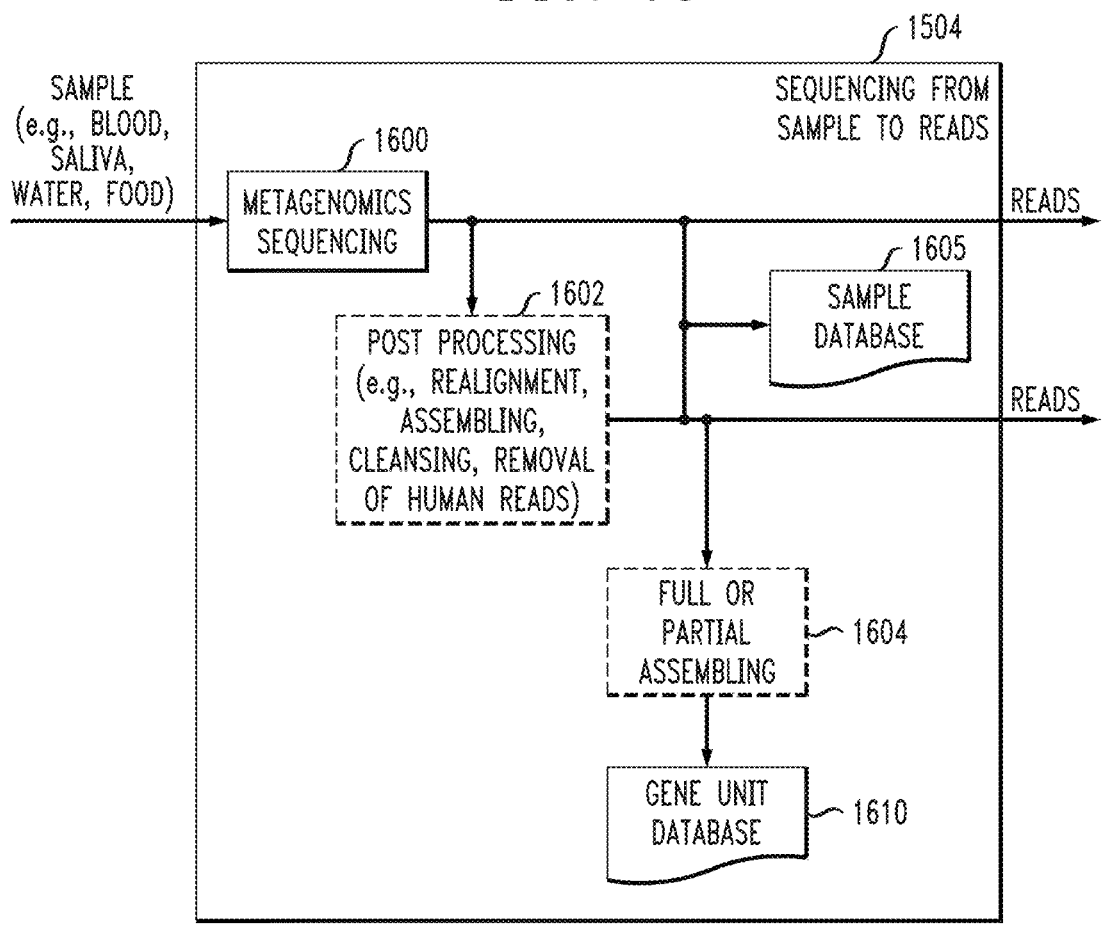
FIG. 16 shows a more detailed view of a sequencing process portion of FIG. 15.

FIGS. 15 and 16 illustrate generation of reads from a given biological sample in one of the sequencing centers such as one of the sequencing centers 104 in the FIG. 1 embodiment. Referring initially to FIG. 15, a metagenomics processing block 1500 includes a sample collection block 1502 and a sequencing block 1504. The sample collection block 1502 collects a sample from a sample source such as one of the locally-accessible sample sources in one of the sets 110 in the FIG. 1 embodiment. The sample may comprise, for example, blood, saliva, water, food, or any of a wide variety of other sample types. The sample is subject to metagenomics sequencing in the sequencing block 1504 in order to generate metagenomics sequencing results comprising a plurality of reads as illustrated.

FIG. 16 shows a more detailed view of the sequencing block 1504 of the FIG. 15 embodiment. As shown, the sequencing block 1504 comprises a metagenomics sequencing block 1600, a post-processing block 1602 and a full or partial assembling block 1604. The post-processing block 1602 illustratively encompasses operations such as re-alignment, assembling, cleansing, removal of human reads and possibly other types of operations that can be applied to the output of the metagenomics sequencing block 1600. The output of the metagenomics sequencing block 1600 provides output reads for the sample, and such output reads can also be applied to the full or partial assembling block 1604 and stored in a sample database 1605. The post-processing block 1602 can generate a separate additional output of reads as illustrated. The full or partial assembling block can be used to generate one or more gene units that are stored in a gene unit database 1610.

Although the post-processing and assembling blocks 1602 and 1604 are shown in dashed outline indicating optional blocks for this embodiment, such an indication should not be construed as an indication that any other blocks are requirements of any particular implementation. For example, other embodiments can be configured which utilize different arrangements of additional or alternative processing blocks.

In some embodiments, metagenomics-based surveillance functionality is utilized to implement what is referred to herein as a "future clinic pipeline" for characterization of a disease, infection or contamination. It is to be appreciated, however, that this and many other aspects of illustrative embodiments disclosed herein are not limited to use with metagenomics sequencing arrangements, but can more generally be applied to ecogenomic information obtained through a wide variety of other mechanisms, including, for example, conventional culture-based isolation sequencing.

By way of example, in some embodiments, a distributed ecogenome monitoring and characterization block such as block 410 of FIG. 4 is configured to compare reads from a single sample against previous gene units collected at different sequencing centers scattered all over the world. The resulting global sample profile can include, for example, information about the sample itself as well as the comparison of its reads against gene units from multiple gene unit databases associated with respective ones of the sequencing centers. Such an arrangement advantageously provides a clinician or other user with access to processing results from multiple distributed sequencing centers. This allows a given sample to be compared against multiple distinct gene unit databases.

Figure 17:
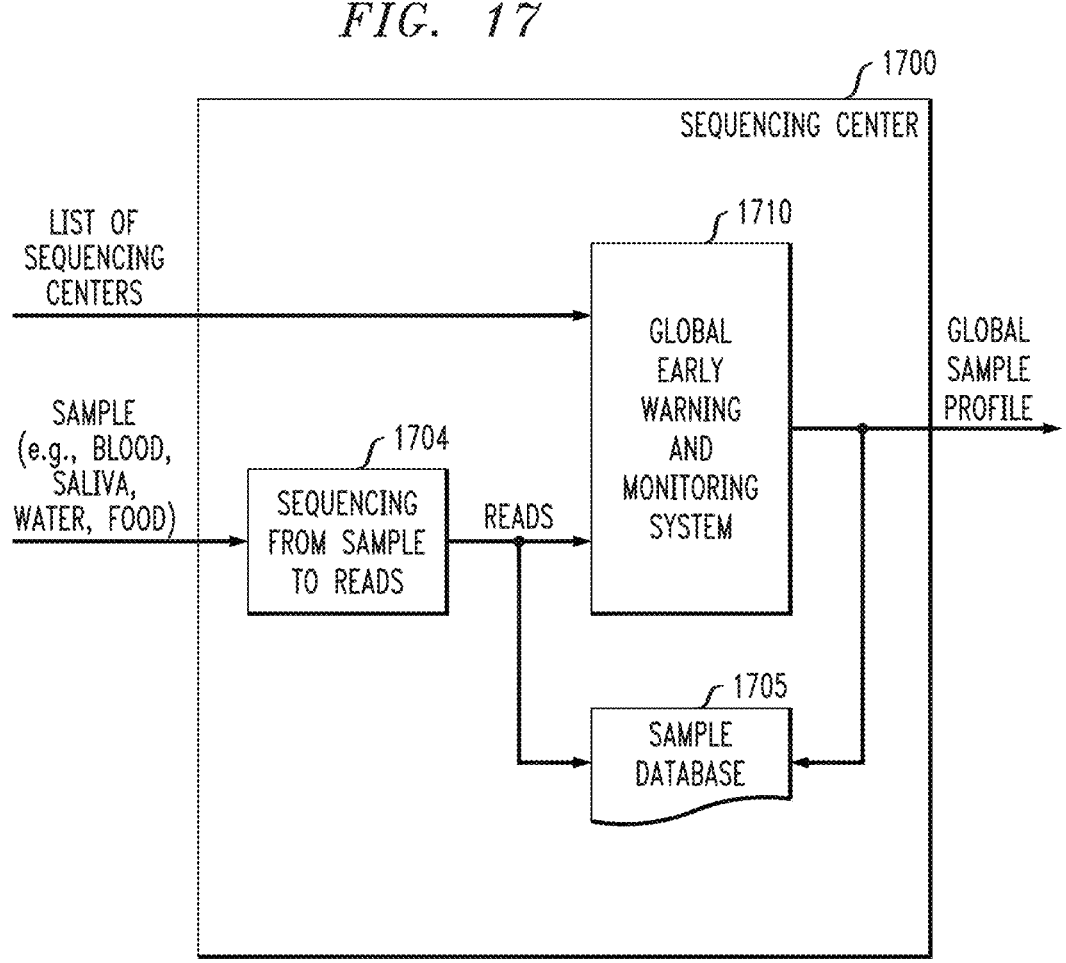
FIG. 17 shows one possible implementation of a sequencing center in an illustrative embodiment.

FIG. 17 shows one possible implementation of a sequencing center in an illustrative embodiment. In this embodiment, a sequencing center 1700 implements a sequencing block 1704 that may be similar to the sequencing block 1504 previously described in conjunction with FIGS. 15 and 16. The sequencing block 1704 generates a set of reads for a given sample. The reads are stored in a sample database 1705 and applied to a global early warning and monitoring system 1710. The global early warning and monitoring system 1710 receives a list of sequencing centers including identifiers of one or more additional sequencing centers as well as related information such as local sample profiles generated by those sequencing centers. The global early warning and monitoring system 1710 generates a global sample profile of the type previously described. Outputs of the global early warning and monitoring system 1710 are also used to update entries of the sample database 1705.

In some embodiments, as additional samples become available within the sequencing centers of the system, a disease characterization can be performed based on those samples. The entity interested in a disease characterization may be a clinician, a researcher or other system user. A given such user may comprise a human user or an application or other hardware or software entity that triggers the characterization process. Accordingly, the term "user" is intended to be broadly construed herein. Similarly, a client may be viewed as a type of human user or an associated processing device or similar entity.

By way of example, a hospital may utilize techniques disclosed herein to implement a patient administration system that automatically triggers the characterization process responsive to a threshold number of arriving patients presenting the same or similar symptoms within a given period of time. Similarly, a disease-monitoring organization such as the National Institutes of Health (NIH) can trigger the characterization process for a particular monitored disease under certain conditions. This may additionally or alternatively involve triggering of an automated request for sample donations from members of a wider population that may be suffering from a particular set of symptoms.

A given disease characterization process in illustrative embodiments can be configured as a multi-stage process that can be initiated at multiple ones of the stages depending upon the availability of inputs for those stages.

Figure 18:
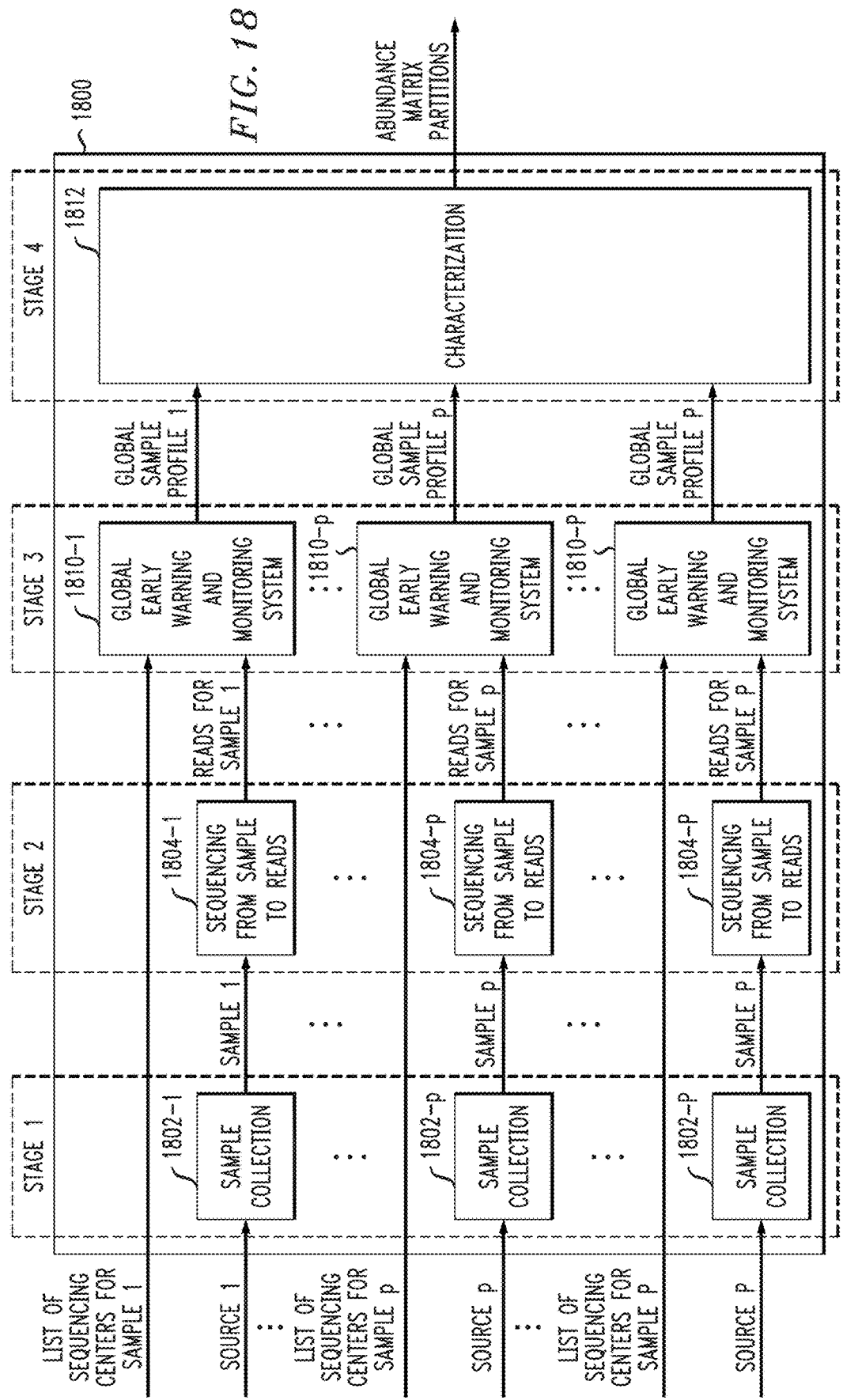
FIG. 18 shows a multi-stage disease characterization process in an illustrative embodiment.

FIG. 18 shows an example of a multi-stage disease characterization process in an illustrative embodiment. In this embodiment, a multi-stage disease characterization process 1800 comprises four stages denoted Stage 1, Stage 2, Stage 3 and Stage 4. The characterization process 1800 may be viewed as implementing P instances of the arrangement previously described in conjunction with FIG. 17. More particularly, the characterization process 1800 comprises sample collection blocks 1802-1, . . . 1802-$p$, . . . 1802-P coupled to respective sequencing blocks 1804-1, . . . 1804-$p$, . . . 1804-P. The sample collection blocks provide respective samples that are sequenced in respective ones of the sequencing blocks to provide respective sets of reads for the corresponding samples. The characterization process 1800 further comprises global early warning and monitoring systems 1810-1, . . . 1810-$p$, . . . 1810-P that receive the respective sets of reads for the P samples and generate respective global sample profiles for those samples for application to a characterization block 1812. The characterization block generates partitions of an abundance matrix of the type previously described. The partitioning of the abundance matrix may utilize a biclustering algorithm.

The abundance matrix partitions in some embodiments comprise what are referred to elsewhere herein as respective "outbreak modules" that characterize the outbreak of a disease, infection or contamination. Numerous other types of abundance matrix partitions can be utilized in other embodiments.

In Stage 1 of the characterization process 1800, samples are collected utilizing the sample collection blocks 1802. In Stage 2, the collected samples are sequenced by the sequencing blocks 1804 in order to generate reads for each sample. In Stage 3, global early warning and monitoring is performed utilizing the systems 1810 in order to generate global sample profiles. In Stage 4, the set of global sample profiles is used to characterize the disease in the characterization block 1812.

In the FIG. 18 embodiment, the characterization process 1800 utilizes selected samples that can be located in different sequencing centers. The selection of samples via the respective sample collection blocks 1802 can be performed manually or in an automated manner. For example, sample selection can be automated using an application program that selects as the set of samples to be processed those samples that share certain common characteristics and should therefore be considered related. As mentioned previously, the samples in this embodiment can be collected in the same or different sequencing centers.

In some embodiments, a WWH application configured to run on a WWH platform is utilized to provide this sample selection functionality as well as other related functionality of the characterization process 1800.

It should be noted that the characterization process 1800 can be started from various initiation points in different ones of the stages, again depending upon the availability of at least a portion of the required inputs for that stage. For example, the process can start at Stage 2, utilizing only samples that have been previously collected but without triggering the collection of any additional samples. As another example, it can start at Stage 3, utilizing only reads of samples that have previously been sequenced. As yet another example, it can start at Stage 4, by leveraging a set of global sample profiles that have been previously generated. Numerous alternative arrangements involving more or fewer processing stages and different variations in initiating point can be used in other embodiments.

The various processing operations performed within a given stage can be performed at least in part in parallel with one another. Alternatively, it is possible for each sample to be analyzed at a different instant in time. For example, Sample 1 may have been collected three months prior to Sample p, or at the same time as Sample p. The particular subsets of processing blocks 1802, 1804 and 1810 applied to respective ones of the samples can therefore execute in distinct, potentially non-overlapping time periods. As another example, the transitions from stage to stage can be highly sequential. For example, the process 1800 can be configured such that each one of the stages is completely finished before the next one starts. Again, these are only examples, and numerous alternative arrangements are contemplated.

Figure 19:
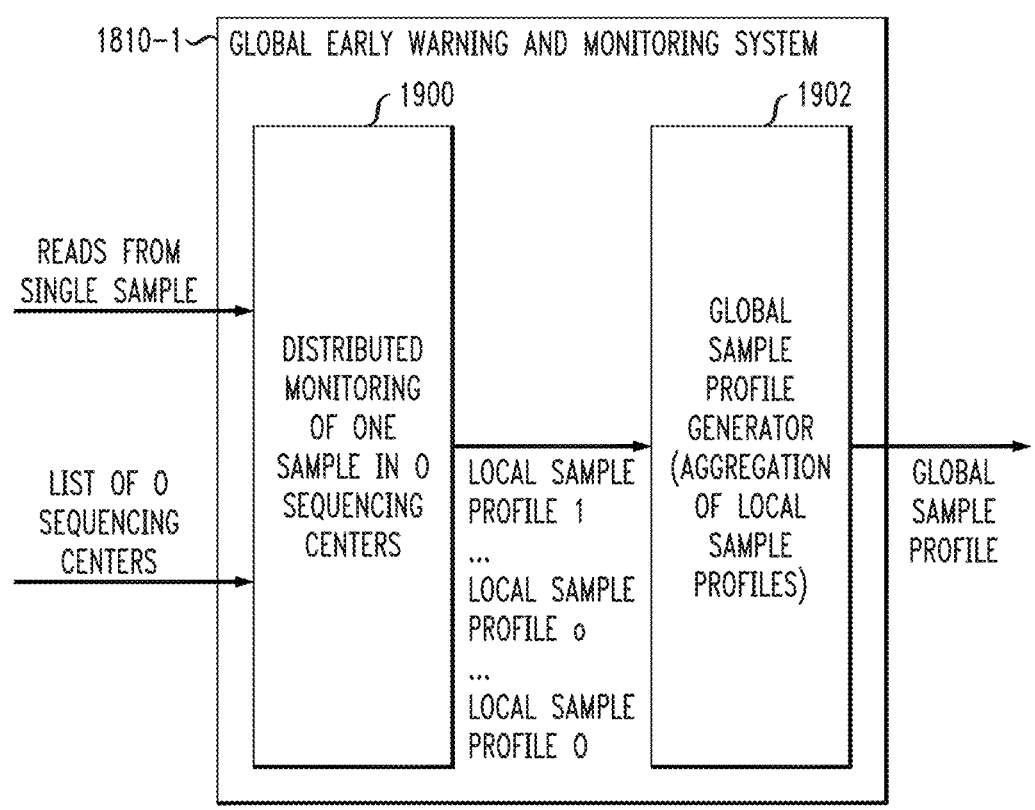
FIGS. 19 and 20 illustrate aspects of distributed ecogenomic monitoring in respective embodiments.

FIG. 19 shows a more detailed view of a given one of the global early warning and monitoring systems 1810-1 of FIG. 18. The global early warning and monitoring system 1810-1 receives reads from a single sample, and a list of O sequencing centers. A distributed monitoring component 1900 generates O local sample profiles for the single sample. These local sample profiles are denoted Local Sample Profile 1, . . . Local Sample Profile o, . . . Local Sample Profile O, and are applied to a global sample profile generator 1902. In this embodiment, the global sample profile generator 1902 generates a global sample profile as an aggregation of the O local sample profiles provided to it by the distributed monitoring component 1900. The other global early warning and monitoring systems 1810-2 through 1810-P of the FIG. 18 embodiment are assumed to be configured in a similar manner.

Figure 20:
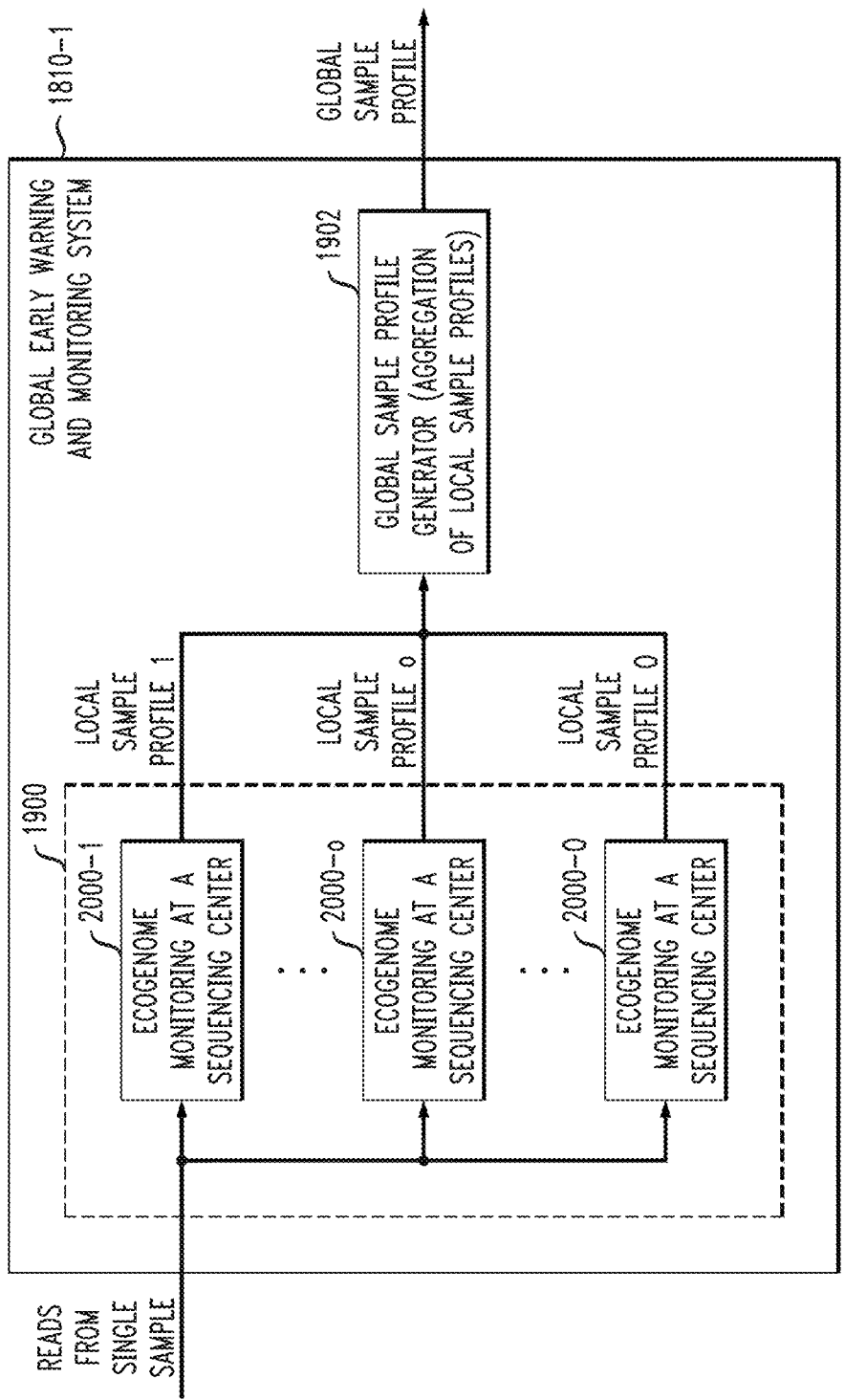

Referring now to FIG. 20, the distributed monitoring component 1900 can be seen in greater detail. As illustrated in the figure, the distributed monitoring component 1900 comprises a plurality of ecogenome monitoring components 2000-1, . . . 2000-$o$, . . . 2000-O, each associated with a different one of a plurality of sequencing centers. The ecogenome monitoring components 2000 produce respective ones of the local sample profiles denoted Local Sample Profile 1, . . . Local Sample Profile o, . . . Local Sample Profile O. The local sample profiles are generated by mapping the reads for the single sample to gene units that are local to the gene unit database of the corresponding sequencing center. These local sample profiles are subsequently applied to the global sample profile generator 1902 and utilized to generate a global sample profile in the manner previously described.

Figure 21:
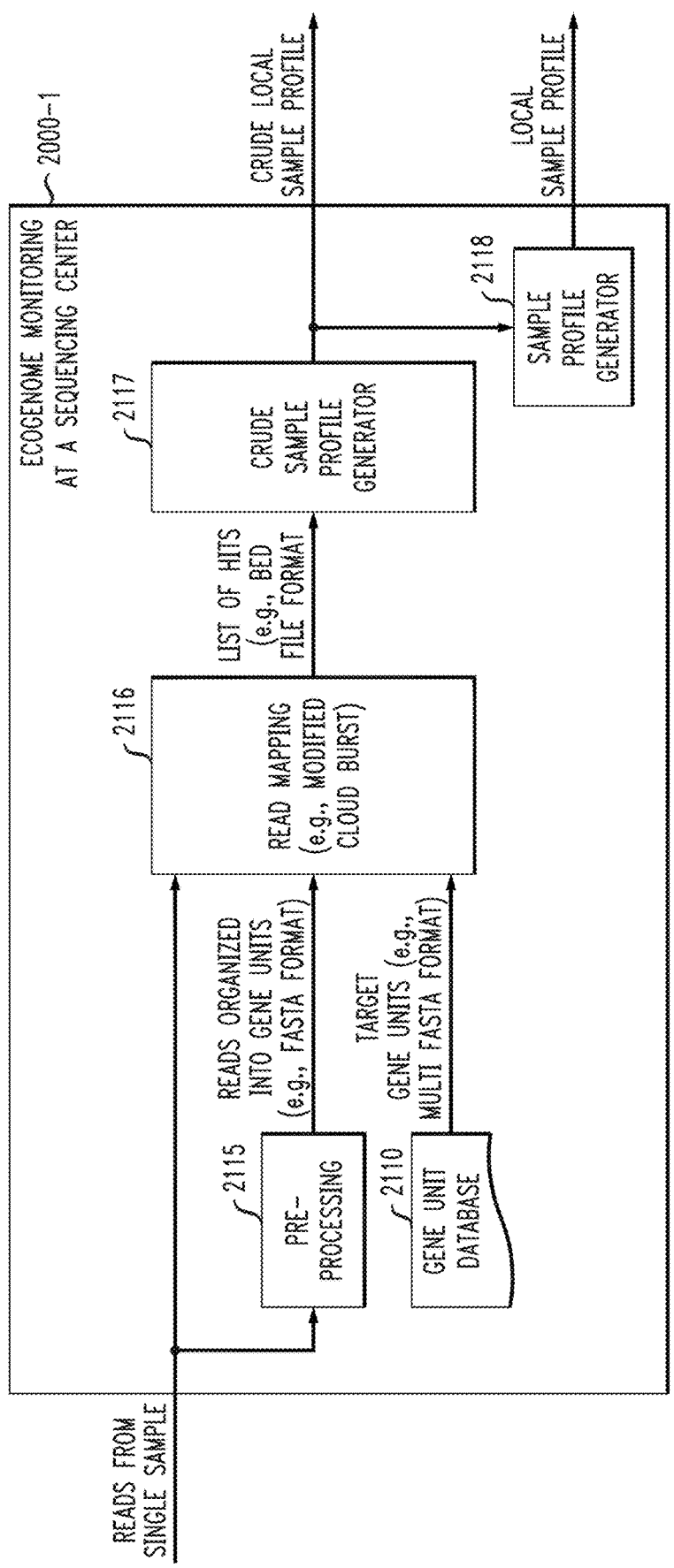
FIG. 21 illustrates ecogenomic monitoring at one sequencing center for single sample.

FIG. 21 shows a more detailed view of a given one of the ecogenome monitoring components 2000-1 of FIG. 20. The ecogenome monitoring component 2000-1 receives reads from a single sample, and processes the reads using a pre-processing block 2115 and a read mapping block 2116. The pre-processing block 2115 organizes the reads into gene units, for example, using FASTA format or another suitable format.

Figure 29:
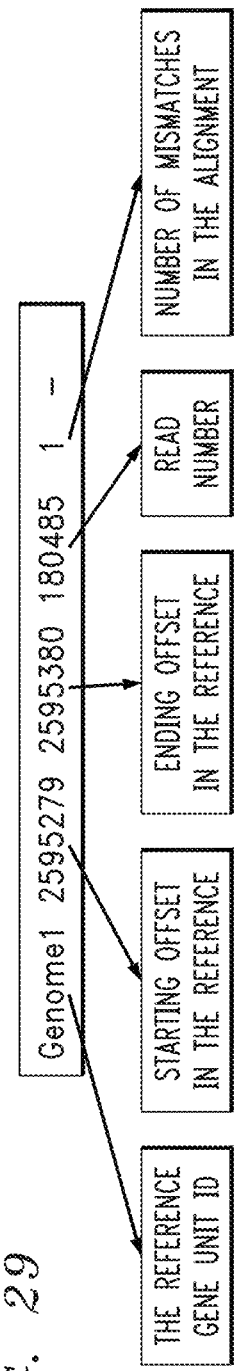
FIG. 29 shows an example file format for read mapping information in one embodiment.

The read mapping block 2116, which may illustratively implement a modified Cloud Burst mapping algorithm, maps the reads to target gene units from a gene unit database 2110 local to the corresponding sequencing center. The target gene units from the gene unit database illustratively utilize a multi-FASTA format, although numerous alternative target gene unit formats can be used in other embodiments. The output of the read mapping block 2116 illustratively comprises a list of hits, possibly in a BED format. An example of the BED format is shown in FIG. 29 and will be described in more detail below.

Figure 24:
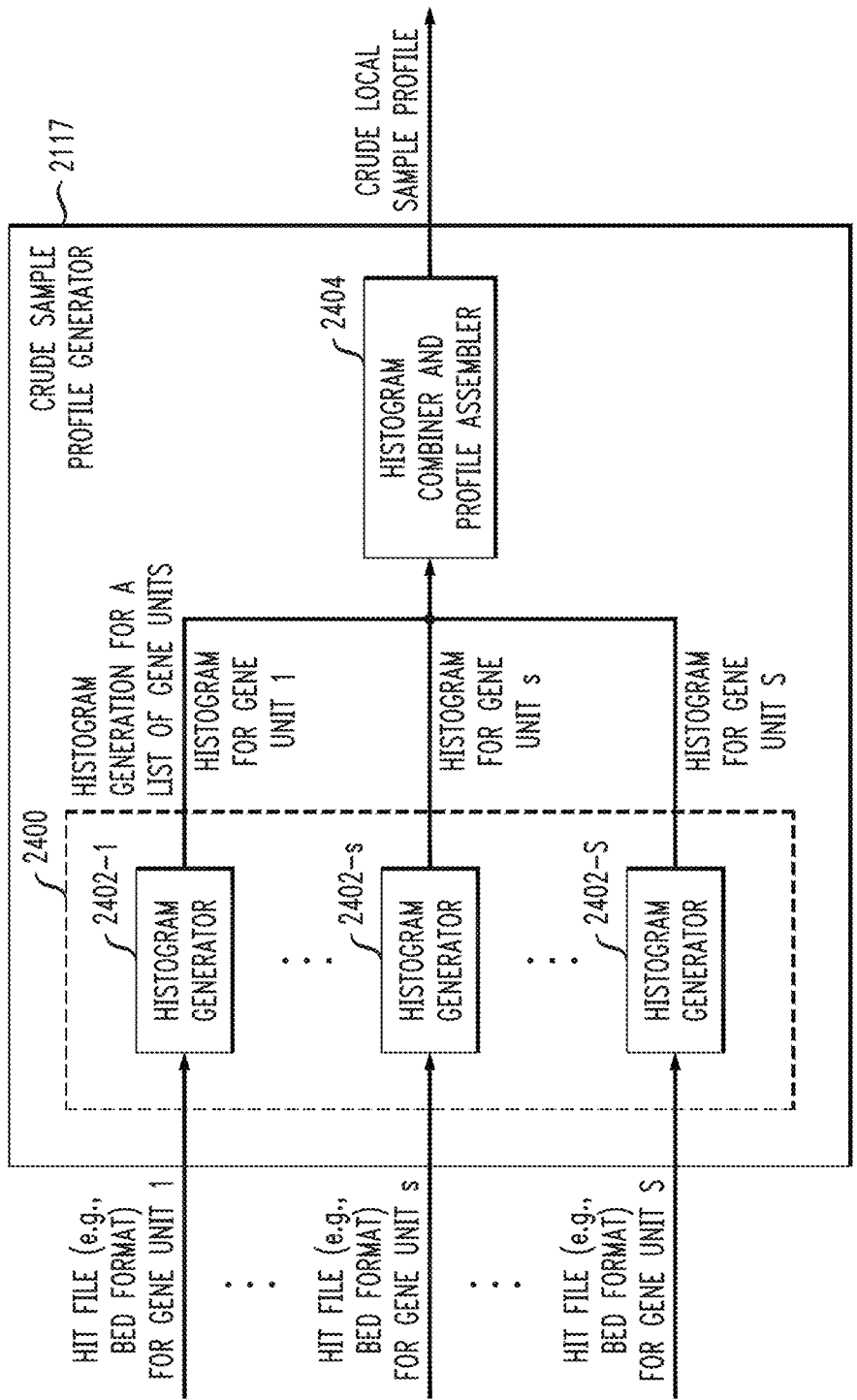
FIG. 24 shows one possible implementation of a sample profile generator in a given sequencing center.

The list of hits from the read mapping block 2116 is applied to a crude sample profile generator 2117 which generates a crude local sample profile in a manner to be described in conjunction with FIG. 24. The term "crude" in the context of this embodiment refers to any form of sample profile that has not been normalized, aligned or subject to one or more other similar operations. The crude local sample profile is further processed in a sample profile generator 2118 to generate a local sample profile. In other embodiments, the crude local sample profile generator 2117 can be eliminated such that the ecogenome monitoring component 2000-1 includes only a single profile generator suitable for generating a local sample profile of the type described elsewhere herein. It is to be appreciated that a wide variety of different types of local sample profiles can be used in illustrative embodiments.

The other ecogenome monitoring components 2000-2 through 2000-0 of the FIG. 20 embodiment are assumed to be configured in a manner similar to that illustrated in FIG. 21 and described above.

Figure 22:
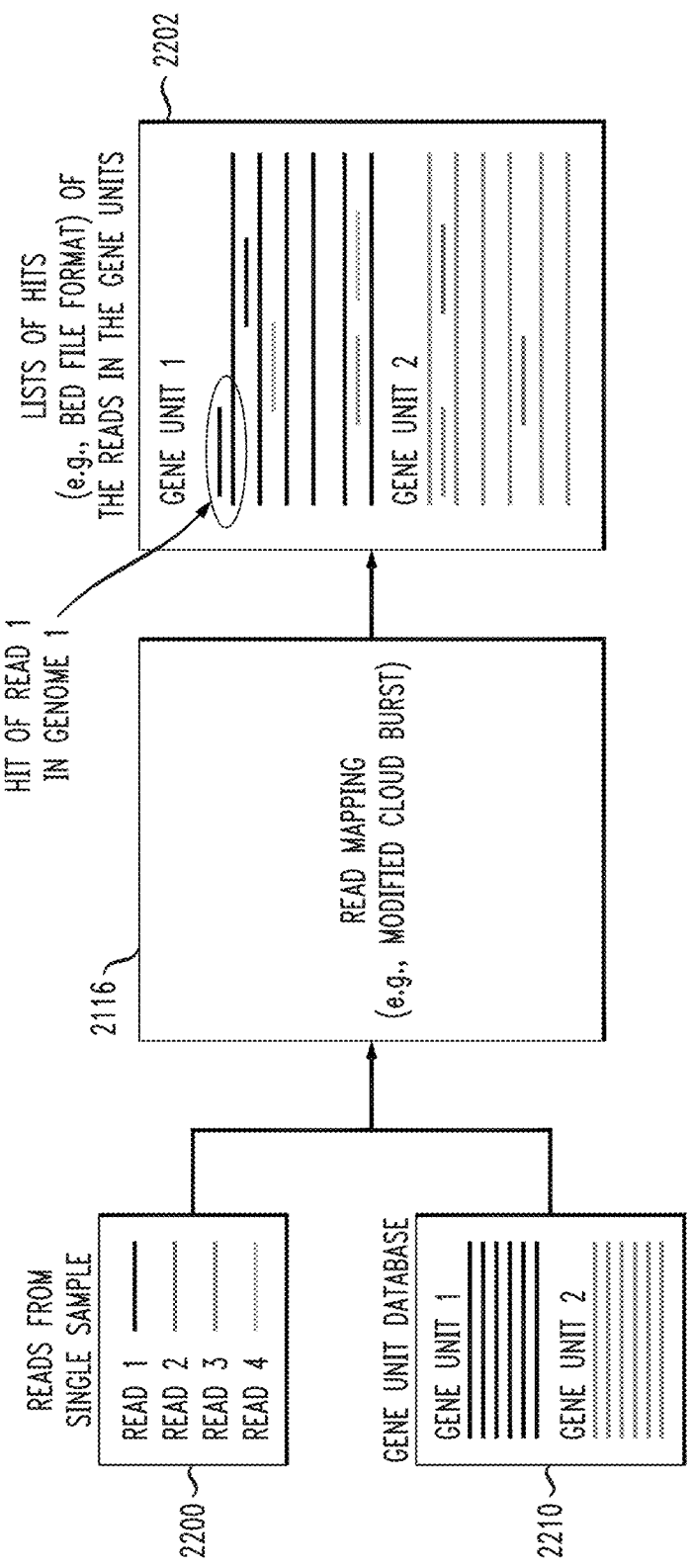
FIG. 22 illustrates the mapping of reads from a single sample to hits in multiple gene units.

Referring now to FIG. 22, the operation of the read mapping block 2116 is illustrated in more detail. In this embodiment, a set of reads 2200 from a single sample are mapped by the read mapping block 2116 against gene units from the gene unit database 2110. The set of reads 2200 includes reads denoted Read 1, Read 2, Read 3 and Read 4. The gene unit database 2110 comprises gene units denoted Gene 1 and Gene 2. The resulting output of the read mapping block 2116 comprises a list of hits 2202, possibly in BED file format, of the reads against the gene units. The list of hits 2202 includes, for example, a hit of the first read denoted Read 1 against Gene Unit 1 associated with Genome 1.

Figure 23:
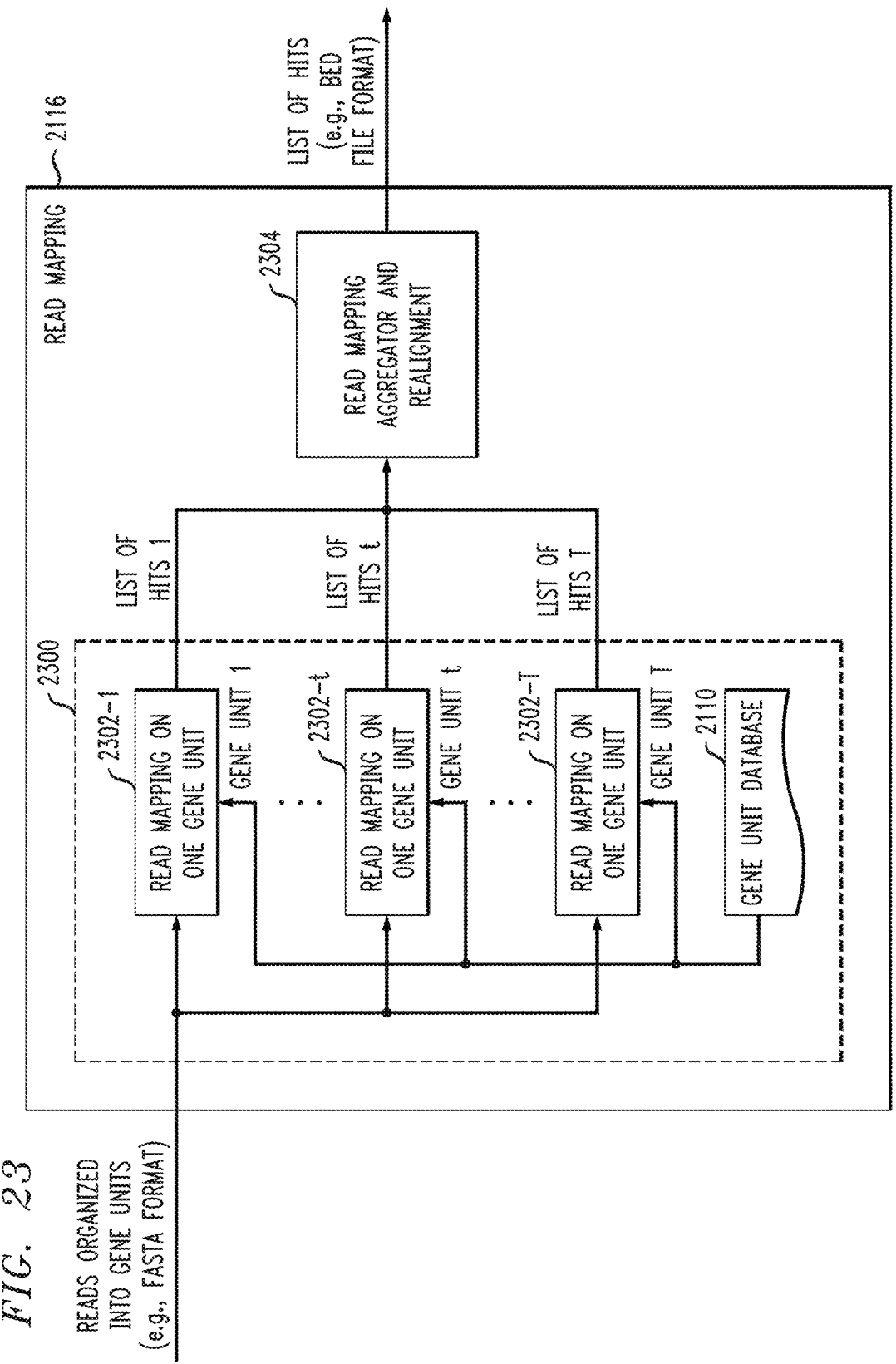
FIG. 23 illustrates read mapping for reads of one sample against a gene unit database.

FIG. 23 shows a more detailed view of the read mapping block 2116 of FIGS. 21 and 22. In this embodiment, the read mapping block 2116 comprises a read mapping component 2300 comprising a plurality of individual read mapping units 2302-1, . . . 2302-$t$, . . . 2302-T configured to perform read mapping functions for a set of reads of a given sample against respective gene units denoted Gene Unit 1, . . . Gene Unit $t$, . . . Gene Unit T from gene unit database 2110 in order to generate respective lists of hits denoted List of Hits 1, . . . List of Hits $t$, . . . List of Hits T. The lists of hits from read mapping component 2300 are applied to a read mapping aggregator and re-alignment block 2304 in order to generate the list of hits at the output of the read mapping block 2116, which as mentioned previously may be in BED format. It should be noted that the term "re-alignment" as used in this context may include any of a number of different operations relating to adjustments associated with read mapping.

With reference now to FIG. 24, one possible implementation of the crude sample profile generator 2117 is shown. The sample profile generator 2117 in this embodiment comprises a histogram generation block 2400 for a set of S gene units. The histogram generation block 2400 comprises a plurality of individual histogram generators 2402-1, . . . 2402-$s$, . . . 2402-S each generating an alignment histogram of the type described elsewhere herein for hit files corresponding to respective gene units denoted Gene Unit 1, . . . Gene Unit $s$, . . . Gene Unit S. The resulting histograms are applied to a histogram combiner and profile assembler 2404 which processes the histograms to generate the crude local sample profile. Additional processing is subsequently applied to the crude local sample profile in order to generate the local sample profile. An arrangement similar to that shown in FIG. 24 can be used as a singular sample profile generator in an embodiment without a crude sample profile generator.

Additional illustrative embodiments involving distributed ecogenomic monitoring and characterization will now be described with reference to FIGS. 25 through 27.

Figure 25:
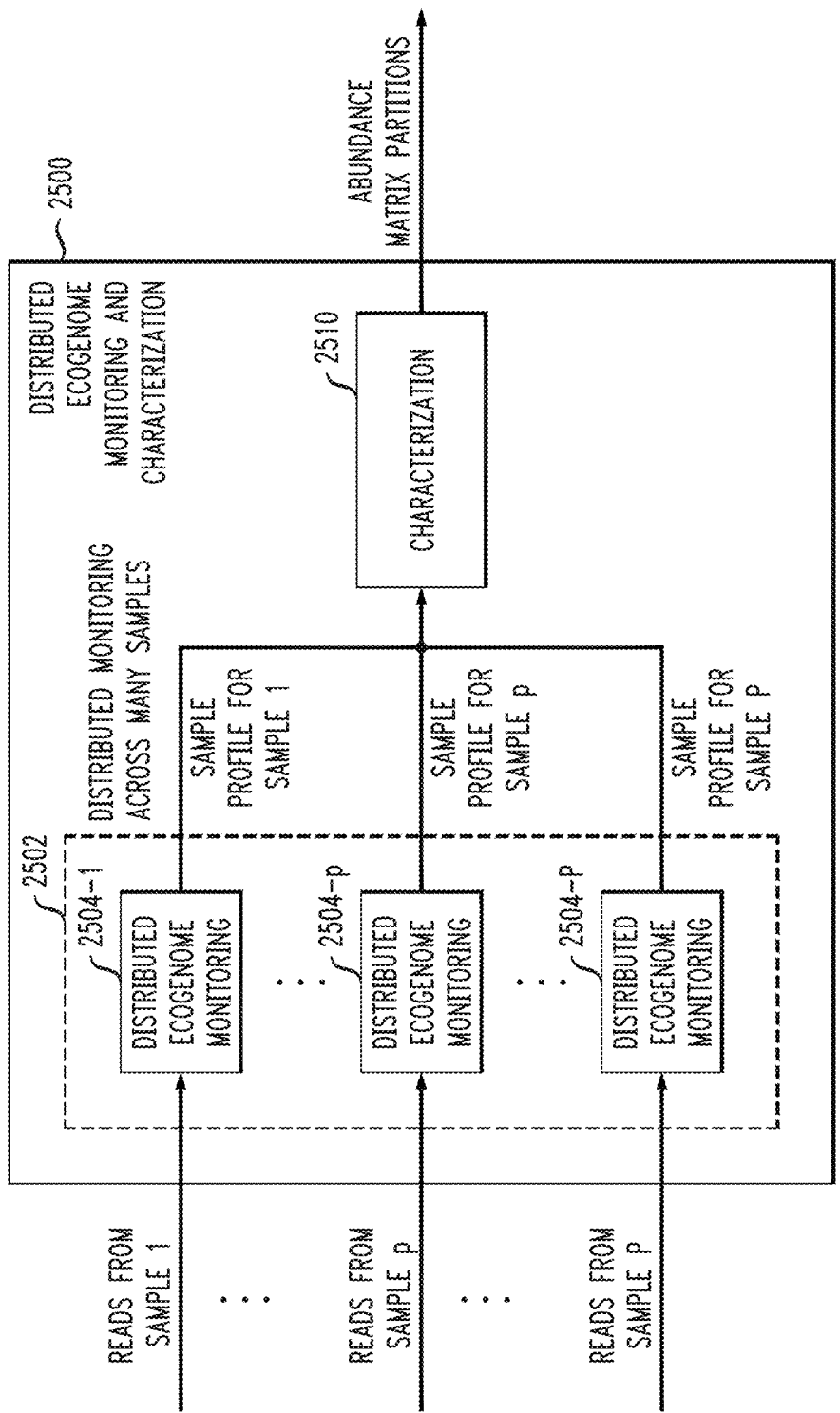
FIG. 25 shows another illustrative embodiment of distributed ecogenomic monitoring and characterization.

Referring initially to FIG. 25, a distributed ecogenome monitoring and characterization block 2500 comprises a distributed monitoring component 2502 providing distributed monitoring across many samples. The distributed monitoring component 2502 includes individual distributed ecogenome monitoring blocks denoted 2504-1, . . . 2504-$p$, . . . 2504-P, configured to process reads from respective samples denoted Sample 1, . . . Sample $p$, . . . Sample P in order to generate respective sample profiles denoted Sample Profile 1, . . . Sample Profile $p$, . . . Sample Profile P. These sample profiles are applied to a characterization block 2510 to generate abundance matrix partitions of the type described elsewhere herein.

It should be noted that the characterization block 2510 of the distributed ecogenome monitoring and characterization of the type illustrated in FIG. 25 can be triggered in a wide variety of different ways. For example, the characterization can be triggered by an automated determination that a set of samples has certain designated characteristics in common or that the samples are from patients experiencing similar symptoms or other characteristics such as location. It is also possible that a clinician, researcher or other user may simply decide to explore the existence or absence of certain characteristics in a set of samples utilizing the surveillance functionality disclosed herein.

Figure 26:
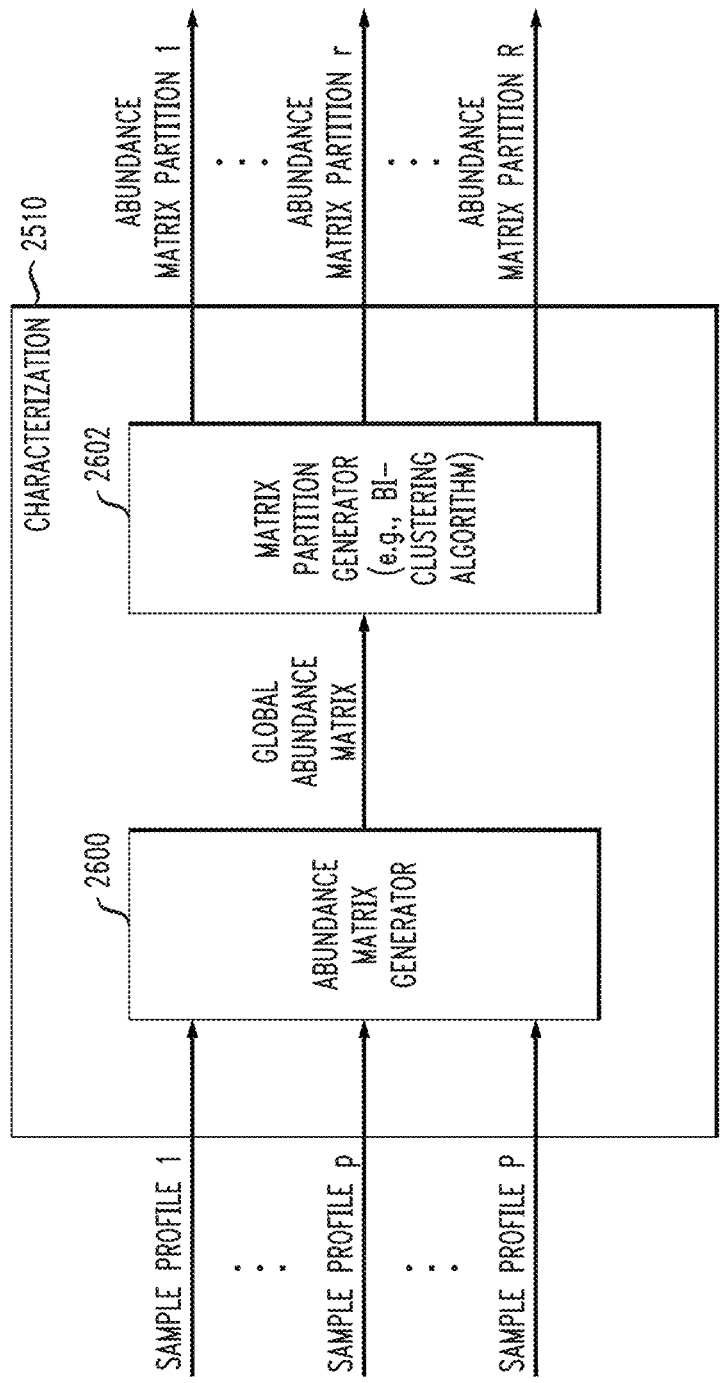
FIG. 26 shows a more detailed view of a characterization portion of the FIG. 25 embodiment.

FIG. 26 shows a more detailed view of the characterization block 2510. In this embodiment, the characterization block 2510 more particularly comprises an abundance matrix generator 2600 that receives as its inputs the sample profiles denoted Sample Profile 1, . . . Sample Profile $p$, . . . Sample Profile P. These are processed in the abundance matrix generator 2600 to generate a global abundance matrix that is applied to a matrix partition generator 2602 that illustratively implements a biclustering algorithm, although other types of matrix partitioning algorithms can be used in other embodiments. For example, alternative matrix partitioning algorithms implemented in other embodiments can be include any of a number of known matrix subgrouping algorithms. The matrix partition generator 2602 generates as its outputs a set of abundance matrix partitions denoted Abundance Matrix Partition 1, . . . Abundance Matrix Partition r, . . . Abundance Matrix Partition R.

Figure 27:
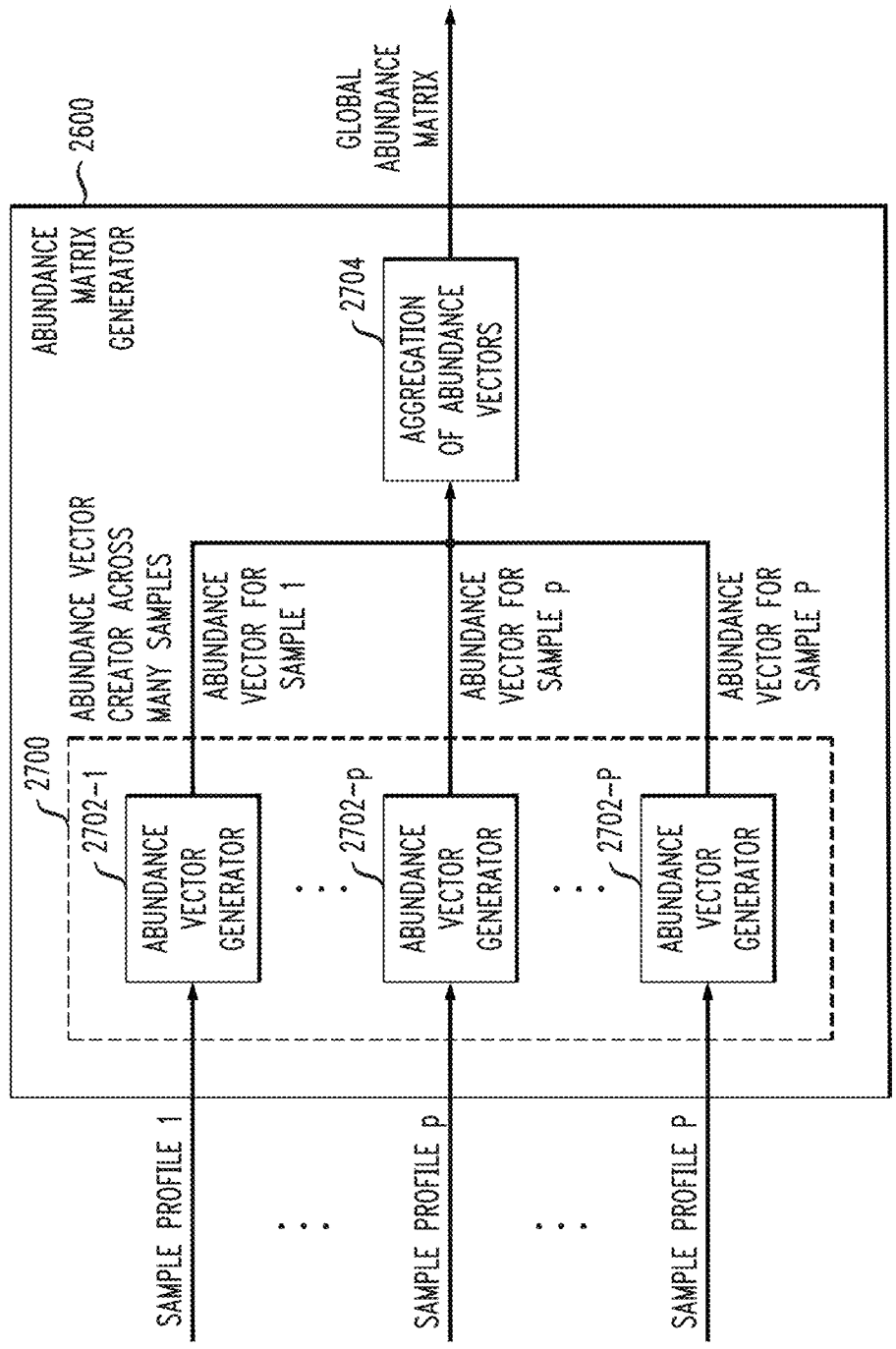
FIG. 27 shows a more detailed view of an abundance matrix generator of FIG. 26.

The abundance matrix generator 2600 of FIG. 26 is shown in a more detailed view in FIG. 27. In this embodiment, the abundance matrix generator comprises an abundance vector generator component 2700 operating across many samples. The abundance vector generator component 2700 comprises individual abundance vector generators 2702-1, . . . , 2702-$p$, . . . 2702-P, configured to process respective ones of the sample profiles Sample Profile 1, . . . Sample Profile p, . . . Sample Profile P in order to generate respective abundance vectors as illustrated. These abundance vectors are applied to an aggregation block 2704 that combines the abundance vectors to form the global abundance matrix.

The abundance matrix in some embodiments is configured such that the rows of the matrix are respective abundance vectors generated for respective samples, and the columns are respective gene units. In such an arrangement, each entry [i,j] of the abundance matrix represents how abundant gene unit j was in sample i. For an embodiment with N abundance vectors and M gene units, the abundance matrix is an N×M matrix. Alternative types and arrangements of abundance matrices can be used in other embodiments. For example, in other embodiments, the abundance vectors can be respective columns of the matrix and the gene units can be respective rows of the matrix. FIG. 26 illustrates that a biclustering algorithm or other type of matrix partitioning operation is applied to the abundance matrix in conjunction with the characterization of a disease, infection or contamination.

Figure 28:
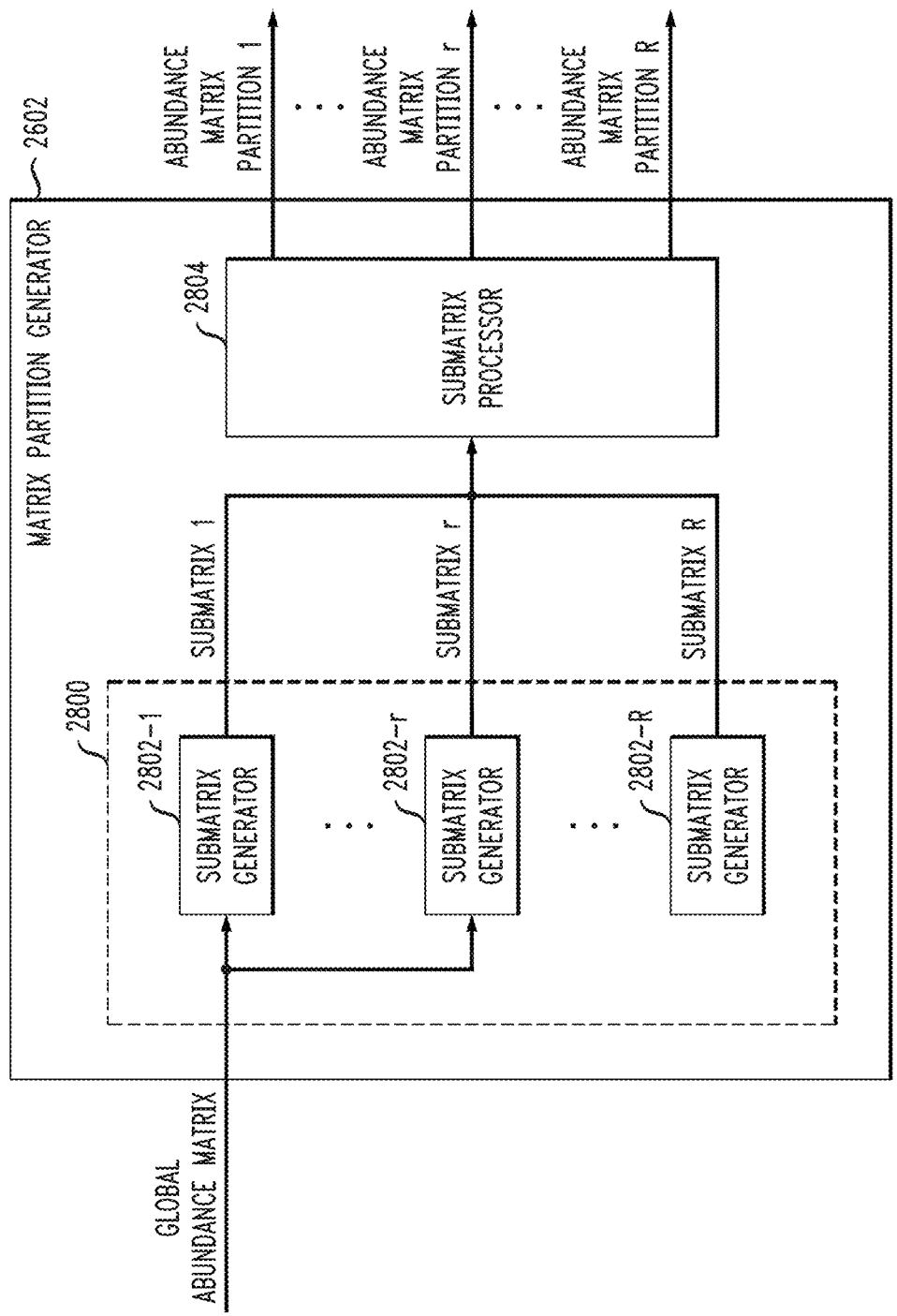
FIG. 28 shows a more detailed view of a matrix partition generator of FIG. 26.

The matrix partition generator 2602 of FIG. 26 is shown in a more detailed view in FIG. 28. In this embodiment, the matrix partition generator 2602 comprises a submatrix generator component 2800 that includes individual submatrix generators 2802-1, . . . 2802-$r$, . . . 2802-R, each configured to process the global abundance matrix from the abundance matrix generator 2600. The matrix partition generator 2602 further comprises a submatrix processor 2804 which processes the submatrices to provide the corresponding output abundance matrix partitions denoted Abundance Matrix Partition 1, . . . Abundance Matrix Partition r, . . . Abundance Matrix Partition R.

In some embodiments, the submatrix processor 2804 comprises an outbreak module generator and the abundance matrix partitions comprise respective outbreak modules. Each abundance matrix partition in such an embodiment illustratively comprises a submatrix (S',G') where S' denotes a subset of the samples and G' denotes a subset of the gene units. For example, such a submatrix illustratively represents a group of diseased patients that share the common denominator G' denoting the gene units of a corresponding disease. The common denominator G' is an example of what is referred to herein as an outbreak module and may be stored for future computations and comparison. Each characterization event on an abundance matrix can produce multiple outbreak modules.

An outbreak module score may be attached by the submatrix processor 2804 to the corresponding submatrix, with the attached score representing the statistical significance of that submatrix among all possible submatrices. Based on S' an outbreak participants module can be generated, illustratively comprising a vector of all samples in the outbreak module having the attached score. A similar vector may be created based on the outbreak module G' to denote the possible genetic composition of the outbreak.

Other types and configurations of outbreak modules and participants modules can be used in other embodiments.

In conjunction with the characterization process, various reports can be generated by the submatrix processor 2804 and possibly presented to a client via a GUI of the system. Such reports can illustrate the abundance matrix partitions resulting from the biclustering algorithm or other type of abundance matrix partitioning algorithm. For example, a heat map can be generated in which the matrix entries are represented by colors with the color of each matrix entry being consistent with the corresponding abundance value of that entry so as to highlight the partitioned submatrices and their associated participants module and outbreak module. Additionally or alternatively, the participants module can be projected on a map displayed within the GUI, showing where the diseased patients are located.

As mentioned previously, certain designated alignment histogram characteristics such as depth can be used as the abundance measure utilized in generating the abundance vectors. Numerous other types and arrangements of information derived from the alignment histograms, including one or more of depth, coverage and integral, as well as additional or alternative metrics not necessarily based on alignment histograms, can also be used to generate abundance vectors utilizing the techniques disclosed herein.

FIG. 29 shows an example of a BED file utilized in conjunction with the read mapping and histogram generation processes described above. As mentioned previously, the BED file illustratively represents an output of the Cloud Burst mapping algorithm used in the read mapping block 2116 of FIGS. 21 and 22, and an input to the abundance vector generator. Each line in the BED file represents a hit of a particular read from the sample on one of the gene units in the gene unit database. For example, as illustrated, the BED file in this embodiment includes a reference gene unit identifier, a starting offset in the reference, an ending offset in the reference, a read number, and an indication of the number of mismatches in the alignment. This particular read mapping file format is presented by way of example only, and numerous other formats can be used in other embodiments.

As mentioned previously, some embodiments implement surveillance functionality utilizing a combination of distributed ecogenome monitoring and characterization with distributed epidemiological interpretation. The illustrative embodiment of FIG. 4 is an example of such an arrangement.

In these and other embodiments involving distributed epidemiological interpretation, transmission trees may be used.

Figure 30:
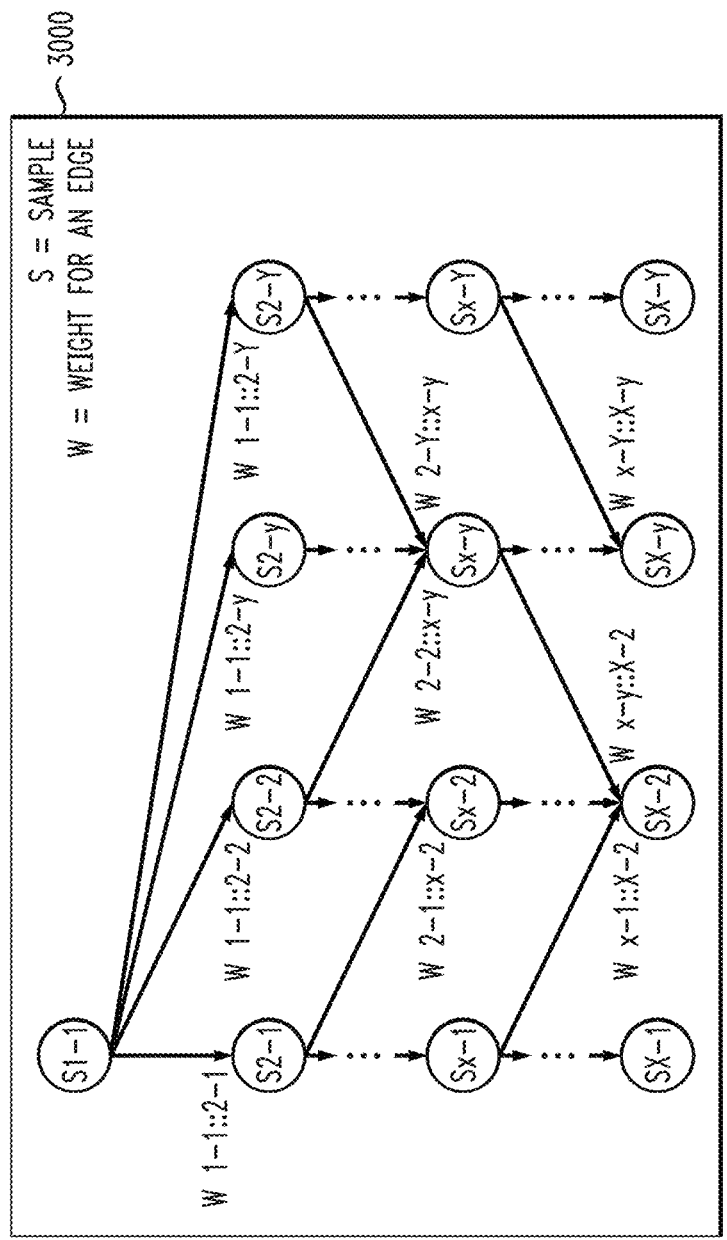
FIG. 30 shows an example of one type of graph for use in conjunction with distributed epidemiological interpretation in an illustrative embodiment.

FIG. 30 shows a transmission graph 3000 for use in conjunction with distributed epidemiological interpretation in an illustrative embodiment. Such a graph may be utilized, for example, in block 420 of the FIG. 4 embodiment, or in other embodiments involving utilization of an epidemiologic comparison component.

The transmission graph 3000 is an example of what is more generally referred to herein as an "epidemiological graph." In the embodiment illustrated, each node of the transmission graph 3000 corresponds to a different biological sample ("S") and a directed edge from one node to another node within the transmission graph is indicative of an epidemiological relationship between those two nodes. For example, a directed edge from one node to another node may be an indication of infection. The directed edges are illustratively weighted using respective weights ("W") that further characterize the strength of the relationship between the corresponding pair of nodes within the transmission graph. The weights are also referred to as respective sample-to-sample comparison scores.

A transmission graph of the type illustrated in FIG. 30 can be used to provide a wide variety of different types of surveillance functionality. For example, such a graph can be utilized to characterize spread of a disease, infection or contamination, and to support functions such as identification of impacted communities via contact tracing, computation of hubs and super-spreaders, generation of outbreak spread predictions, generation of risk ranking decisions, and many others.

In some embodiments, a transmission graph such as transmission graph 3000 represents an example of a global epidemiological graph generated utilizing a plurality of local epidemiological graphs provided by different sequencing centers. Such a global epidemiological graph can be used to provide global view information to a client as previously described in conjunction with the embodiment of FIG. 5.

Other types of graphs can be used in a given embodiment. For example, a global epidemiological graph in some embodiments may alternatively comprise a phylogenic tree in which the biological samples correspond to respective leaf nodes that are hierarchically clustered within the phylogenic graph. As mentioned previously, the term "graph" as used herein is intended to be broadly construed.

Additional examples of graphs that can be used in illustrative embodiments include directed acyclic graphs, also referred to as phylogenic networks. For example, such a graph can be used to model the evolution of a "super clone" outbreak via horizontal transfer of virulent gene units. The phylogenic network allows both horizontal and vertical transfer of gene units to be effectively modeled. It should be noted that trees referred to in certain illustrative embodiments herein can in other embodiments be replaced with phylogenic networks or other types of network or graph arrangements. For example, outbreak trees can in other embodiments be replaced with outbreak networks.

Transmission trees, phylogenic trees and other similar tree, network or graph structures referred to herein are illustratively utilized in conjunction with provision of analytics processing or other types of surveillance functionality within a given system. For example, the surveillance functionality may be configured to provide topological queries on a global epidemiological graph formed using multiple local epidemiological graphs provided by respective geographically-distributed sequencing centers.

Each individual sequencing center in such an arrangement generally has only limited visibility of the global epidemiological graph. For example, a given sequencing center may only have a view of respective local portions of the graph relating to gene units in its local gene unit database. However, as noted above, global view information comprising substantially the entire global epidemiological graph can be provided as part of the surveillance functionality offered to a client. Such arrangements can be configured in some embodiments to protect the privacy of the sequencing centers in at least portions of the local information utilized in generating their respective local graphs.

As mentioned previously, some embodiments are configured to implement reasoning and other types of functionality utilizing one or more data models.

Data models of the type described herein are well suited for use in disease monitoring, investigation and characterization. For example, such data models are generic, implementation independent, and accommodate genome plasticity. Moreover, such data models are valid for both known and unknown diseases. This illustratively includes mosaic diseases that can be characterized as a collection or composition of genome segments from microbial genomes observed in the past.

References herein to use of data models to monitor, investigate and characterize diseases should be understood to be similarly applicable to monitoring, investigation and characterization of infections and contaminations, as well as other similar conditions.

When analyzing a given sample, the detection of some of the components present in previously-identified known diseases is an indication of potential presence of that disease in the sample.

Accordingly, a given disease can be modeled based on its genome or pan-genome composition. Such a pan-genome can illustratively comprise a combination of core genomes, which could be multiple species or strains, and units of accessory genes that are horizontally co-transferred such as plasmids, phages, pathogenicity islands, and integrons. In some cases, the combination becomes virulent or more successful. Also, accessory genes can be horizontally transferred across different strains of the same species.

Illustrative embodiments disclosed herein utilize metagenomics for disease characterization, where a disease is represented as a composition of genomes or pan-genomes. Such a composition can be viewed as a particular subset of a metagenomics ecosystem that leads to a particular disease. As indicated elsewhere herein, a given metagenome may refer to the genomic contents of an entire microbial community. Metagenomics often involves the processing of genetic material recovered directly from environmental samples, although other arrangements are possible.

The implementation-independent data models disclose herein can be used on any metagenomics processing framework and as indicated above can be used to model both known and unknown diseases. For example, such data models can be used for reasoning on, analyzing and dynamically classifying diseases as they emerge, through genome plasticity.

As a more particular example, data models disclosed herein can be used to model polymicrobial diseases, caused by combinations of viruses, bacteria, fungi and parasites. In these diseases, the presence of one microorganism generates a niche for other pathogenic microorganisms to colonize. For example, one microorganism may predispose the host to colonization by other microorganisms, or two or more non-pathogenic microorganisms may together cause a particular disease. The data models disclosed herein can similarly be used to characterize vector-borne diseases. For example, a single bite from a tick can lead to a polymicrobial disease.

Also, the disclosed data models are applicable to microbial interference, or the polymicrobial inverse effect. In microbial interference, pathogens or probiotic microorganisms generate a niche or occupy sites in the host that suppresses the colonization of other microorganisms. Examples include both viruses and bacteria, such as the ability of *Streptococcus pneumonia* carriage to protect against *Staphylococcus aureus* carriage, and the inverse effect of pneumococcal conjugate vaccination on the increased carriage of staph *aureus* and staph-*aureus*-related disease.

Examples of data models of the type mentioned above will now be described with reference to FIGS. 31 through 78. It is to be appreciated, however, that a wide variety of additional or alternative data models can be used in other embodiments.

Figure 31:
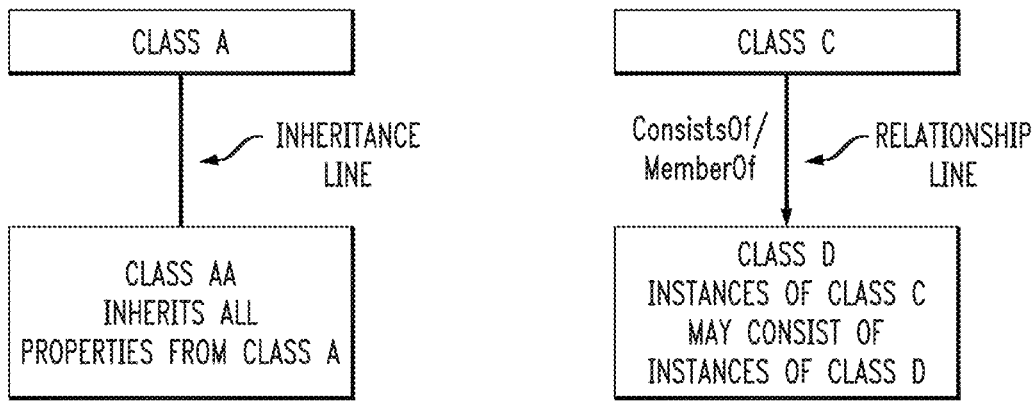
FIGS. 31 through 78 show examples of different aspects of data models utilized in illustrative embodiments.

Referring initially to FIG. 31, symbol conventions utilized for classes in the example data models are defined. For example, as shown, Class A and Class AA are connected by an inheritance line, which indicates that Class AA inherits all properties from Class A. Also, Class C is connected to Class D by a ConsistsOf/MemberOf relationship line, which indicates that instances of Class C may consist of instances of Class D.

Figure 32:
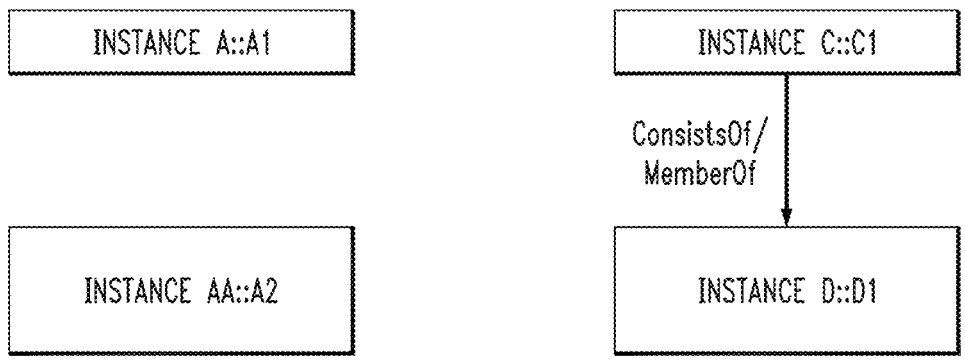

FIG. 32 defines symbol conventions utilized for instances in the data models. For example, instances of Class A and Class AA are denoted as A::A1 and AA::A2, respectively. Similarly, instances of Class C and Class D are denoted as C::C1 and D::D1, respectively.

Figure 33:
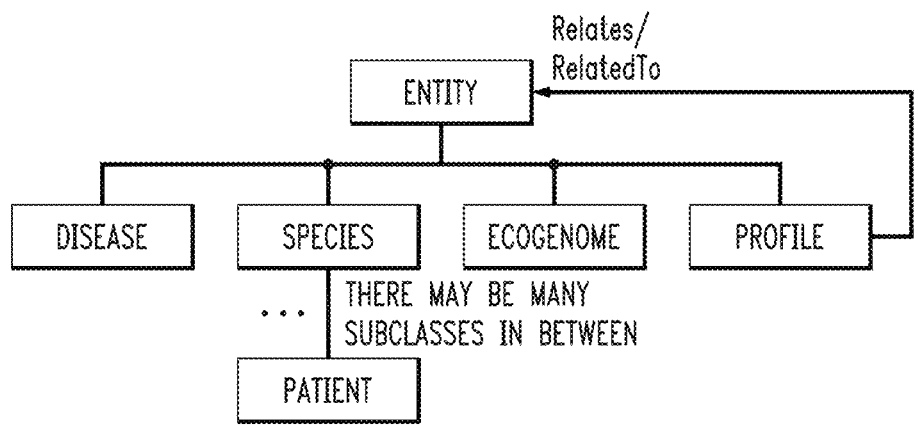

FIG. 33 illustrates how a given entity in a data model can relate to a disease, species, ecogenome and profile. The entity relates to a patient in this example via the species, although there may be many subclasses between the species and the patient. The entity, disease, species, ecogenome and profile in the FIG. 33 data model may be viewed as respective examples of what are more generally referred to herein as "elements" of a given data model. A wide variety of other types of elements can be used.

Figures 34, 35:
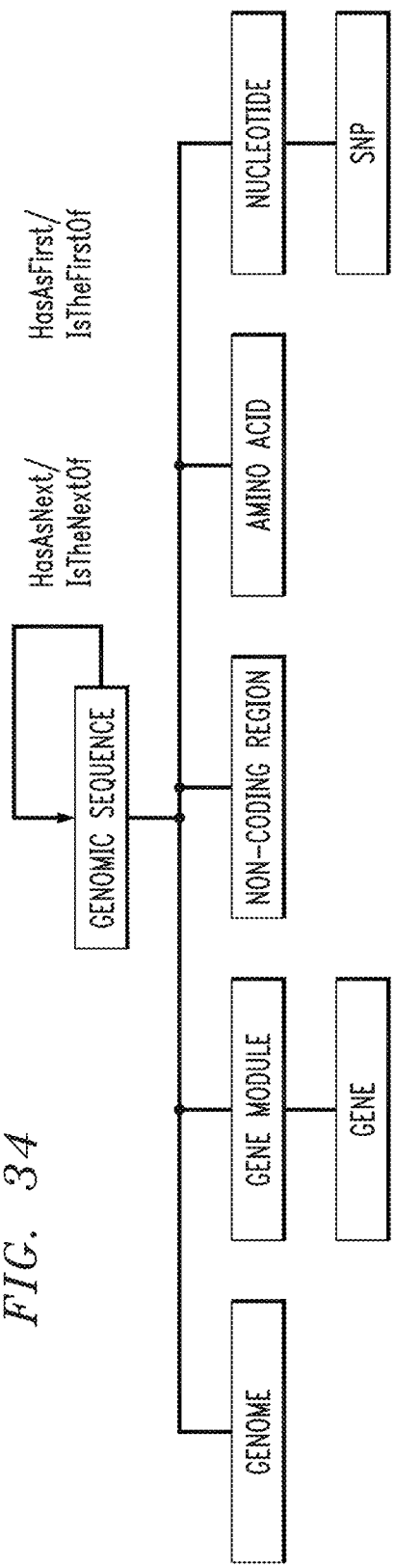
Figure 36:
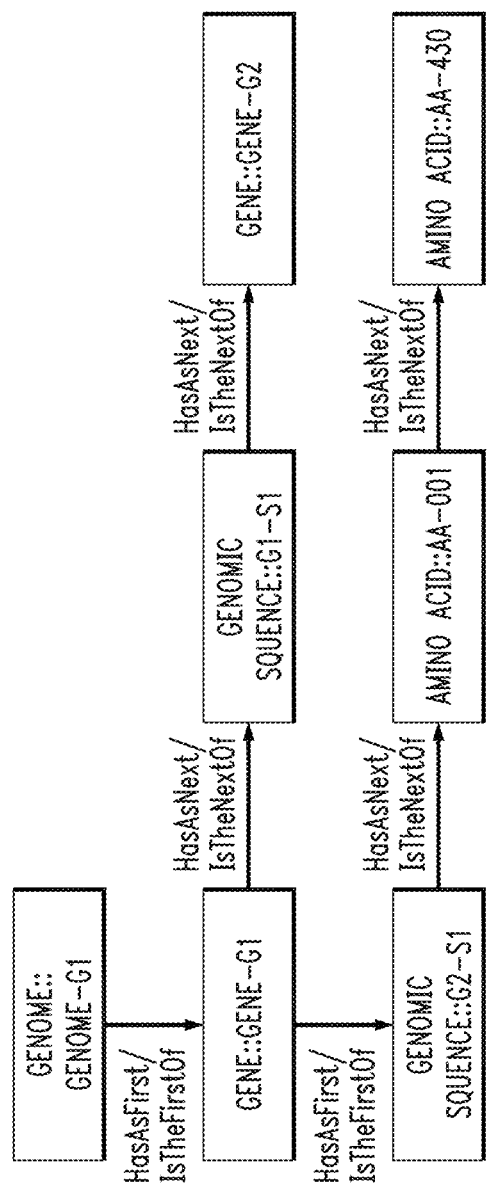

FIGS. 34 through 36 illustrate data models for genes and genomes. For example, with reference to FIG. 34, a model of a gene is shown. FIG. 35 shows an example topology for a particular gene using that gene model, and FIG. 36 shows an example topology for a genome using that gene model.

Figure 37:
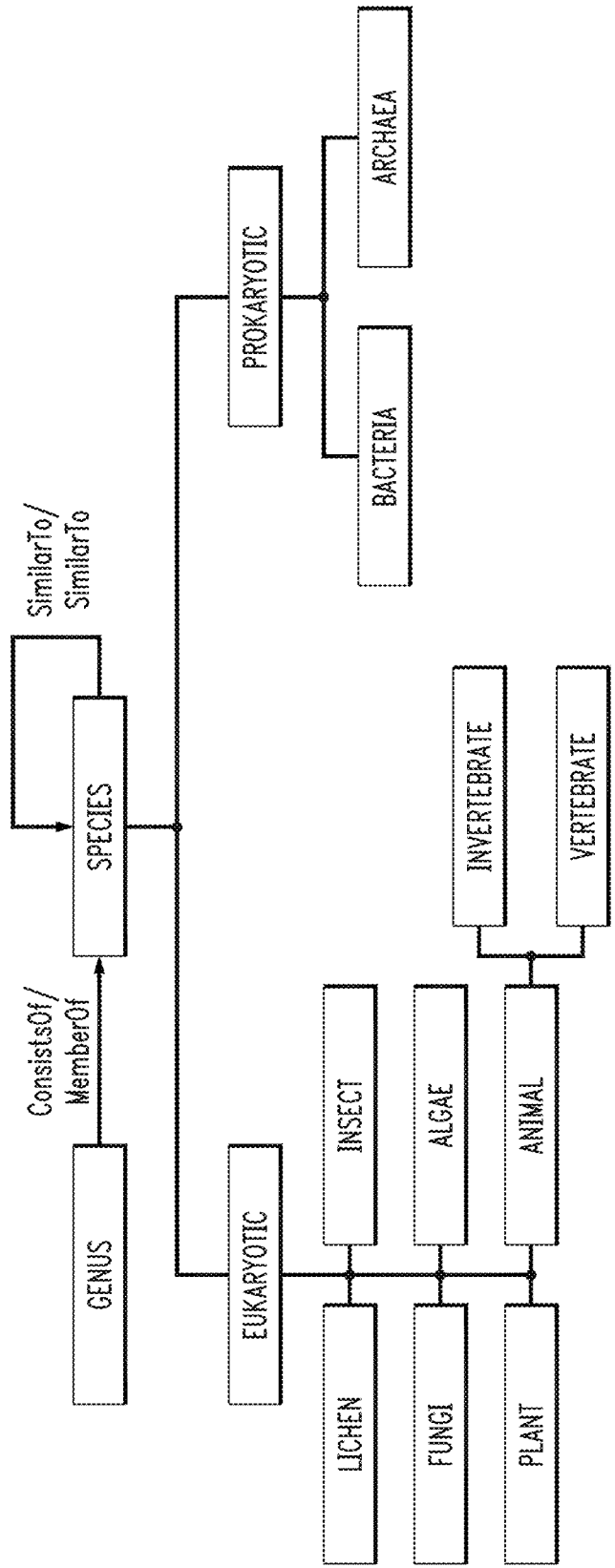
Figure 38:
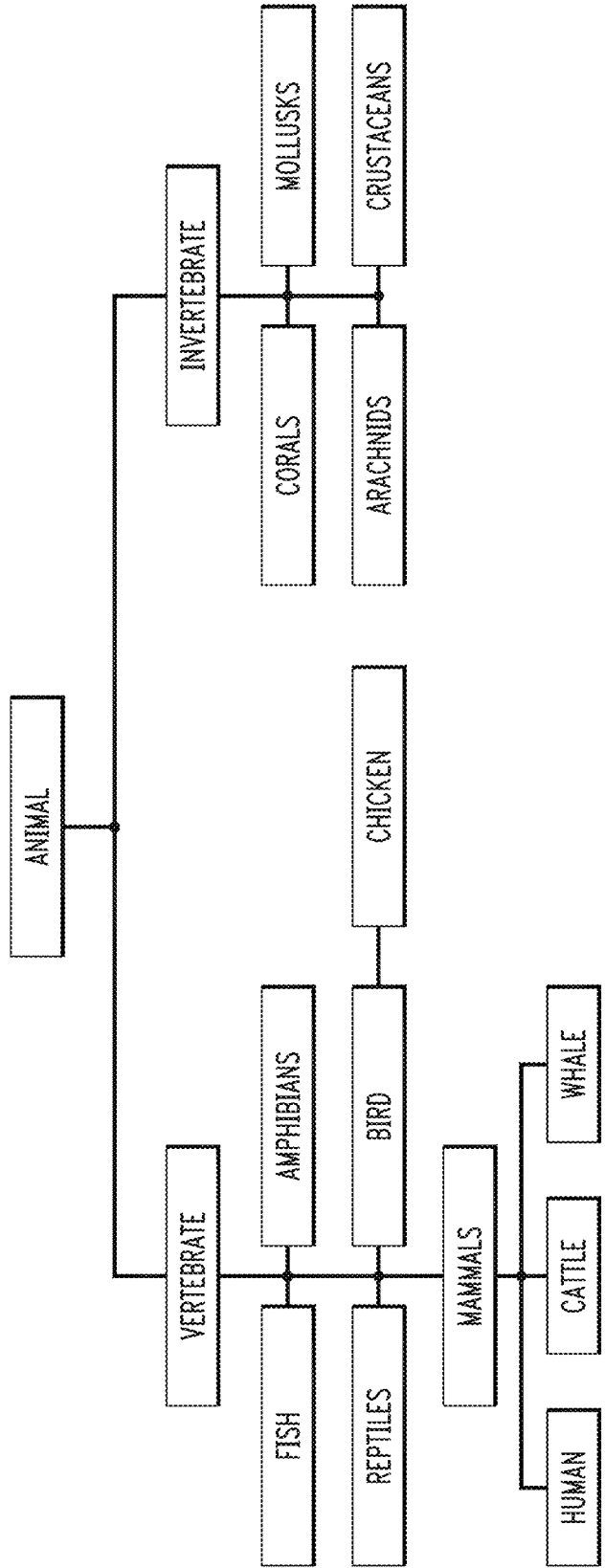
Figure 39:
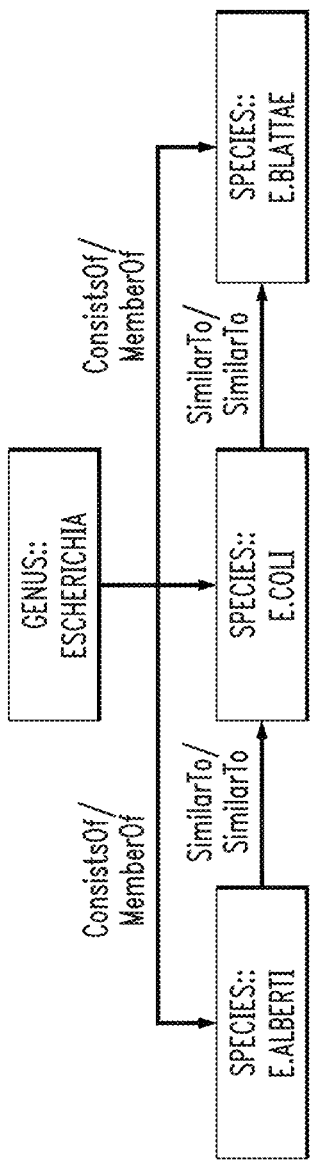

FIG. 37 shows an example data model for genus and species. It is assumed for this example that a species refers to a group of living organisms consisting of similar individuals capable of exchanging genes or interbreeding. The species is the principal natural taxonomic unit, ranking below a genus and typically denoted by a Latin binomial, e.g., *Homo sapiens*. FIG. 38 shows an example data model for animals. FIG. 39 shows an example data model for the genus *Escherichia*, which includes the species *E. alberti, E. coli* and *E. blattae*.

Figure 40:
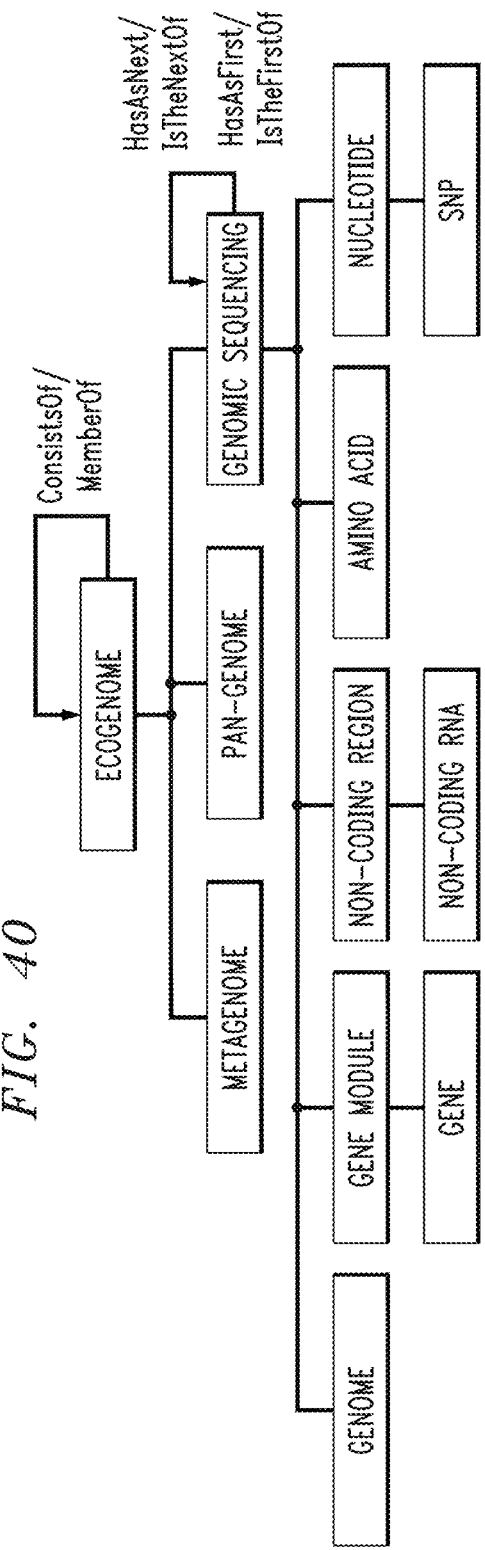

FIG. 40 shows an example data model for an ecogenome. An ecogenome in this embodiment illustratively refers to an ecosystem or portion of an ecosystem that comprises a collection of genomes, pan-genomes and/or metagenomes, although other arrangements are possible. It should also be noted that an ecogenome may comprise one or more other ecogenomes. Also, a given pan-genome may comprise one or more other pan-genomes, and a given pan-genome may itself comprise one or more other ecogenomes.

Figure 41:
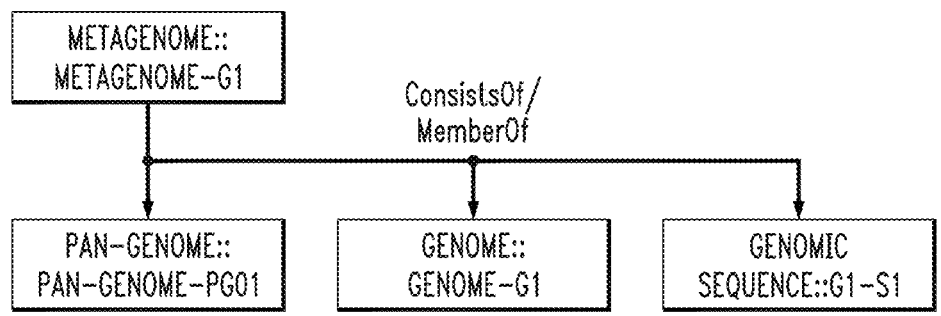

FIG. 41 shows an example topology for an ecogenome based on a portion of the data model of FIG. 40. The ecogenome in this example topology illustratively comprises a metagenome that includes a pan-genome, a genome and a genomic sequence.

Figure 42:
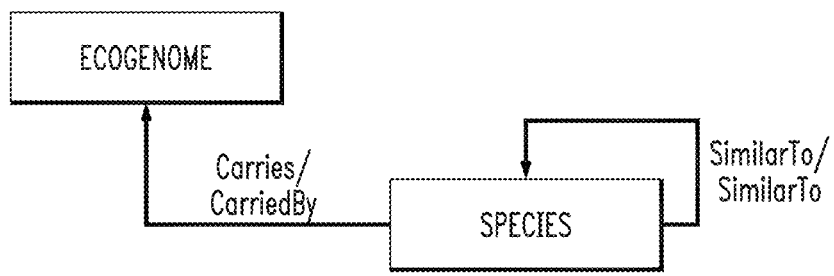
Figure 43:
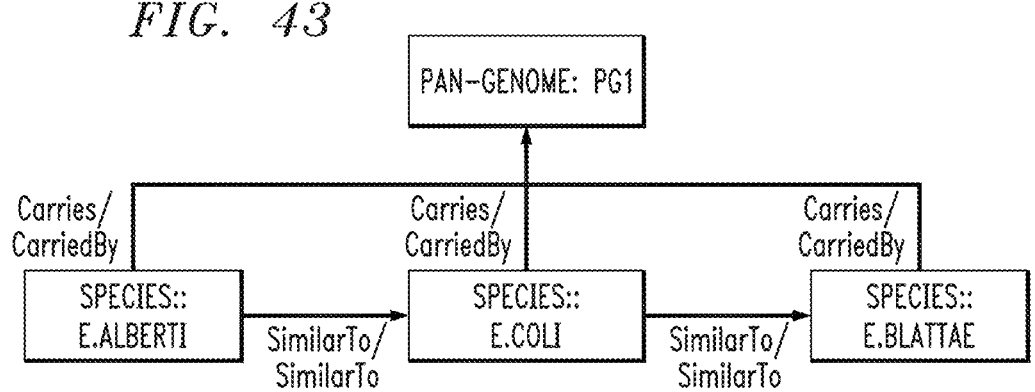

FIG. 42 illustrates a data model relating an ecogenome to a species, and FIG. 43 shows an example topology of an ecogenome comprising a pan-genome and having multiple related species, based on the ecogenome data model of FIG. 42.

Figure 44:
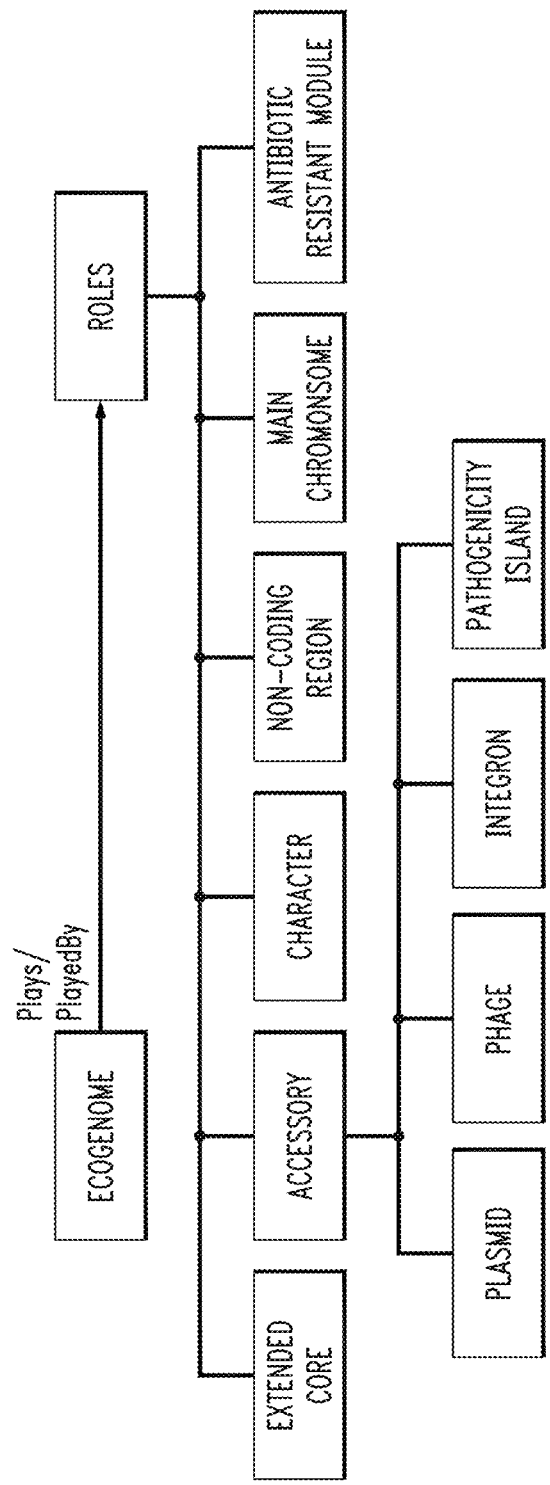
Figure 45:
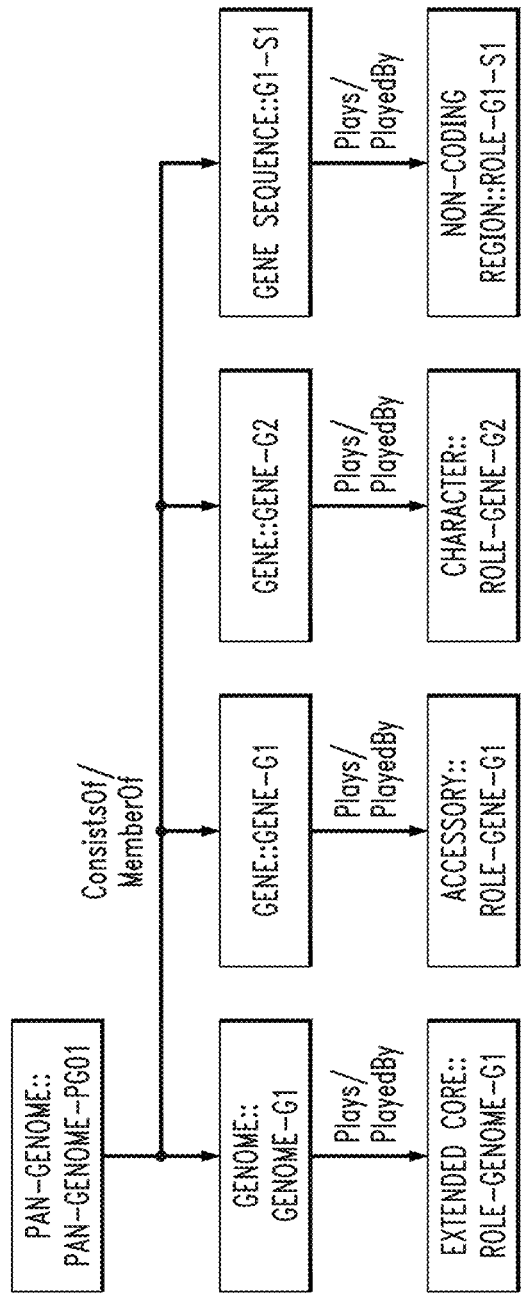

Different ecogenomes can play different types of roles, as illustrated by the data model of FIG. 44. For example, different roles of this type are a source of genetic variability in bacterial populations. A corresponding example topology for this data model is shown in FIG. 45.

Figure 46:
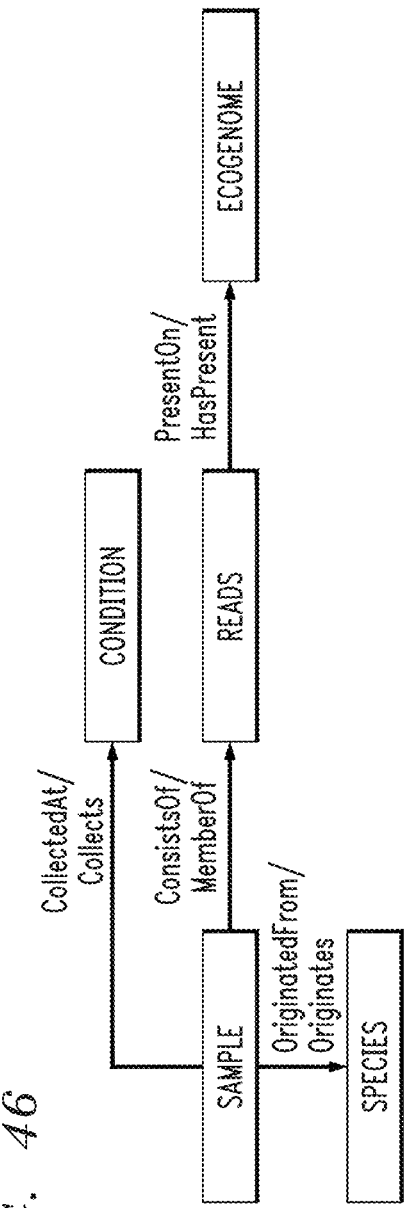
Figure 47:
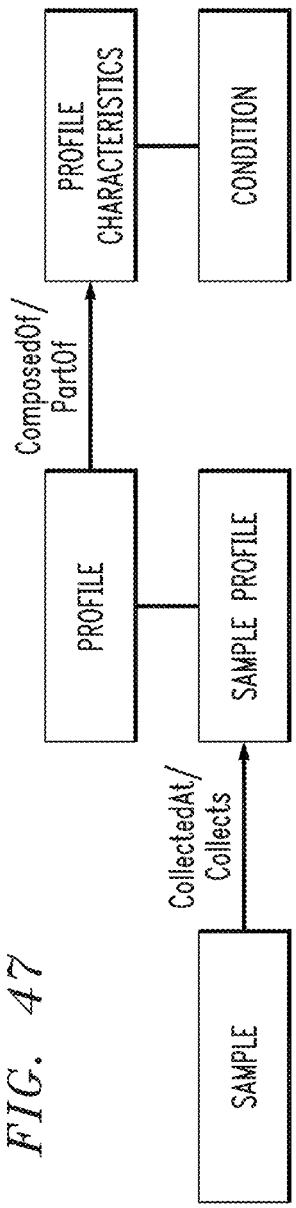
Figure 48:
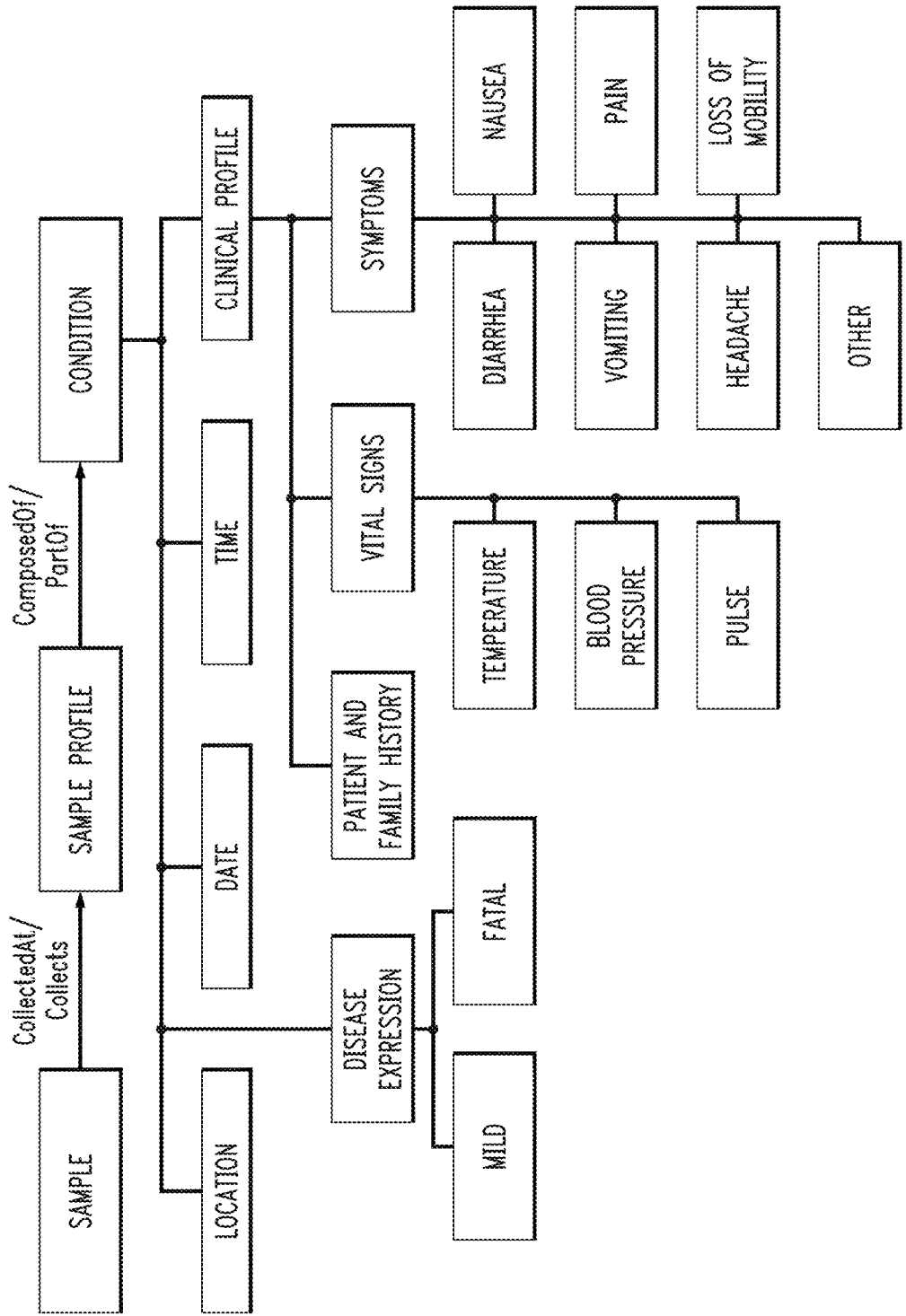
Figure 49:
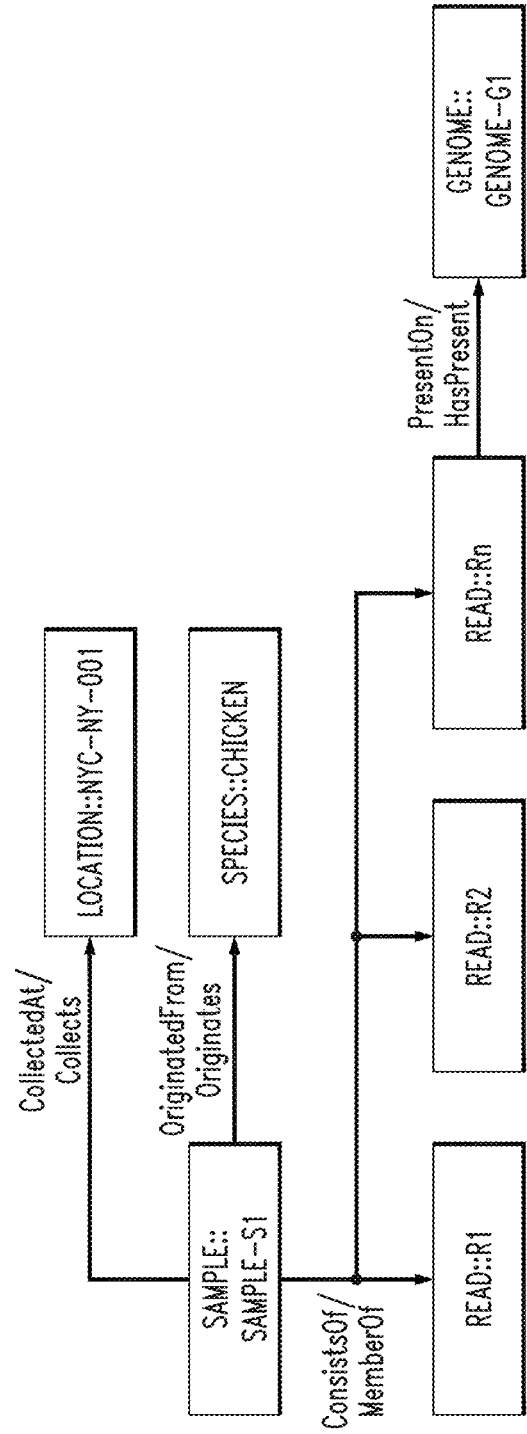

FIG. 46 illustrates a data model for samples, reads and genomes. A related data model for samples and profiles, capturing related non-genomic information, is illustrated in FIG. 47. FIG. 48 shows an example data model for a condition, also illustratively capturing related non-genomic information. An example topology for samples, reads and genomes based on the FIG. 46 data model is shown in FIG. 49.

Figure 50:
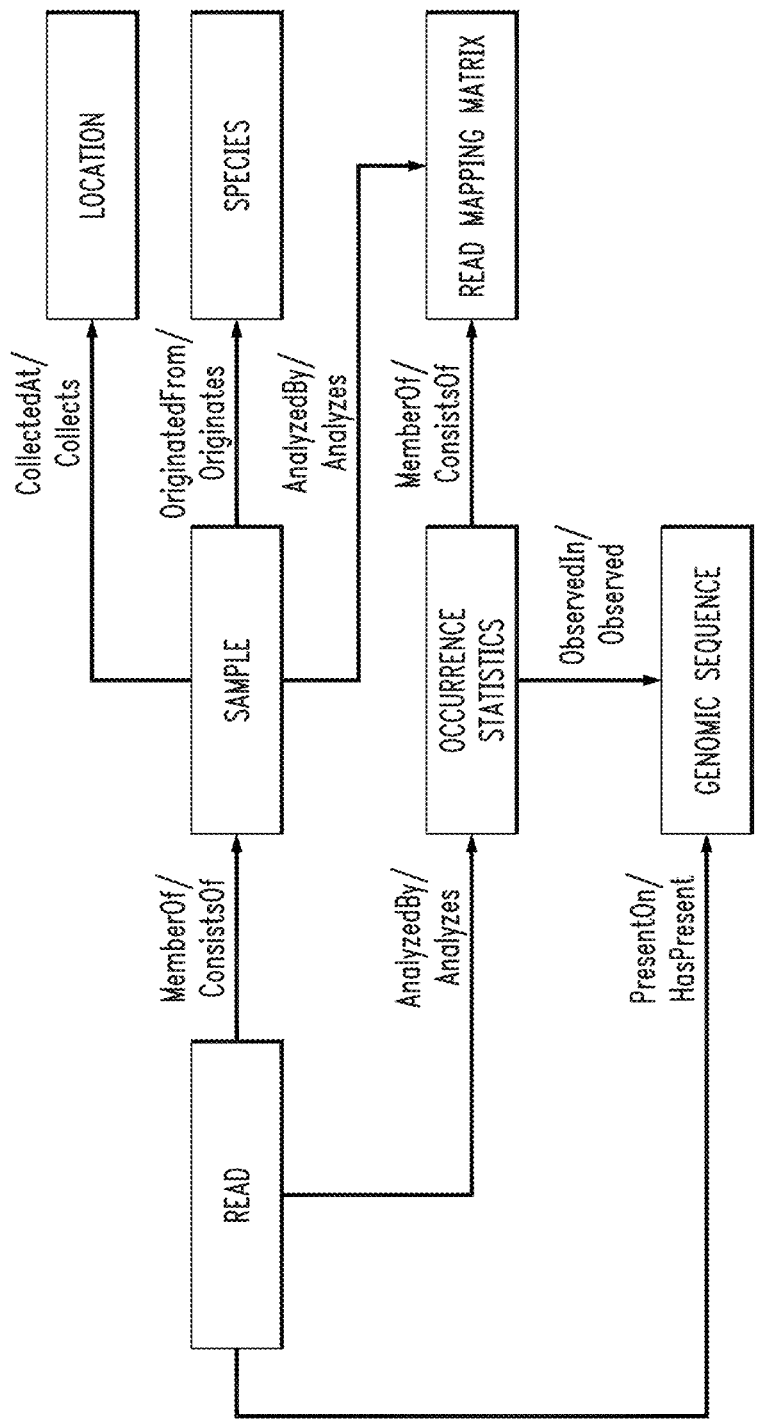

FIG. 50 shows an example of a data model for modeling read occurrences using a read mapping matrix. It can be seen that there is a relationship between a sample and a read mapping matrix. For example, while the read mapping matrix illustratively maintains statistical information for each read, the sample may include an abundance score for the entire sample, not on a per-read basis.

In some embodiments, there are a number of different types of relationships that are modeled between reads and ecogenomes. For example, under a sampling perspective, indicated by an AnalyzedBy/Analyzes relationship, a determination may be made as to how many times a given read is found in a particular ecogenome, which can be as simple as a genomic sequence. As another example, under a presence perspective, indicated by a PresentOn/HasPresent relationship, when a particular read is found to be part of a genomic sequence, a relationship may be created that directly connects them. Such an arrangement in effect creates a "shortcut" so that deeper analysis can be done across those instances of a particular ecogenome that exhibit the presence of a particular read.

Figure 51:
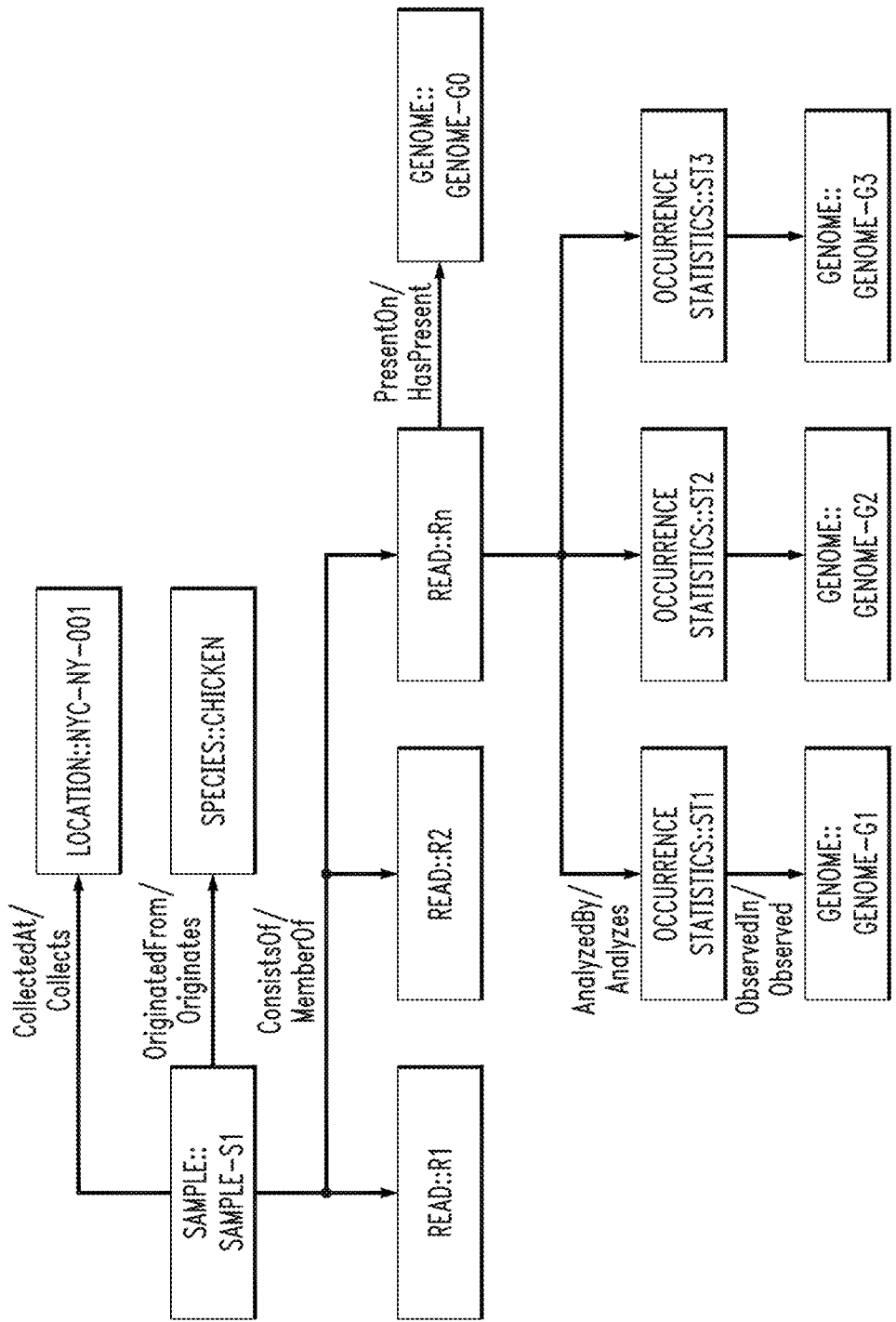

FIG. 51 shows an example of a topology based on the data model of FIG. 50 in which one read relates to multiple distinct genomes. More particularly, read Rn relates to genomes G1, G2 and G3 via respective occurrence statistics ST1, ST2 and ST3, and also has a presence relationship to genome G0.

Figure 52:
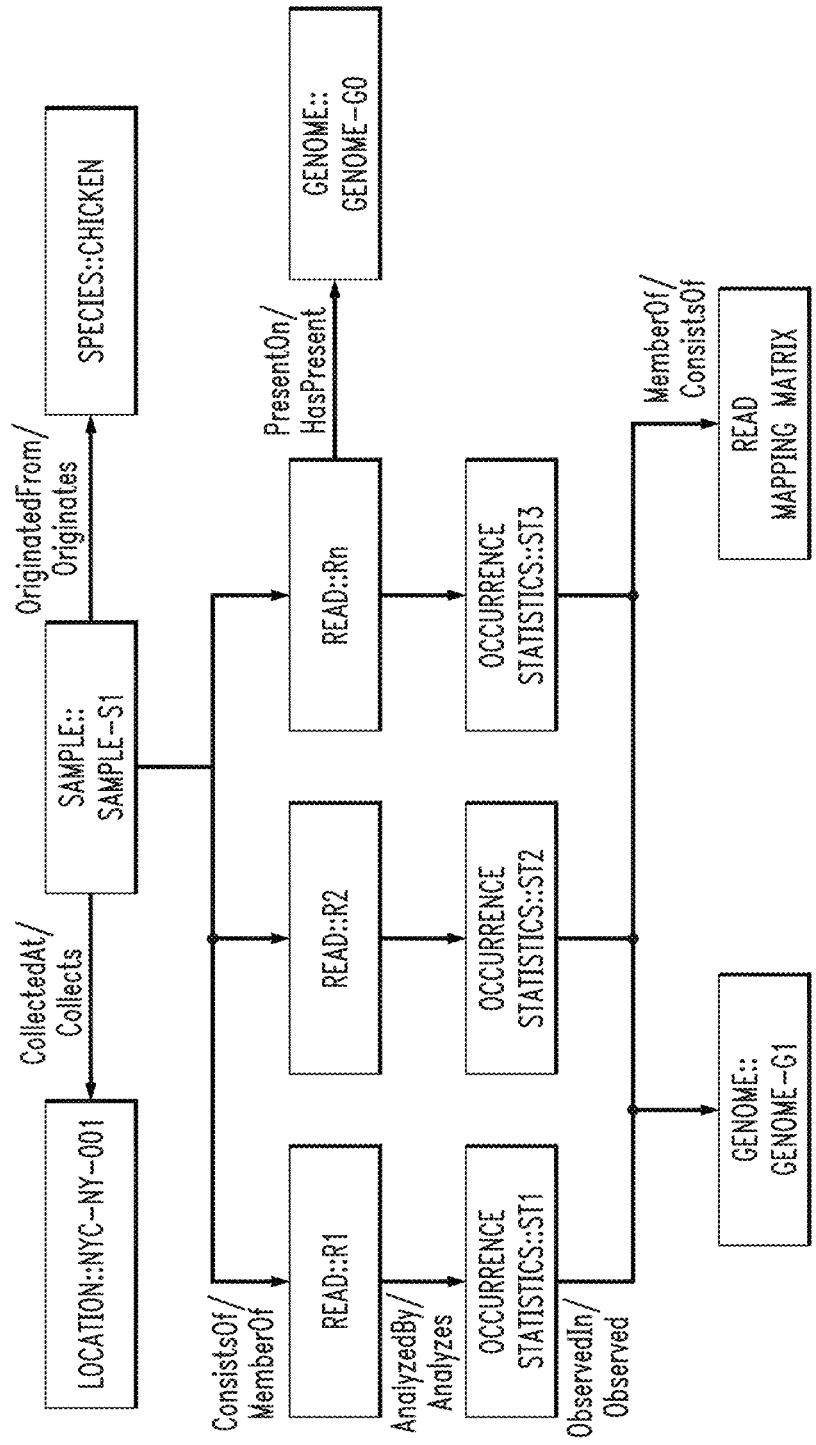

FIG. 52 shows another example of a topology based on the data model of FIG. 50 in which multiple reads relate to a single genome. More particularly, reads R1, R2 and Rn relate to genome G1 via respective occurrence statistics ST1, ST2 and ST3. Also, read Rn has a presence relationship to genome G0.

Figure 53:
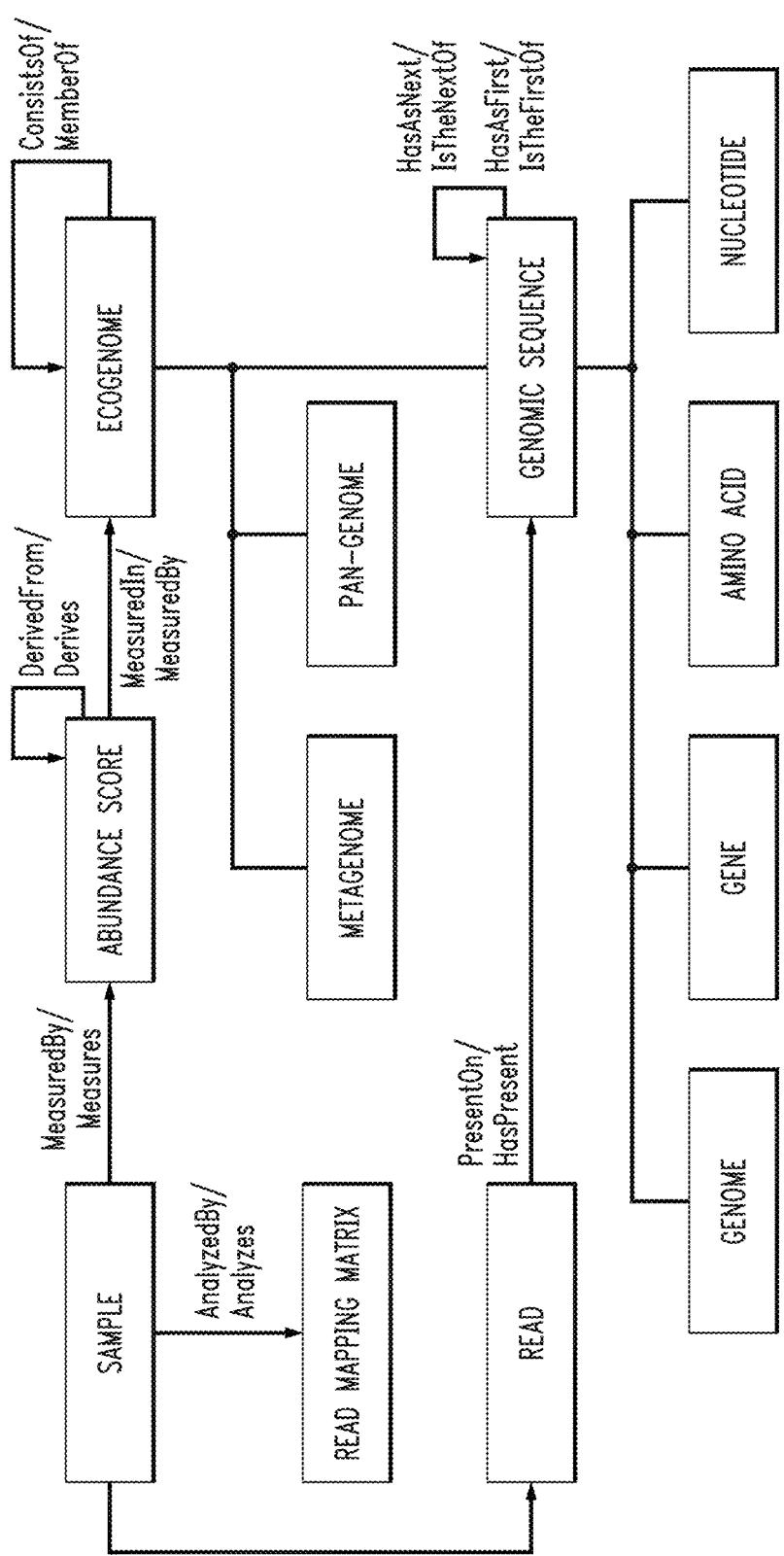
Figure 54:
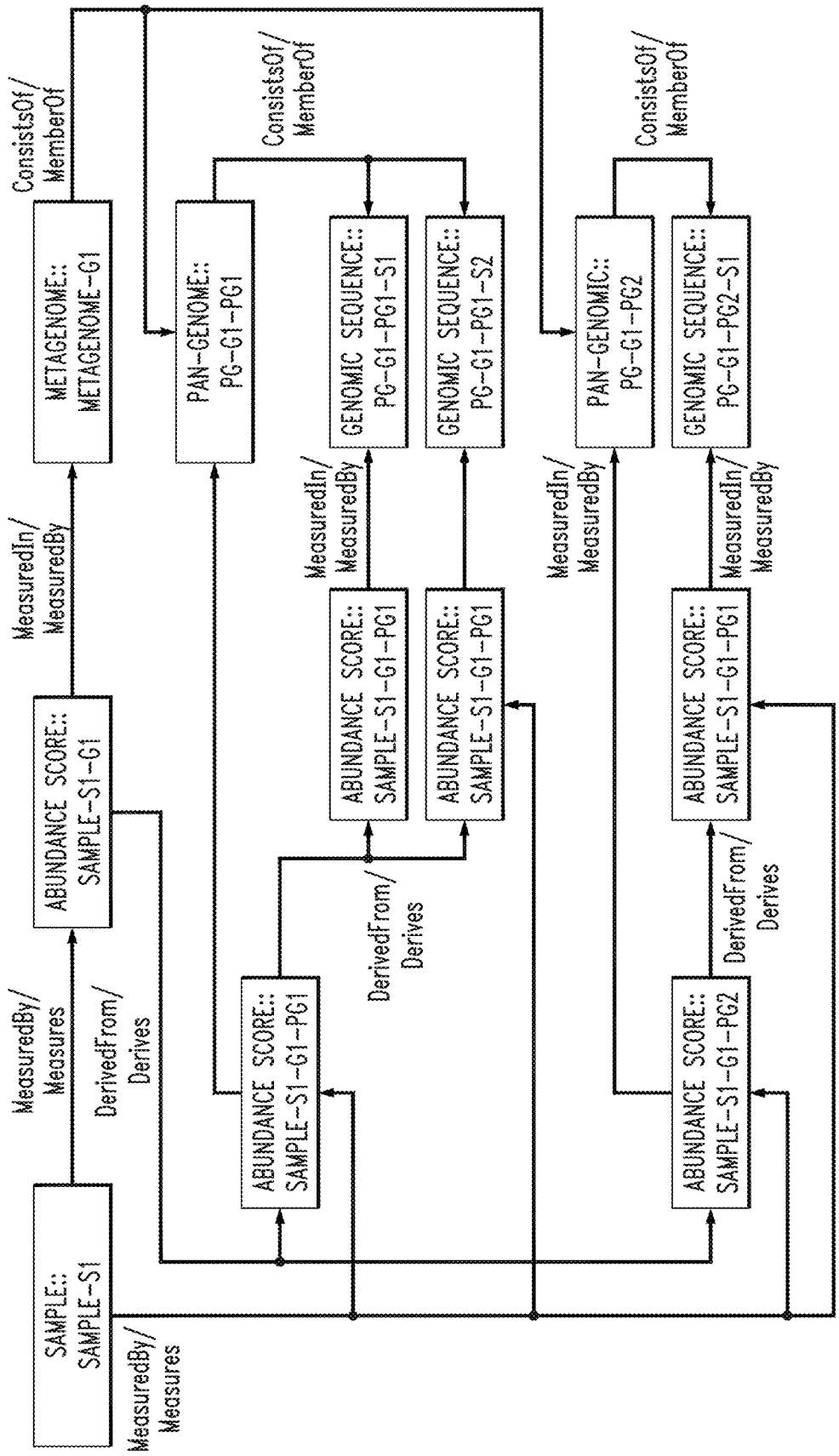

FIG. 53 illustrates a data model for a hit abundance score, also referred to as simply an "abundance score." A given such abundance score illustratively provides a numeric value indicative of the number of occurrences of the reads of a given sample within a particular genomic sequence of an ecogenome. In this model, an abundance score is extended to accommodate different levels of granularity. For example, an abundance score need not be associated with a low level of granularity such as a particular pathogen, but can instead be associated with a higher level of granularity such as an ecogenome, a pan-genome or a metagenome. The abundance score at a higher level can be computed as a derived value from multiple corresponding abundance scores at lower levels. An example abundance score topology based on the FIG. 53 data model is shown in FIG. 54.

Figure 55:
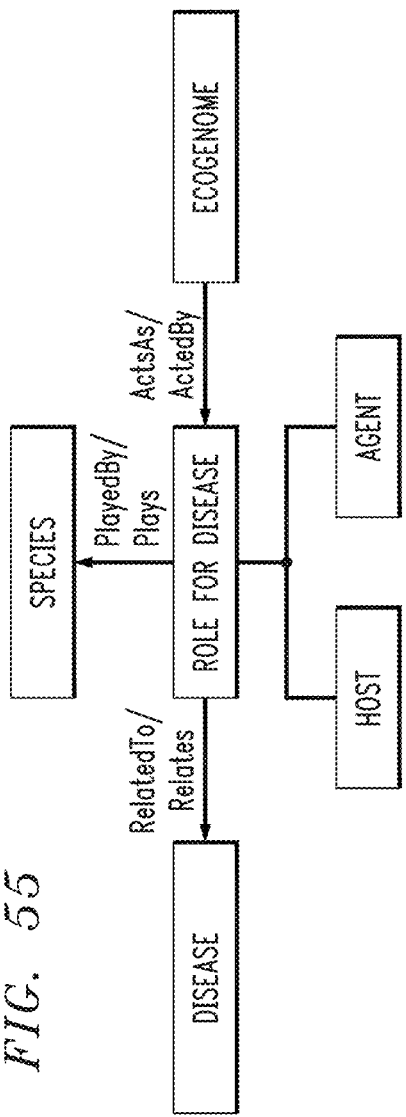

Data models in some embodiments are advantageously configured such that a given disease is no longer tied to a single genome but more generally to an ecogenome. For example, such an arrangement is useful when a disease has been identified on an instance of a given species but the specific component of the ecogenome that caused the disease is not known. Data models of this type can be configured to allow ecogenomes to take on different roles, including a role as host of a disease or a role as agent of a disease. FIG. 55 shows an example data model for diseases, hosts, agents and ecogenomes.

Figure 56:
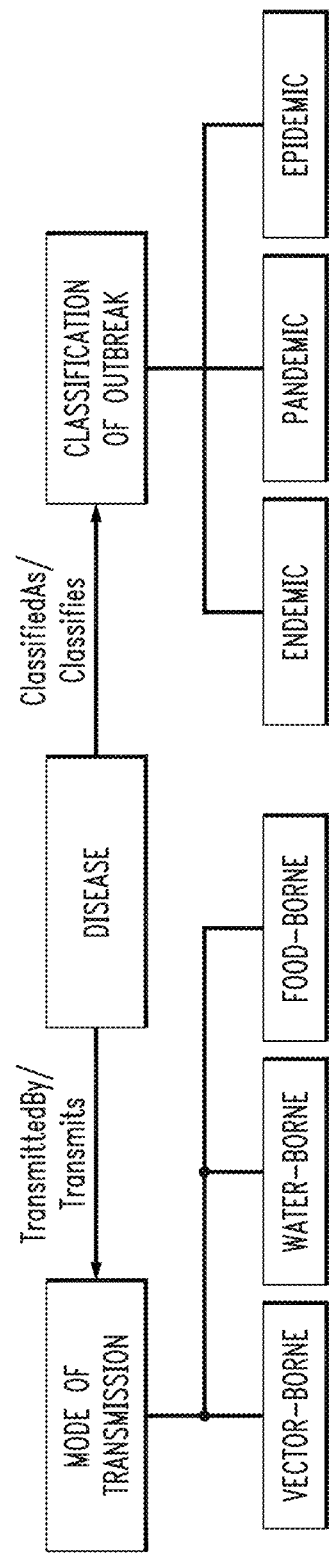

Also, a given disease can have properties such as a property indicating how the disease is transmitted. More particular examples of disease properties can include virulence and pathogenicity. FIG. 56 shows an example data model for modes of transmission and classification of outbreaks of a given disease.

Figure 57:
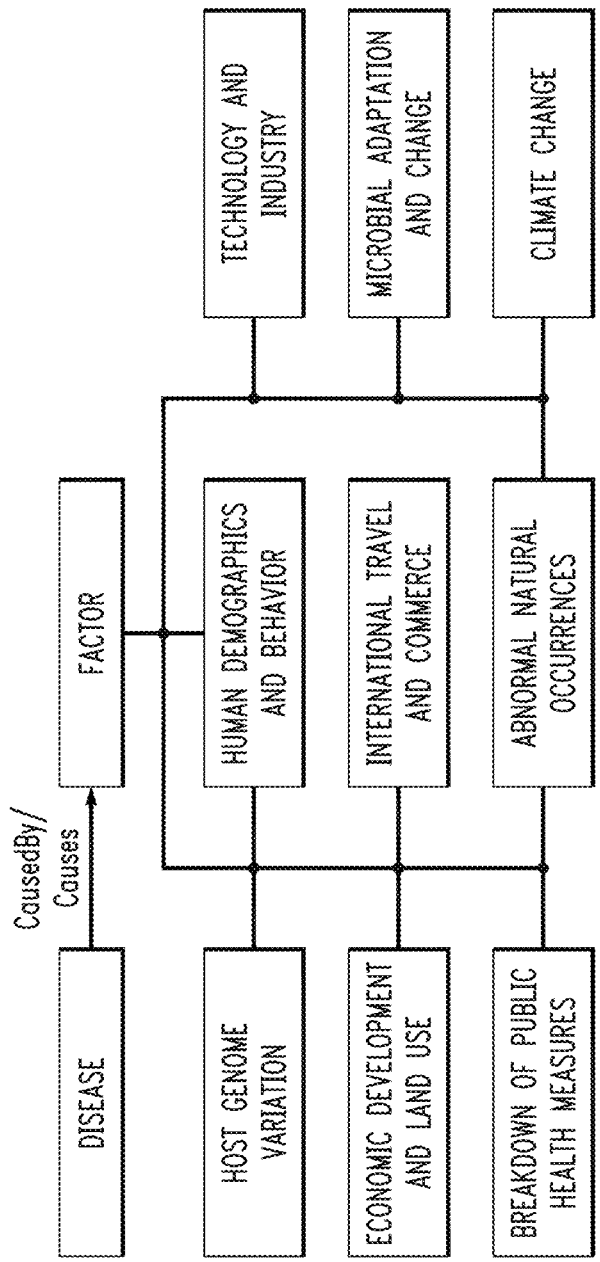
Figure 58:
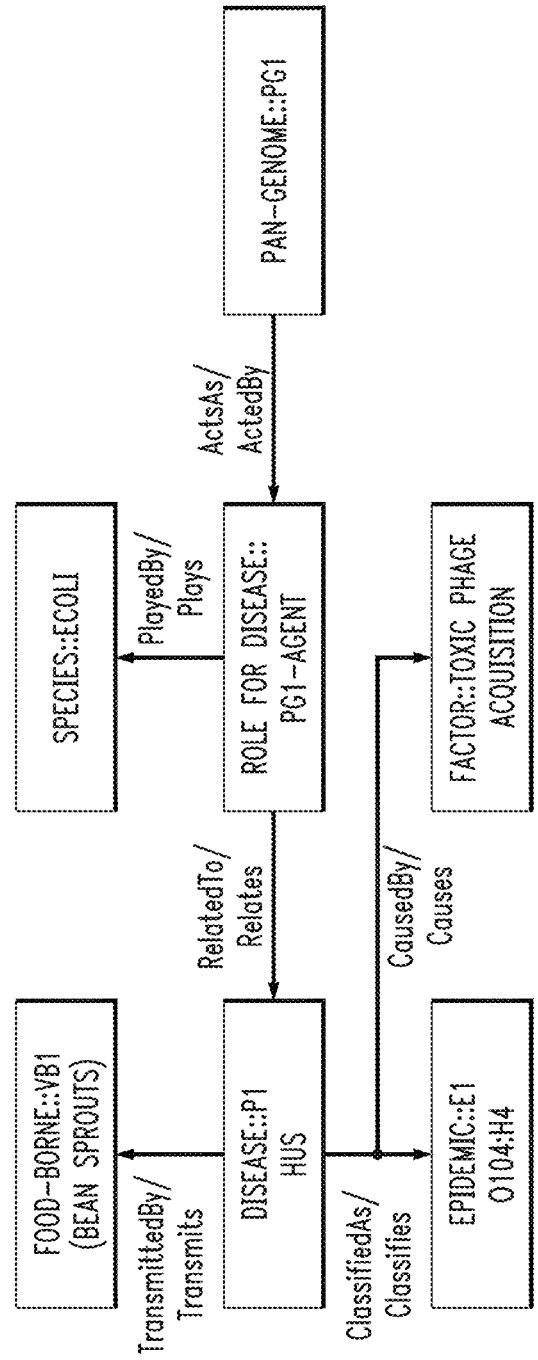

FIG. 57 shows an example data model that models factors for disease emergence. An illustrative topology for a given modeled disease utilizing the data models of FIGS. 55, 56 and 57 is shown in FIG. 58.

Figure 59:
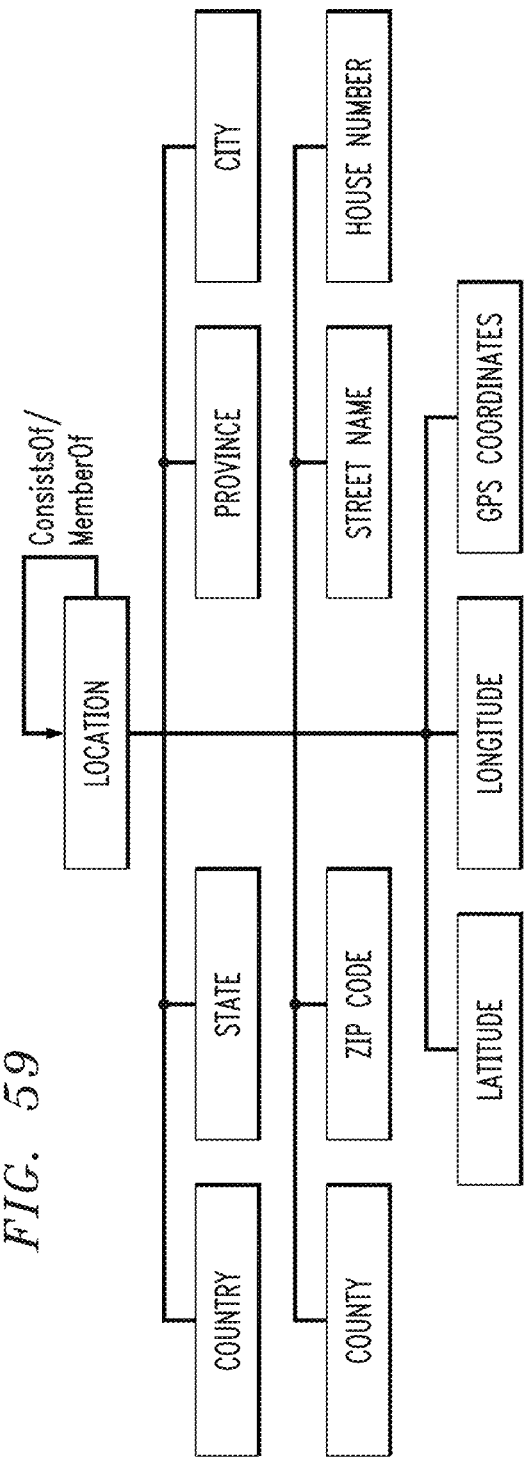
Figure 60:
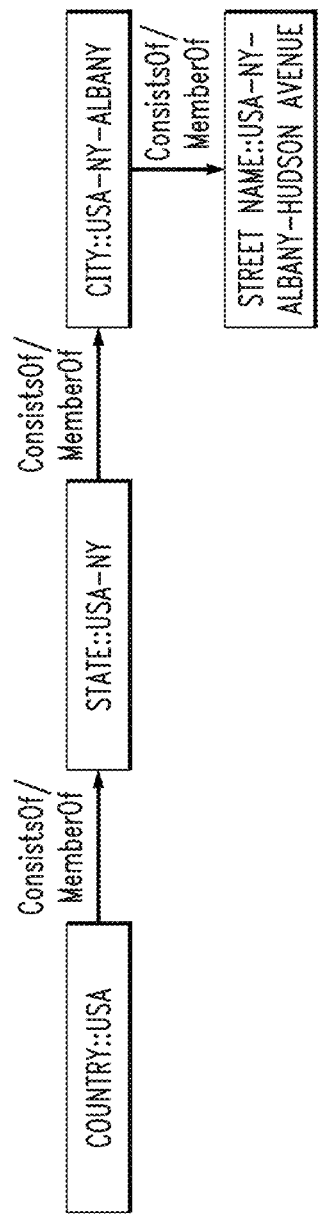

Location is another parameter that is modeled in illustrative data models disclosed herein. FIG. 59 shows an example of a location data model. It should be noted that some location information can be inferred from other location information. For example, if GPS coordinates are available, other location information such as latitude and longitude can be inferred. If GPS coordinates are not available, the data model can accommodate any available location information. An example topology based on the FIG. 59 data model is shown in FIG. 60.

Figure 61:
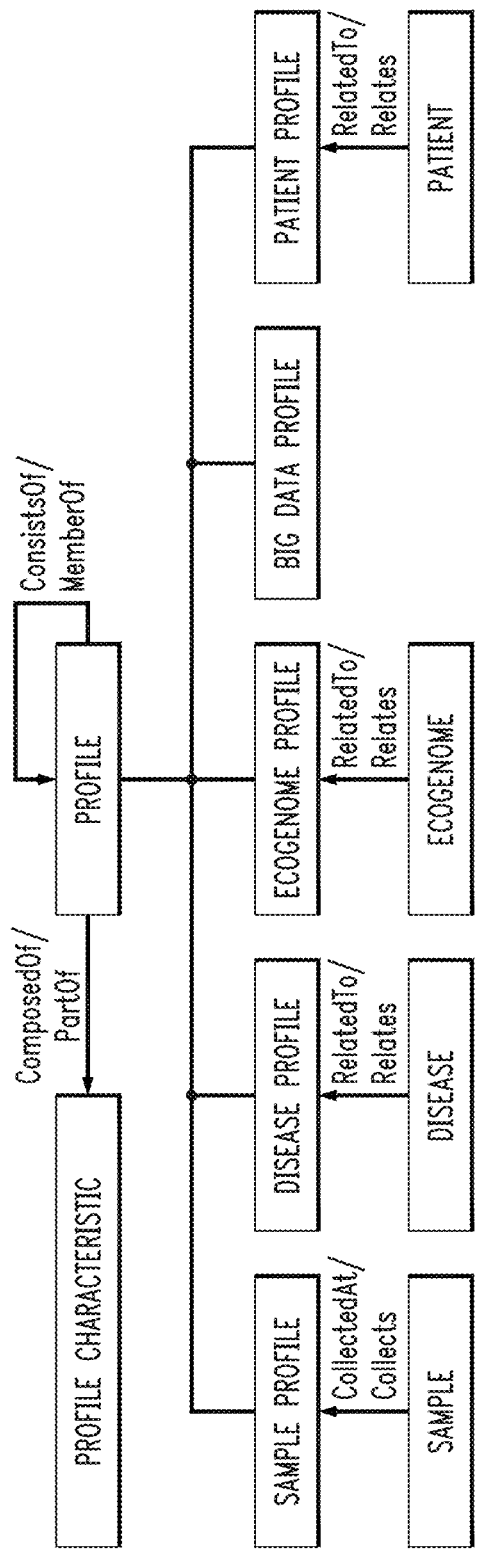
Figure 62:
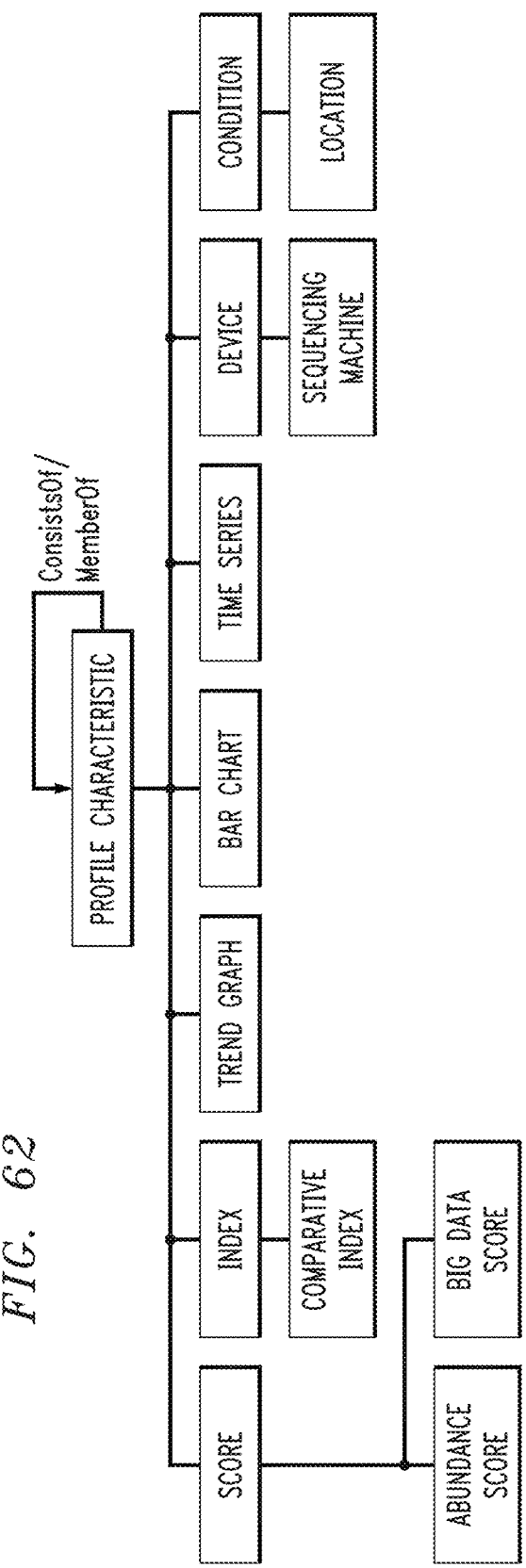
Figure 63:
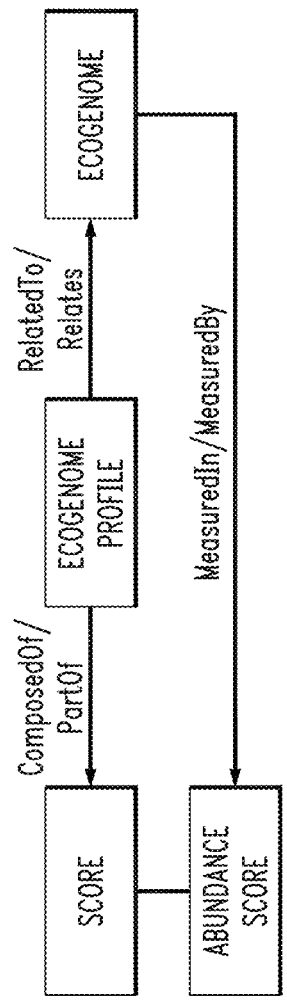

FIG. 61 shows a profile data model relating a profile to a profile characteristic and to one or more respective profiles for a sample, disease, ecogenome and patient. The profile data model also accommodates a Big Data profile as indicated. A corresponding example data model for the profile characteristic is shown in FIG. 62. A more particular example of a data model for a specific type of profile, in this case an ecogenome profile, is shown in FIG. 63.

Figure 64:
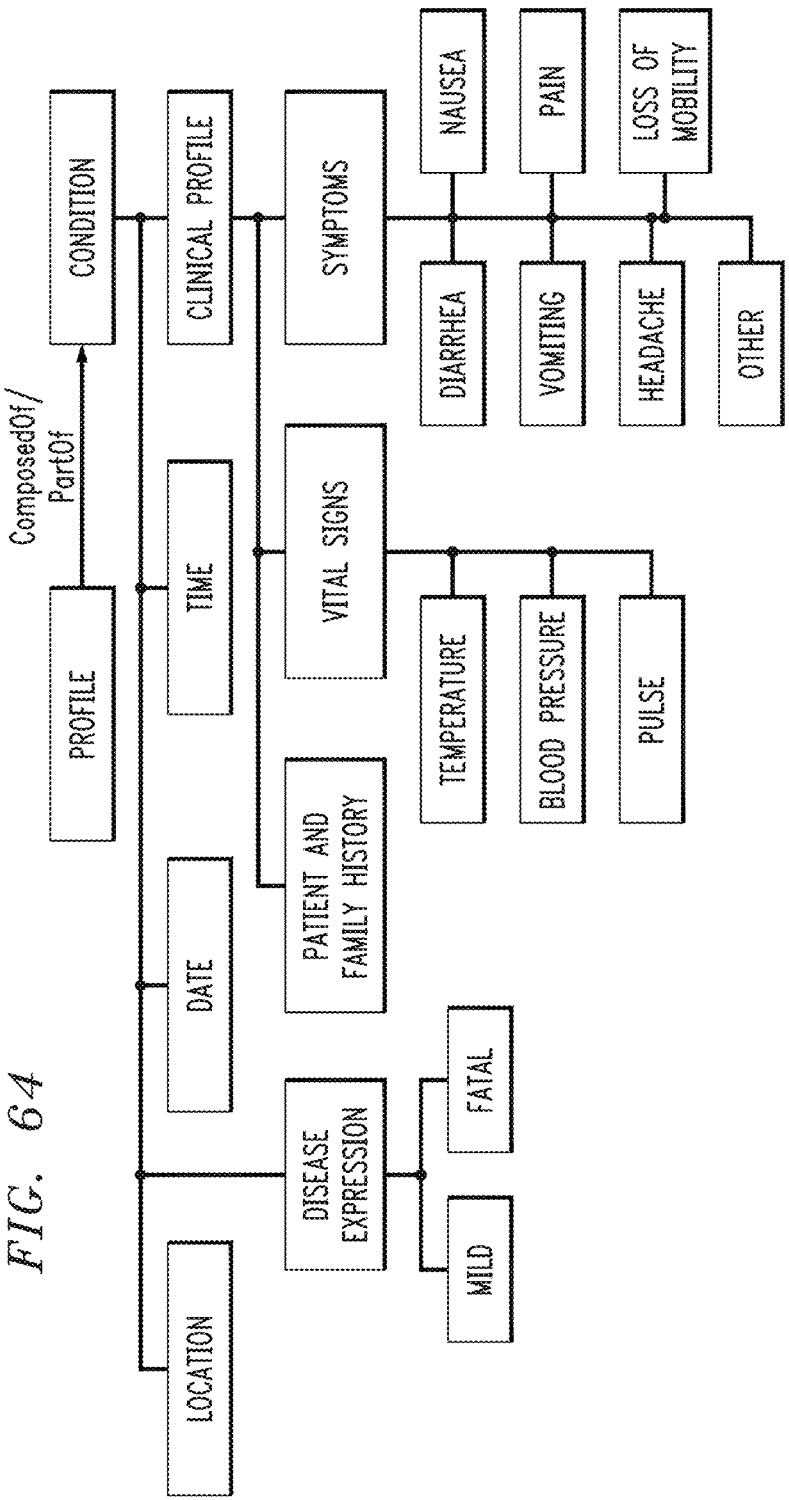
Figure 65:
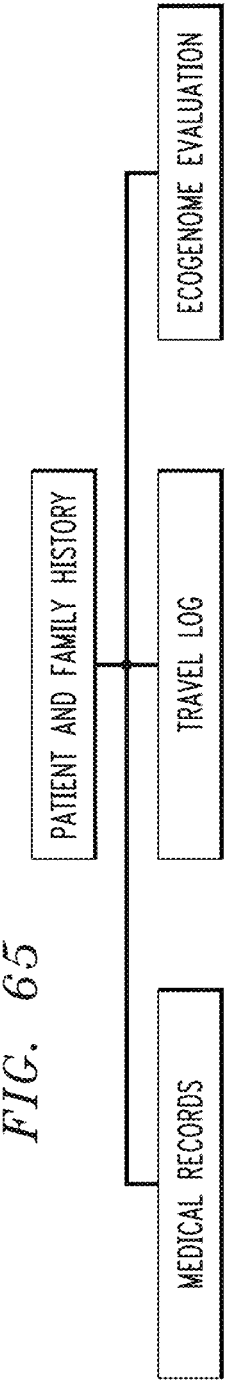

Referring now to FIG. 64, an example data model for a condition is shown, similar to the condition data model of FIG. 48. The FIG. 64 data model captures a variety of different types of non-genomic information related to the condition, including patient and family history which is separately modeled in FIG. 65.

Figure 66:
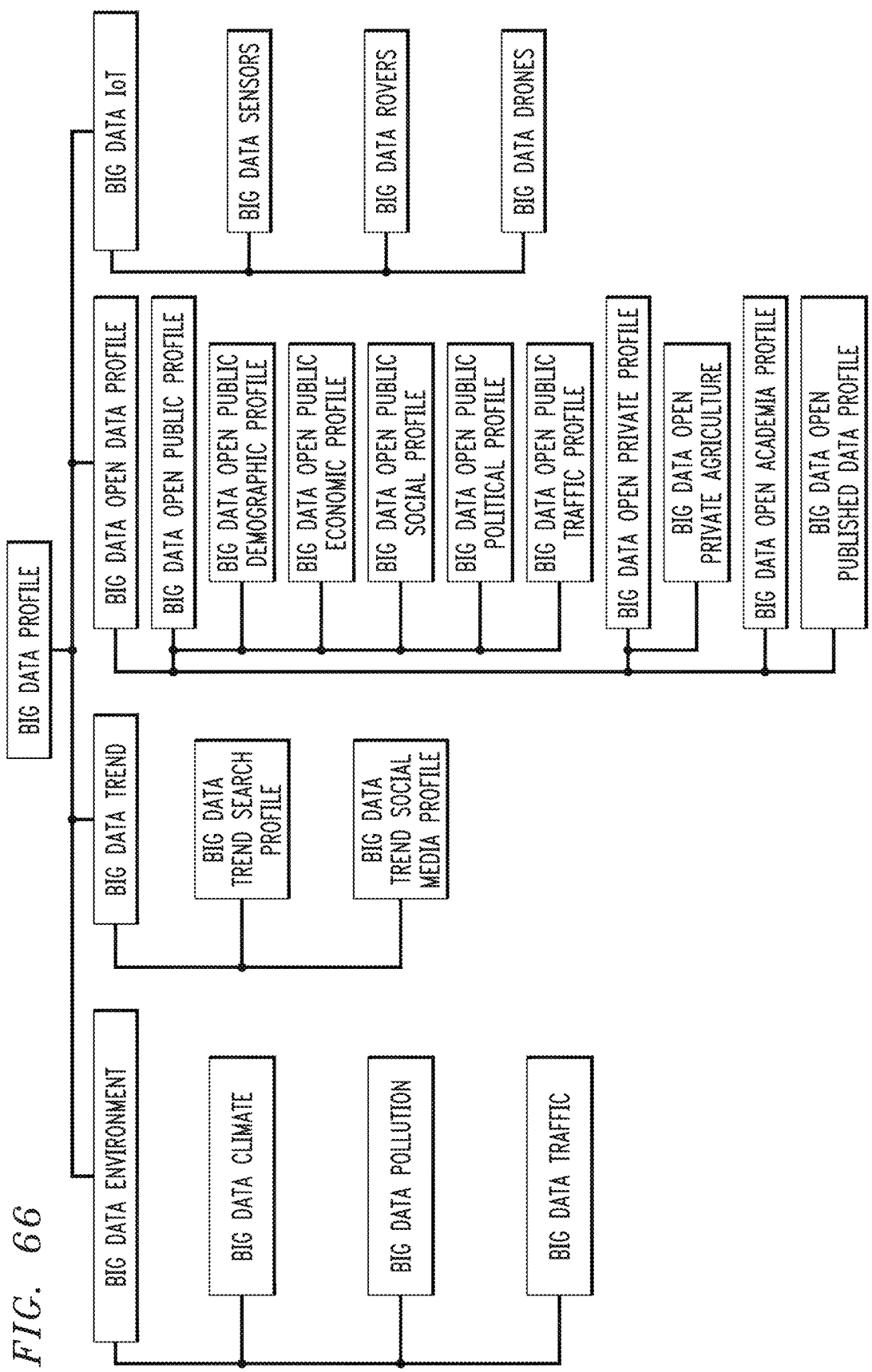

An example of a data model for the Big Data profile referred to in the profile data model of FIG. 61 is shown in FIG. 66.

Figure 67:
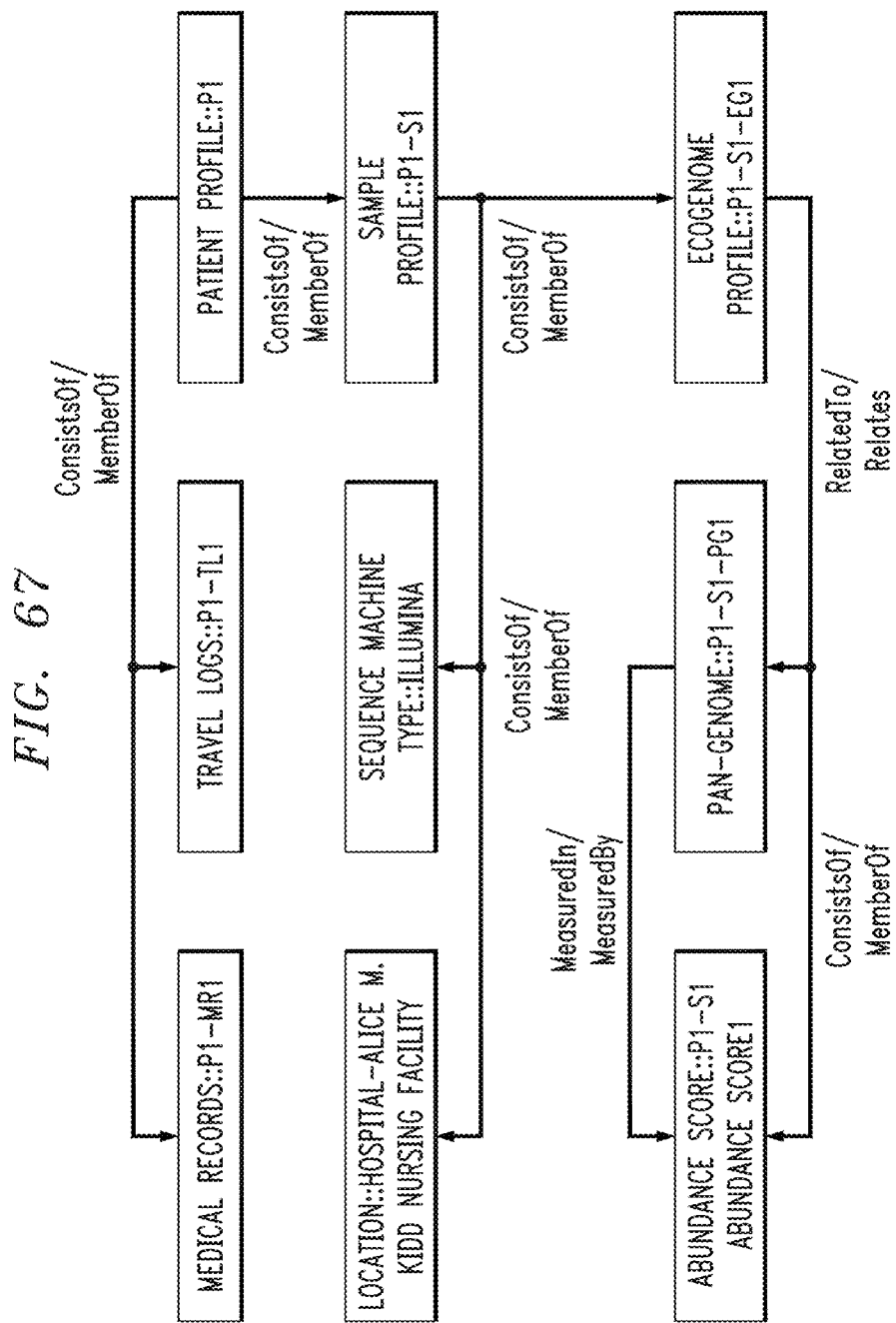
Figure 68:
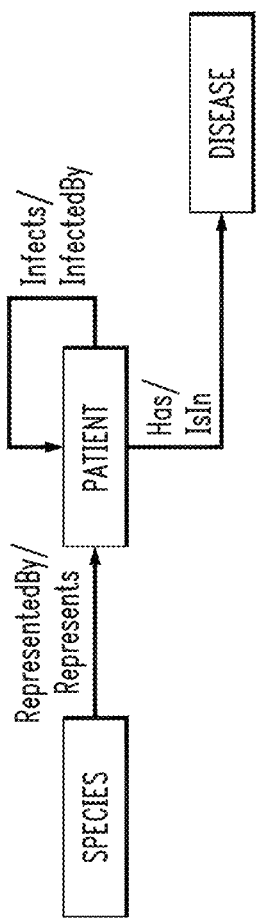

FIG. 67 shows an example topology based on various aspects of one or more of the data models of FIGS. 61-66.

Figure 69:
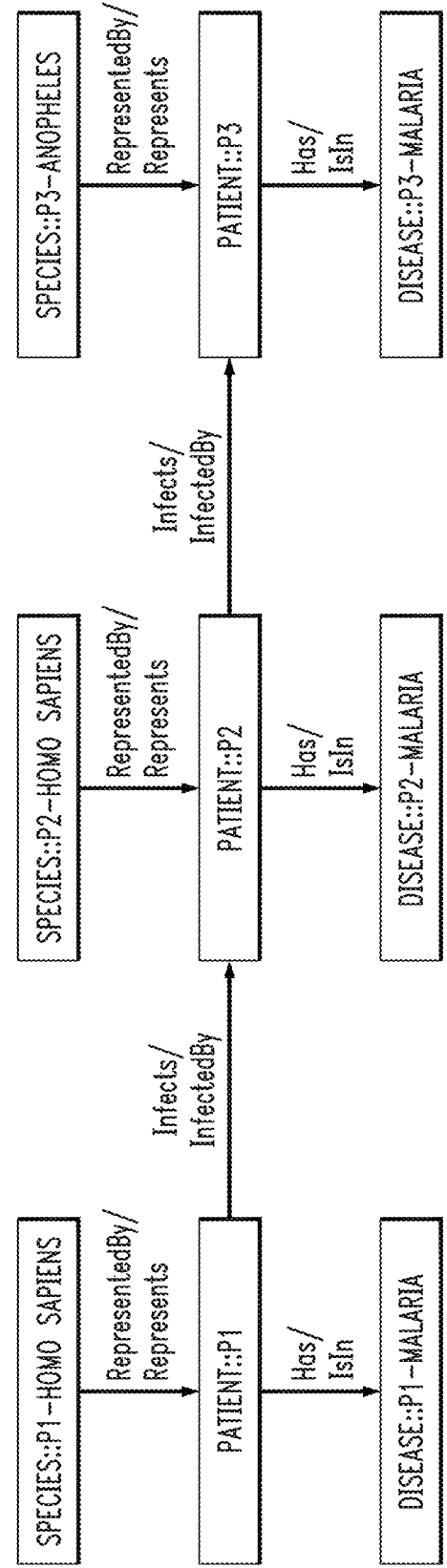

Aspects of data modeling relating to transmission networks and contact tracing will now be described. These data models recognize that a given instance of a species, such as a particular human being, can become a patient multiple times during its lifetime, and can also become a patient for several diseases at a time. This is more particularly illustrated in the data model of FIG. 68, in which the class Patient represents an occurrence of a particular disease within the lifetime of a patient. A corresponding topology example based on this patient and species data model is shown in FIG. 69.

Figure 70:
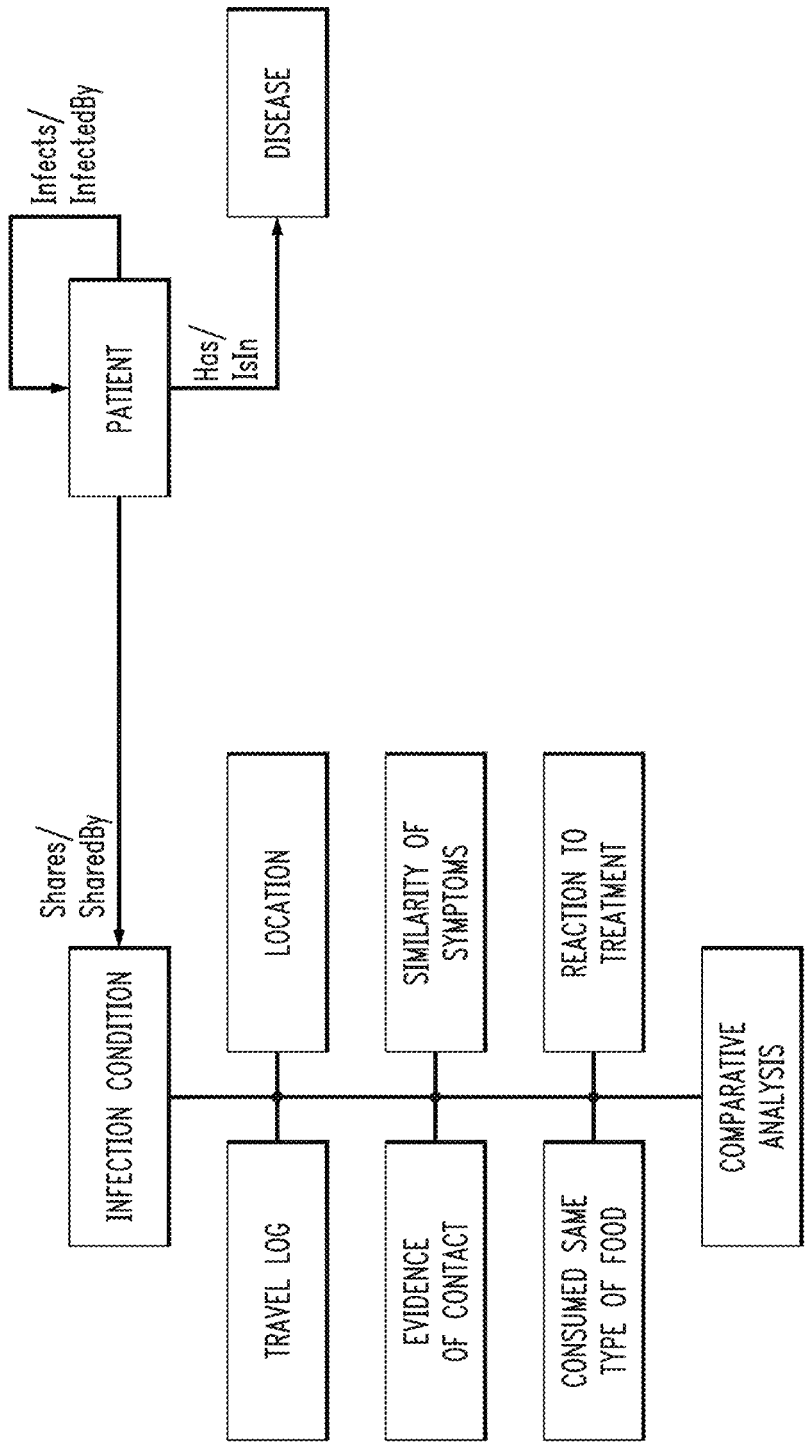

FIG. 70 illustrates a data model relating patient, disease and infection condition. In some cases, it is possible to know that a specific patient infected another specific patient, such that a relationship Infects/InfectedBy is created between two patients. In other cases, it is not possible to know how a given patient became infected. For those cases, identification of conditions shared by a group of patients is useful and accordingly such information is accommodated in the data model of FIG. 70. These and other aspects of the FIG. 70 data model capture information relating to contact tracing of patients.

In some embodiments, patients are characterized by a comparative analysis score that represents how "far apart" those patients are from one another from a disease perspective. For example, comparative analysis scores can be based on genome sequence alignment, similarities in external evidence, and other analysis parameters relating to two or more patients. Comparative analysis scores can be generated between pairs of patients, or alternatively between more than two patients within a designated group of patients. Comparative analysis scores are also referred to herein as simply "comparative scores."

Figure 71:
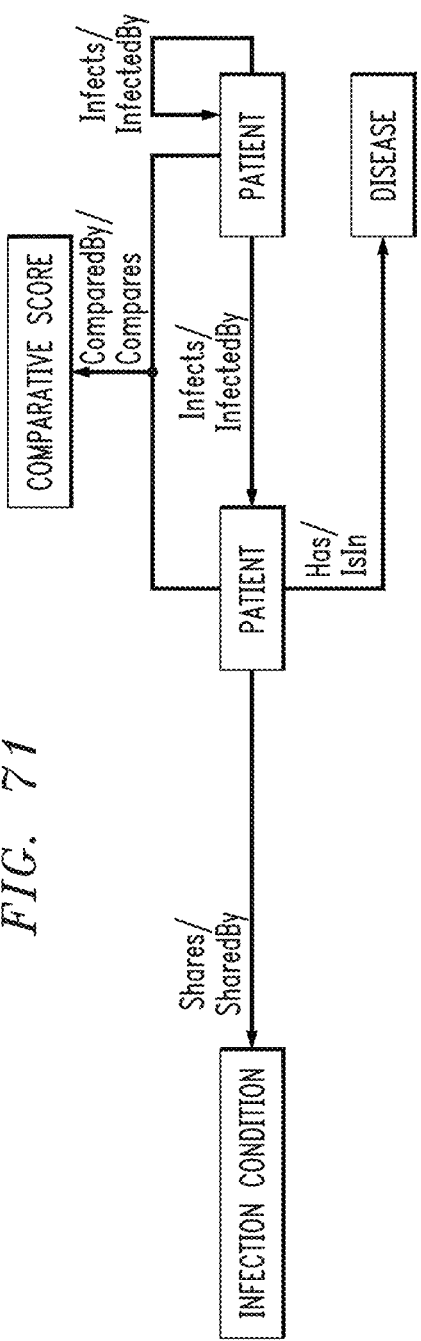
Figure 72:
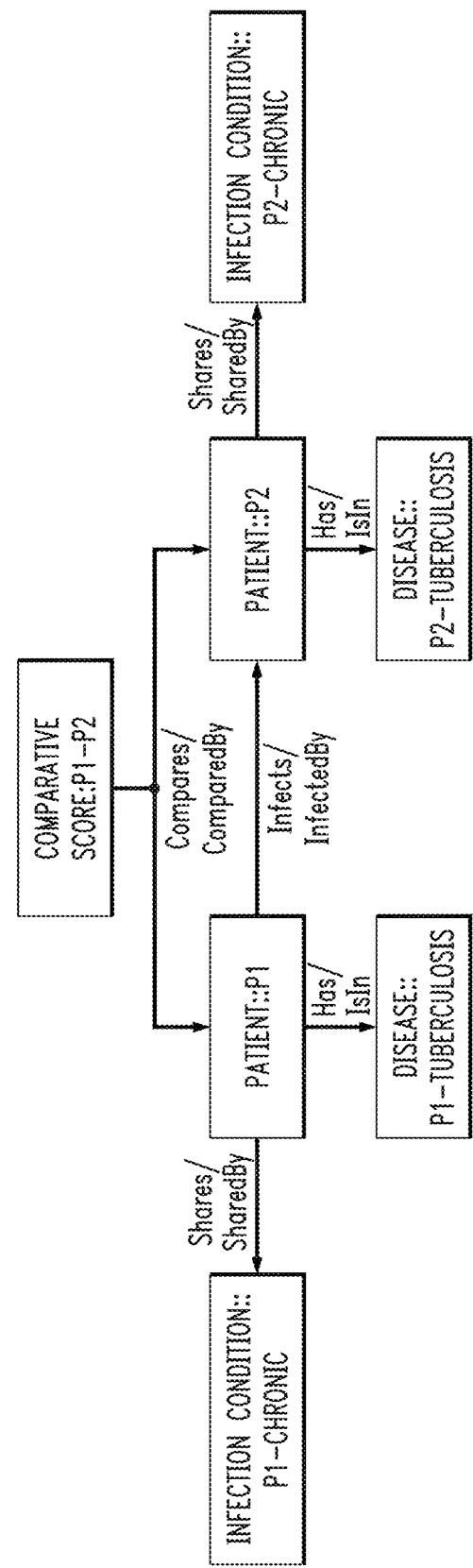

FIG. 71 shows an example data model that relates multiple patients to an infection condition, a disease and a comparative score. This comparative score relates to a pair of patients, but as noted above other comparative scores in other embodiments can characterize relationships between more than two patients. A corresponding example of a topology based on the FIG. 71 model and comparing patients P1 and P2 for a particular disease and infection condition is shown in FIG. 72.

Figure 73:
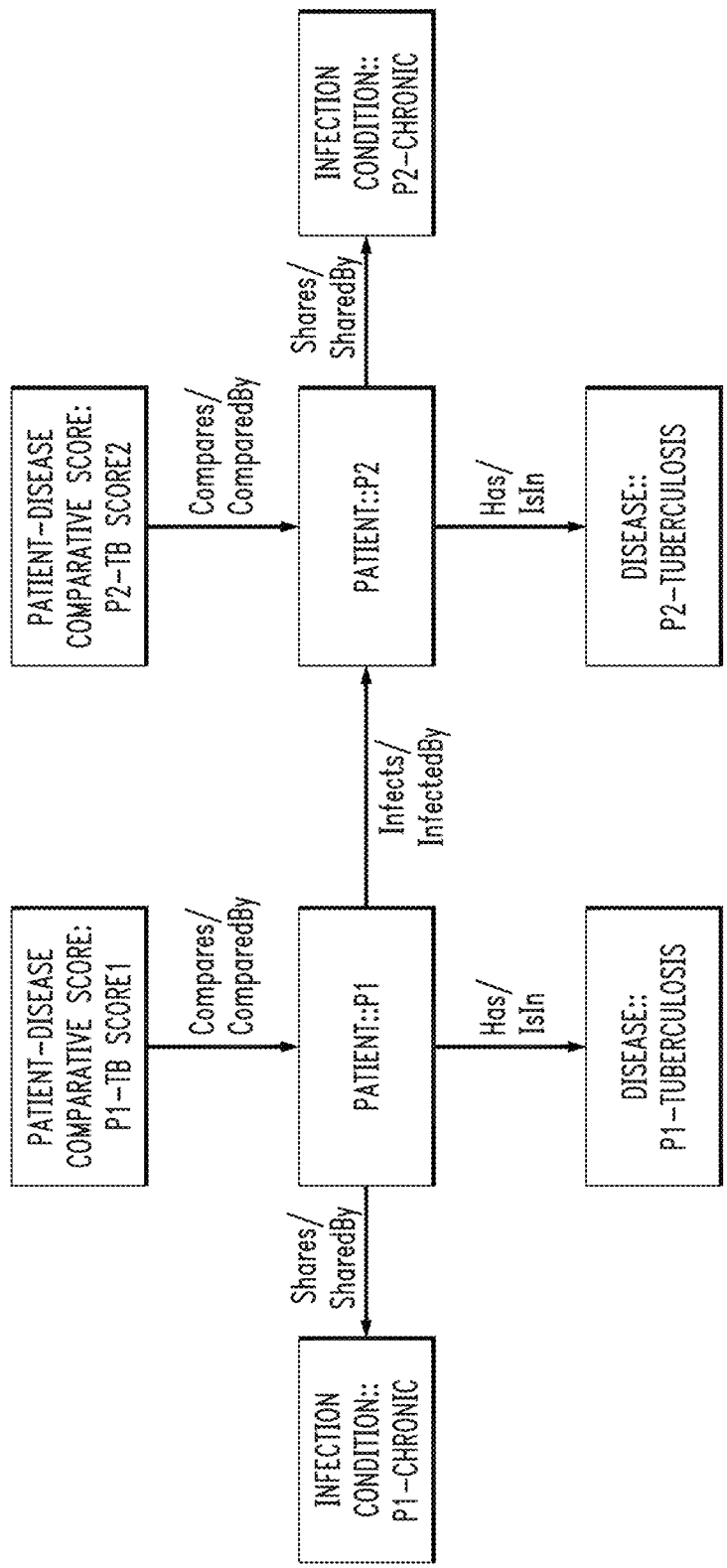

Another type of a comparative score that can be utilized in a given illustrative embodiment is a patient-disease comparative score. FIG. 73 shows a topology example that is similar to the FIG. 72 topology but utilizes respective patient-disease comparative scores for patients P1 and P2 instead of a single patient-patient comparative score. These and other comparative score data models can provide a parallel view between multiple patients that share a common disease, infection condition or epidemiologic history.

At least portions of multiple ones of the data models described above can be combined together in illustrative embodiments. Such portions are also referred to herein as "segments" of a larger data model. Accordingly, larger data models can be constructed by combining segments from multiple smaller data models.

Figure 74:
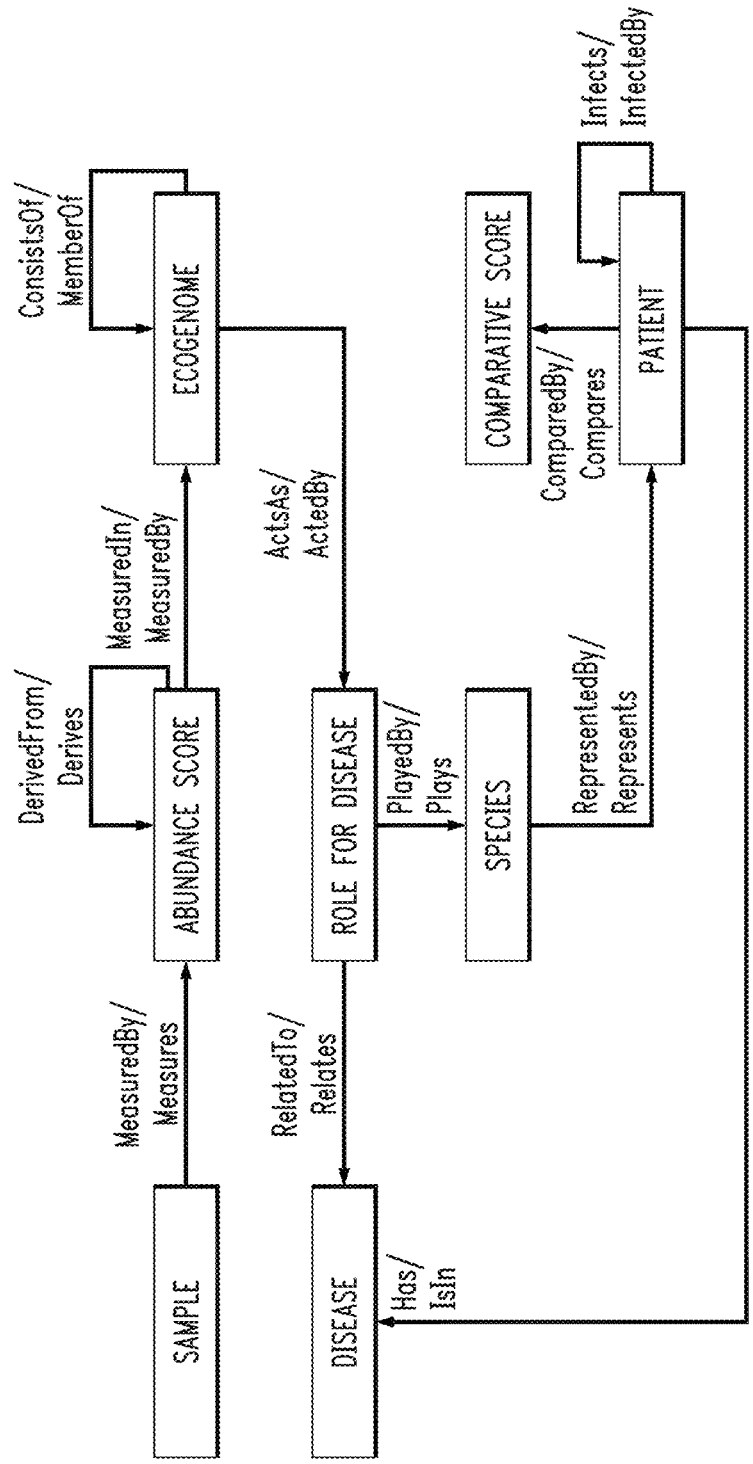

FIG. 74 shows an example of such a data model that relates abundance score and comparative score to sample, disease, role, species, patient and ecogenome. The data model in this embodiment is a combination of multiple segments from the data models previously described in conjunction with FIGS. 53, 68 and 71. This embodiment illustratively combines metagenome characterization and epidemiologic investigation by incorporating both abundance scores and comparative analysis. Numerous other combinations of distinct data model segments can be used in other embodiments.

In some embodiments, a given disease is characterized by a disease index that is a function of the abundance scores of all related samples and the comparative scores of all related patients, possibly supplemented by additional data from other aspects of the data model relating to the disease. A portion of an example data model associating a disease index with a disease is shown in FIG. 75.

Additionally or alternatively, a given patient in some embodiments is characterized by a comparative index that is a function of the abundance scores of all samples related to a disease associated with the patient and the comparative scores that the patient has with other patients, possibly supplemented by additional data from other aspects of the data model relating to the patient. A portion of an example data model associating a comparative index with a patient is shown in FIG. 76.

Figure 75:
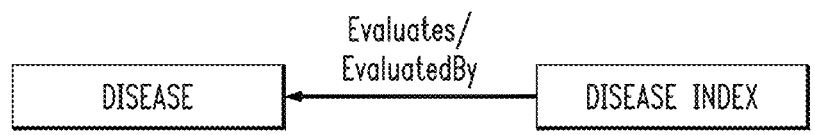
Figure 76:
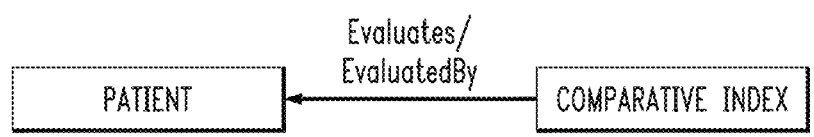
Figure 77:
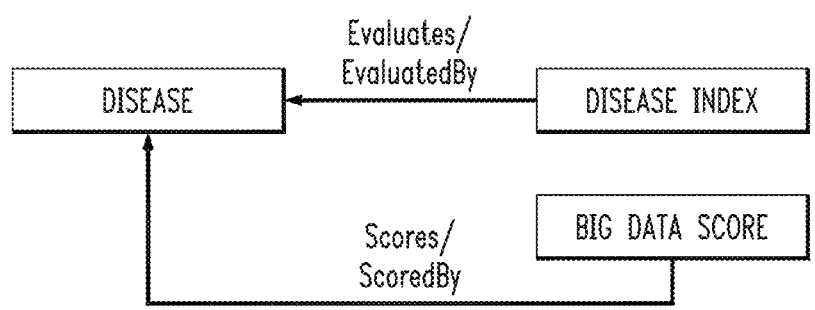
Figure 78:
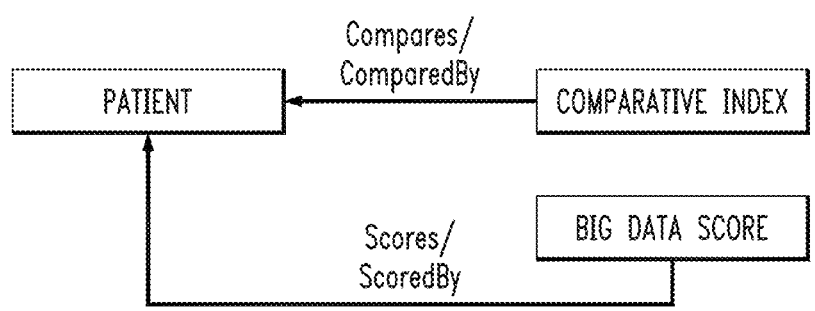

The disease index and comparative index data models of respective FIGS. 75 and 76 can each incorporate non-genomic Big Data scores, as illustrated in respective FIGS. 77 and 78. For example, with reference to the data model of FIG. 77, a disease can be further characterized by a disease Big Data score that is a function of additional non-genomic data associated with the disease. Similarly, with reference to the data model of FIG. 78, a patient can be further characterized by a patient Big Data score that is a function of additional non-genomic data associated with the patient.

Again, the particular data models, topologies and associated functionality described in conjunction with FIGS. 31 through 78 are presented by way of illustrative example only, and should not be construed as limiting in any way.

Additional illustrative embodiments will now be described with reference to FIGS. 79 through 85. These and other embodiments disclosed herein utilize distributed data analytics implemented in a distributed data processing system to detect at least one a disease, infection or contamination. A given such distributed data processing system is assumed to comprise a plurality of processing nodes. For example, the distributed data processing system in some embodiments illustratively comprises a plurality of WWH nodes of the type described elsewhere herein, configured to control performance of at least portions of the distributed data analytics to detect the disease, infection or contamination.

In some embodiments, outbreaks of infectious diseases are detected. Such outbreaks are typically caused by pathogens such as bacteria, virus, fungi or any other microorganism that can cause a disease. These pathogens contain virulence factors in their composition, some of which may be encoded in the genome of the pathogen itself. The virulence factors may give a pathogen the ability to invade and colonize a host, to produce toxins, or to evade or suppress host defense mechanisms.

The ability of a microorganism to cause a disease, infection or contamination is referred to as the pathogenicity of the microorganism, and is highly determined by its virulence factors. The term "virulence factors" as used herein is intended to encompass traits encoded by virulence genes that give pathogenic microorganisms their ability to cause a disease, infection or contamination. Examples of virulence factors include adherence factors, that help the pathogen adhere to cells, and capsule factors, that surround a pathogen in order to protect it. Other types of virulence factors include toxins.

Illustrative embodiments include next-generation outbreak surveillance systems based on metagenomics sequencing as disclosed herein. For example, a given such illustrative embodiment can include distributed sequencing centers scattered worldwide, where each center sequences entire microbiome samples and then analyzes the sequence reads generated against a set of known virulence factors to detect combinations causing diseases, allowing for near-real-time diagnostic analysis and targeted treatment. A given such embodiment may be configured to extend the Hadoop framework in the manner described elsewhere herein to orchestrate distributed and parallel computation across sequence centers, scattered worldwide, pushing computation as close as possible to the source of data. These extensions allow the distributed data analytics to leverage the principle of data locality at worldwide scale, while preserving data privacy, as the data is illustratively analyzed on premise at each sequencing center or otherwise within its corresponding data zone.

For example, a distributed application may be configured such that each one of a set of collaborating sequence centers calculates a profile of the virulence factors present in each of the microbiomes it has sequenced. The centers send these profiles to a center selected to do the global computation, which uses biclustering to uncover common patterns of virulence factors among subsets of microbiomes, which may have been originally sampled in any part of the world. This approach can not only identify early onset outbreaks but can also uncover new combinations of virulence factors that characterize new diseases.

The term "microbiome" as used herein is intended to be broadly construed, so as to encompass, for example, the combined genetic material of the microorganisms in a particular environment.

As noted above, some virulence factors are actually encoded in the genome of a microorganism. However, other virulence factors may be acquired by a microorganism later in its lifecycle due to gene transfer from another microorganism, making the receiving microorganism a carrier of that virulence factor. Such movement of genetic material between different microorganisms includes a type of gene transfer more particularly referred to as horizontal gene transfer.

Figure 79:
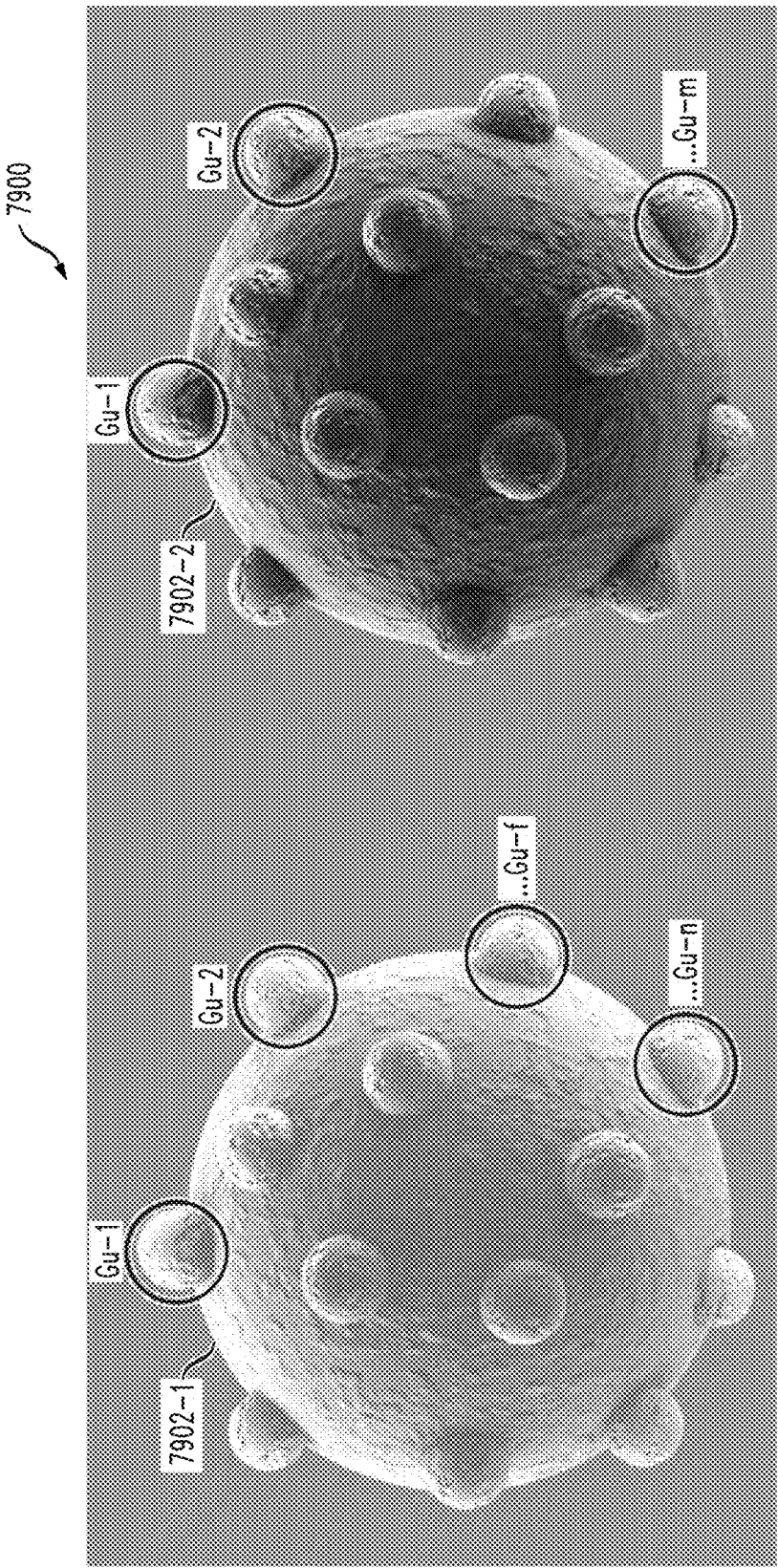
FIG. 79 illustrates a possible horizontal gene transfer arrangement resulting in pathogenicity that is detectable using distributed data analytics.

Referring now to FIG. 79, a horizontal gene transfer arrangement 7900 can result in pathogenicity that is detectable using distributed data analytics of the type described herein. In this example, a first pathogen 7902-1 includes gene units denoted Gu-1, Gu-2, . . . Gu-f, . . . Gu-n, at least a subset of which are responsible for its pathogenicity. Assume that gene units Gu-1, Gu-2 and Gu-f are responsible for the pathogenicity of the first pathogen 7902-1 and further that gene unit Gu-f is transferred to a second pathogen 7902-2 by horizontal gene transfer. The second pathogen 7902-2 therefore includes gene units denoted Gu-1, Gu-2, . . . Gu-f, . . . Gu-m and exhibits the same pathogenicity as the first pathogen 7902-1, due to the horizontal gene transfer of gene unit Gu-f from the first pathogen 7902-1. Such horizontal gene transfer is distinguished from vertical gene transfer, which involves transmission of genetic material from a parent to its offspring.

The genome of a given pathogen in some cases may include both core genes and accessory genes, with the core genes being responsible for its essential metabolic functions, and the accessory genes being acquired by horizontal gene transfer. Conditions such as global warming and climate change are creating an environment in which horizontal gene transfer of virulence factors is accelerating.

Figure 80:
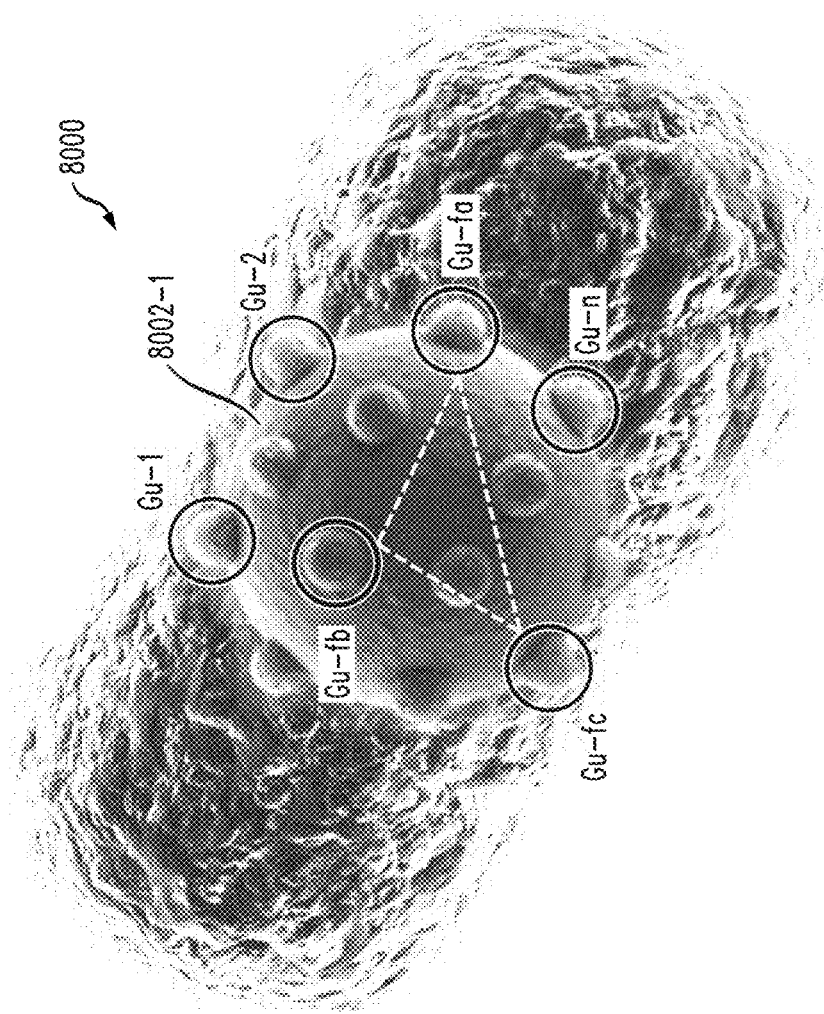
FIG. 80 illustrates pathogenicity caused by a combination of genetic factors within a single microorganism.

In some cases, pathogenicity is caused by a combination of genetic factors within a single microorganism. An example of this single microorganism pathogenicity situation is illustrated in FIG. 80, which shows a single microorganism 8000 having a pathogen 8002-1. The single microorganism is assumed to be part of a biological sample that includes additional microorganisms not explicitly shown in the figure. The pathogen 8002-1 of the single microorganism 8000 includes gene units denoted Gu-1, Gu-2, . . . Gu-fa, . . . Gu-fb, . . . Gu-fc, . . . Gu-n. It is further assumed in this example that the combination of gene units Gu-fa, Gu-fb and Gu-fc, all of which are present within the single microorganism 8000, collectively provide the pathogenicity associated with a particular disease.

Figure 81:
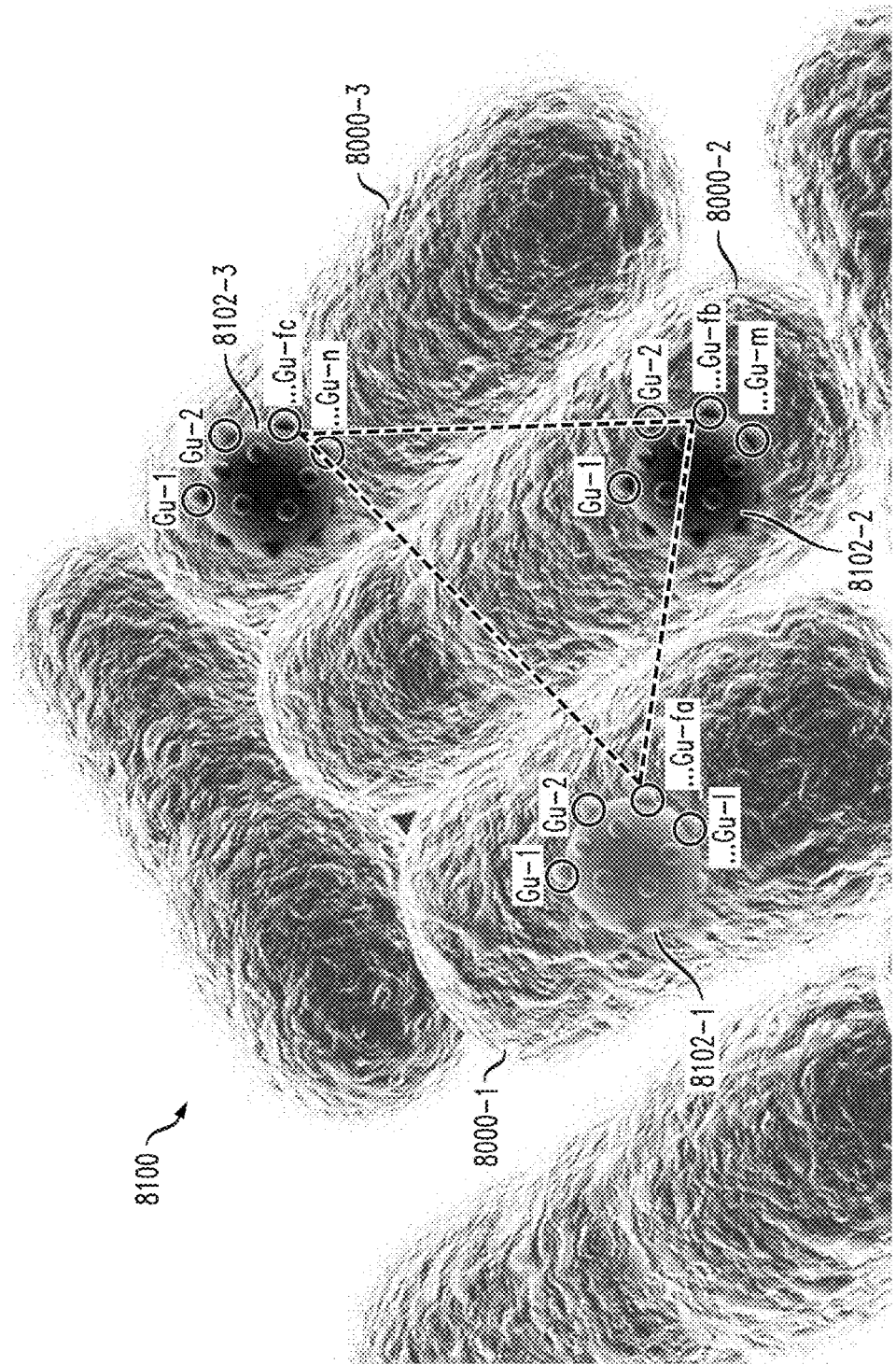
FIG. 81 illustrates pathogenicity caused by a combination of genetic factors across multiple distinct microorganisms.

In other cases, pathogenicity is caused by a combination of genetic factors across multiple distinct microorganisms. An example of this multiple microorganism pathogenicity situation is illustrated in FIG. 81, which shows a biological sample 8100 including multiple distinct microorganisms including microorganisms 8000-1, 8000-2 and 8000-3 having respective pathogen 8102-1, 8102-2 and 8102-3. The pathogen 8102-1 includes gene units denoted Gu-1, Gu-2, . . . Gu-fa, . . . Gu-1, the pathogen 8102-2 includes gene units denoted Gu-1, Gu-2, . . . Gu-fb, . . . Gu-m, and the pathogen 8102-3 includes gene units denoted Gu-1, Gu-2, . . . Gu-fc, . . . Gu-n. It is again assumed in this example that the combination of gene units Gu-fa, Gu-fb and Gu-fc collectively provide the pathogenicity associated with a particular disease. However, in this case, the gene units Gu-fa, Gu-fb and Gu-fc are spread across the three distinct microorganisms 8000-1, 8000-2 and 8000-3 of the biological sample 8100.

Although the microorganisms 8000 in the FIG. 81 example are assumed to be part of the same biological sample 8100, the distributed data analytics implemented in illustrative embodiments is advantageously configured to detect diseases, infections or contaminations even in situations in which the virulence factors of the disease, infection or contamination are distributed across multiple microorganisms from different biological samples that are sequenced in different, potentially geographically-dispersed sequencing centers.

Figure 82:
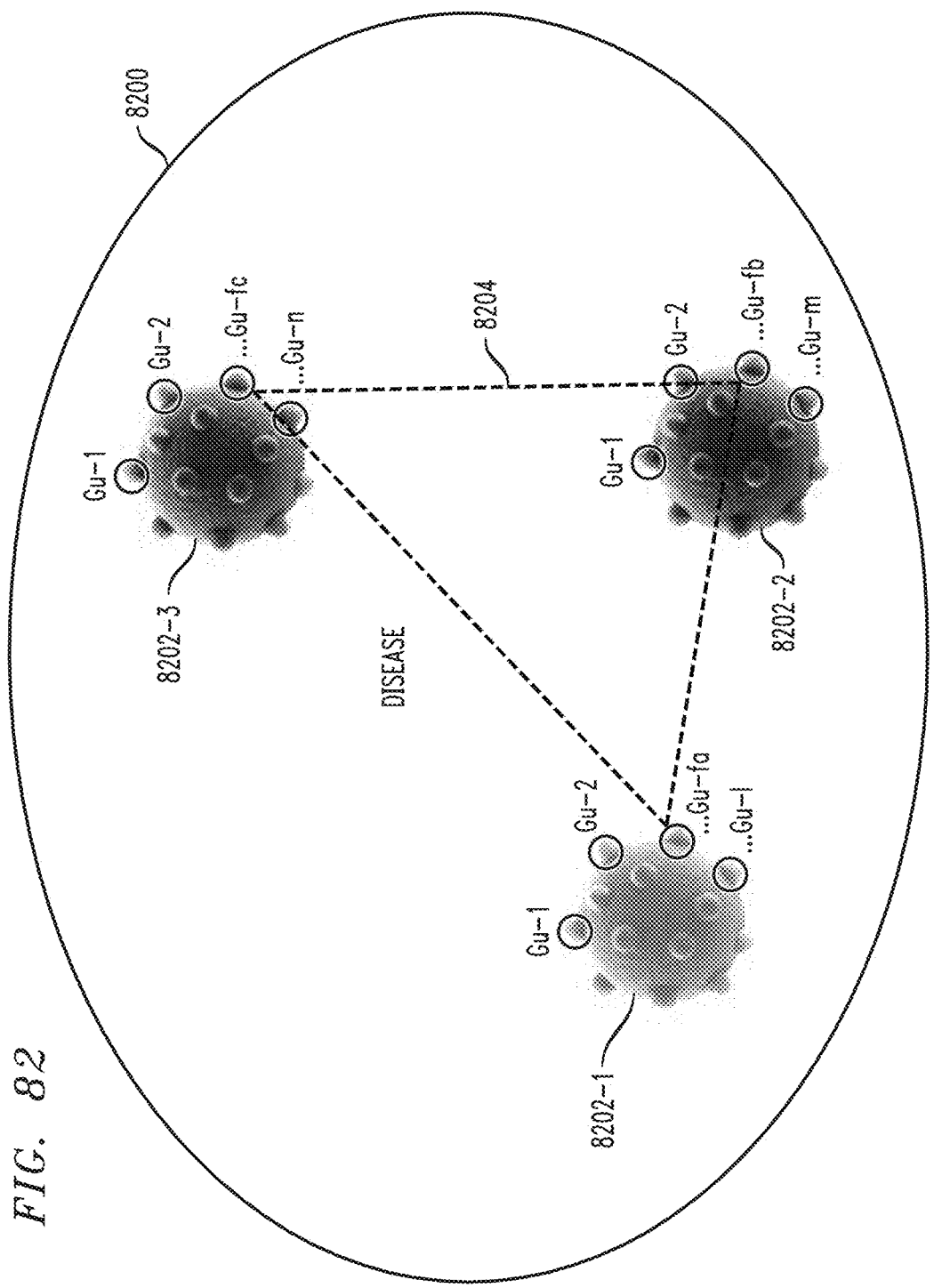
FIG. 82 shows an example of a disease characterized using distributed data analytics to detect pathogenicity across pathogens from microorganisms in potentially different biological samples.

This more general situation is illustrated in FIG. 82, in which a disease 8200 is characterized by a combination of gene units Gu-fa, Gu-fb and Gu-fc of respective pathogens 8202-1, 8202-2 and 8202-3. However, the pathogens 8202 in this example may be part of different microorganisms in different biological samples sequenced in different sequencing centers. The different biological samples may be taken from different microbiomes. The distributed data analytics disclosed herein can nonetheless detect the connection 8204 between the gene units and its association with disease 8200. Illustrative embodiments can therefore detect diseases, infections and contaminations that would be otherwise undetectable using conventional culture-based isolation sequencing approaches.

For example, some illustrative embodiments are configured to obtain reads of biological samples of respective microbiomes wherein each of the biological samples contains genomic material from a plurality of distinct microorganisms of its corresponding one of the microbiomes, and to perform distributed data analytics to detect a disease, infection or contamination that involves genomic material from multiple ones of the distinct microorganisms in one or more of the microbiomes. The reads of the biological samples may comprise respective sets of gene units sequenced from those biological samples in corresponding ones of a plurality of sequencing centers.

The above-noted example operations are illustratively performed by a distributed data processing system comprising a plurality of processing devices configured to communicate with one another over at least one network, as described in conjunction with the FIG. 1 embodiment and other embodiments previously described herein.

Additional illustrative embodiments of this type will be described below with reference to FIGS. 83 through 85. It is assumed for these embodiments that the distributed data analytics comprises local analytics performed in respective ones of a plurality of data zones, and global analytics that are performed utilizing results of the local analytics performed in the respective data zones. Each of the data zones comprises one or more sequencing centers utilized to generate a corresponding subset of the reads within that data zone. A result of the global analytics characterizes the disease, infection or contamination as involving genomic material identified in different ones of the reads of the biological samples generated in different ones of the data zones by corresponding different ones of the sequencing centers. Advantageously, the result of the global analytics can be obtained without requiring reassembly of the genomic material identified in the different reads generated by the different sequencing centers into genomes of respective ones of the distinct microorganisms.

Figure 83:
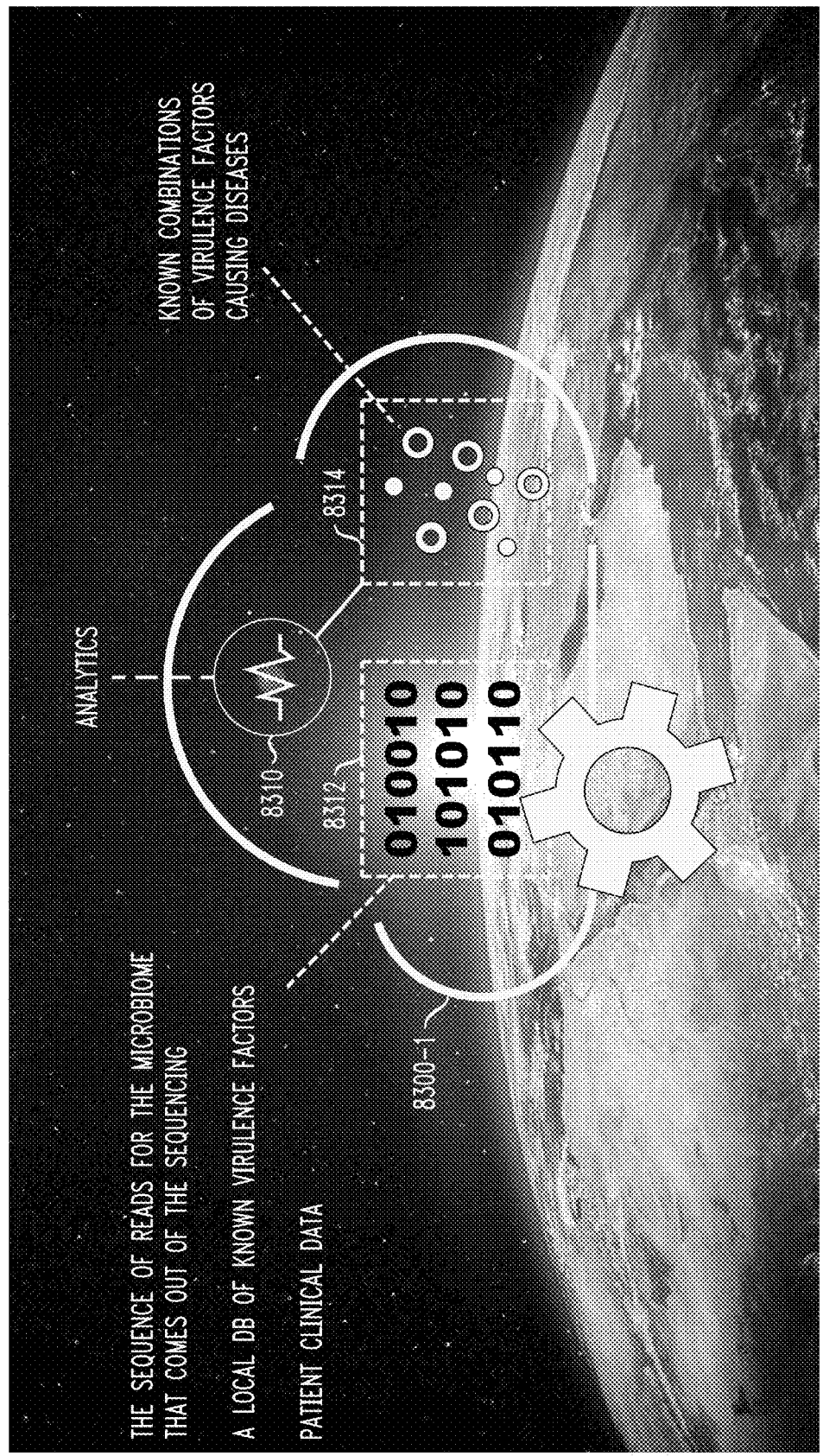
FIG. 83 shows an example of local analytics performed in a given data zone of a distributed data processing system in an illustrative embodiment.

FIG. 83 shows an example of local analytics performed in a given one of the data zones of a distributed data processing system in an illustrative embodiment. The given data zone is identified by reference numeral 8300-1. The local analytics performed in this embodiment include analytics 8310 configured to utilize reads of one or more of biological samples sequenced in the one or more sequencing centers of the given data zone 8300-1. For example, the analytics 8310 performed in data zone 8300-1 comprise analyzing a sequence of reads of the one or more biological samples against a local database ("DB") 8312 storing known virulence factors, and possibly other information such as patient clinical data. The sequence of reads is assumed to reads for one or more biological samples of a particular microbiome, as generated by sequencing performed in a sequencing center of the data zone 8300-1. The data zone 8300-1 in this embodiment also stores known combinations 8314 of virulence factors causing diseases. The analytics 8310 performed in the data zone 8300-1 illustratively comprise generating a virulence profile for the sequence of reads of the one or more biological samples of the particular microbiome. Such a virulence profile can form at least part of the results of the analytics 8310 of the data zone 8300-1 that are utilized in performing the global analytics.

The local analytics performed in a given data zone such as data zone 8300-1 of FIG. 83 are illustratively performed at least in part in parallel with the local analytics performed in one or more other ones of the data zones of the distributed data processing system. In some embodiments, a result of the global analytics can also be generated in a particular one of the data zones that performs local analytics.

Figure 84:
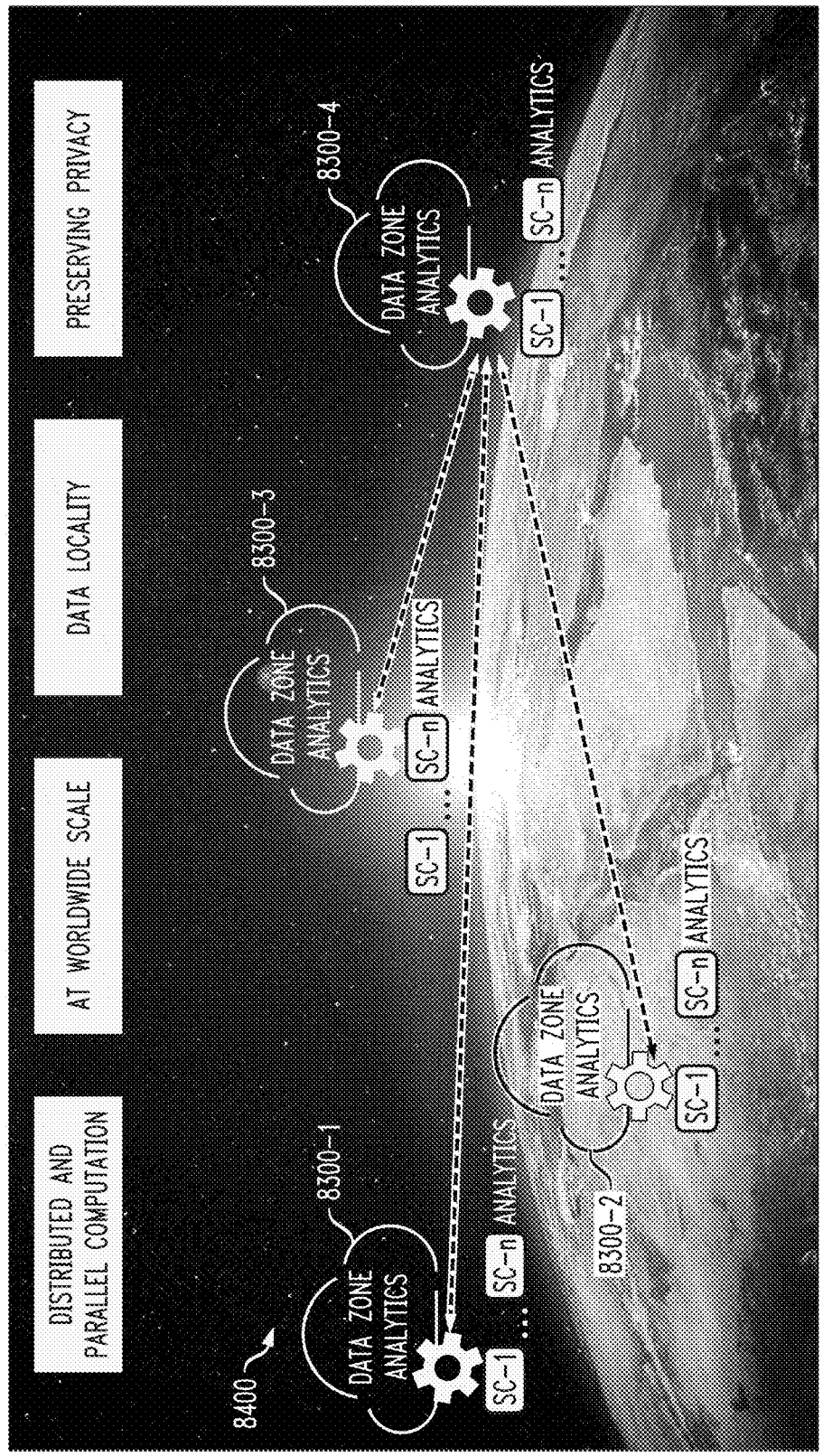
FIG. 84 illustrates one possible implementation of a distributed data processing system configured to perform local analytics and global analytics.

FIG. 84 illustrates one possible implementation of a distributed data processing system 8400 configured to perform local analytics and global analytics. The system 8400 includes the data zone 8300-1 previously described in conjunction with FIG. 83 as well as a plurality of additional data zones 8300-2, 8300-3 and 8300-4. The data zones 8300 in this embodiment are assumed to comprise respective geographically-distributed regional data centers each configured to perform local analytics utilizing locally accessible data resources of its corresponding data zone. The system 8400 is therefore configured to implement distributed and parallel computation among the regional data centers at worldwide scale, utilizing data locality and preserving privacy in the local data of the multiple data zones 8300. For example, results of the local analytics performed in the respective data zones 8300 are illustratively configured preserve for each of the data zones at least one specified policy of that data zone relating to at least one of privacy, security, governance, risk and compliance.

Each of the data zones 8300 in system 8400 is assumed to include a plurality of sequencing centers denoted SC-1, . . . SC-n. The sequencing centers in the data zones 8300 generate reads of biological samples of respective microbiomes with each of the biological samples containing genomic material from a plurality of distinct microorganisms of its corresponding one of the microbiomes. Each of the data zones 8300 in this embodiment utilizes one or more of its corresponding sequencing centers SC-1, . . . SC-n to generate a corresponding subset of the reads within that data zone.

The system 8400 performs distributed data analytics to detect a disease, infection or contamination that involves genomic material from multiple ones of the distinct microorganisms in one or more of the microbiomes. The reads of the biological samples comprise respective sets of gene units sequenced from those biological samples in corresponding ones of the sequencing centers.

The distributed data analytics in this embodiment are assumed to comprise performing local analytics in respective ones of the data zones 8300, and performing global analytics utilizing results of the local analytics performed in the respective data zones. It is assumed that local analytics are performed in each of the data zones 8300-1 through 8300-4, while the global analytics are performed only in data zone 8300-4, although numerous other arrangements are possible in other embodiments. Data zone 8300-4 is therefore an example of a data zone that performs both local analytics and global analytics. A result of the global analytics characterizes the disease, infection or contamination as involving genomic material identified in different ones of the reads of the biological samples generated in different ones of the data zones 8300 by corresponding different ones of the sequencing centers SC-1, . . . SC-n of those data zones.

Figure 85:
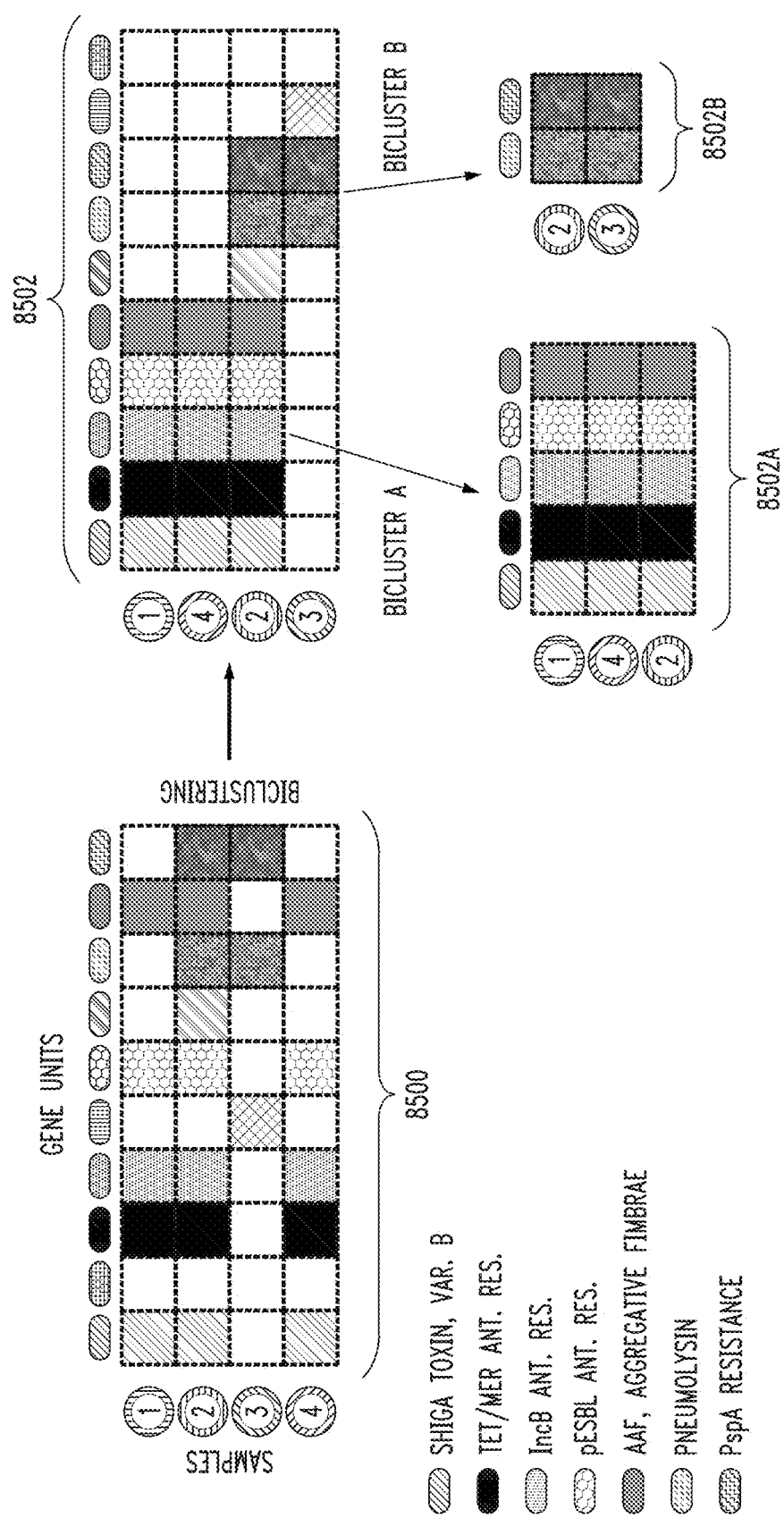
FIG. 85 illustrates a biclustering operation performed as part of global analytics applied to local analytics results characterizing gene units from multiple biological samples in the distributed data processing system of FIG. 84.

FIG. 85 illustrates a biclustering operation performed as part of global analytics applied to local analytics results characterizing gene units from multiple biological samples in the distributed data processing system 8400 of FIG. 84. In this embodiment, a result of the global analytics performed in data zone 8300-4 is assumed to be generated at least in part by performing one or more biclustering operations on results of the local analytics performed in the respective data zones 8300-1 through 8300-4.

The biclustering operation shown in FIG. 85 is performed on a hit abundance score matrix 8500 of a type previously described herein. The hit abundance score matrix 8500 in this embodiment more particularly relates reads of different ones of a plurality of biological samples sequenced in different ones of the sequencing centers of different data zones to respective different ones of a plurality of target genomic sequences. The hit abundance score matrix 8500 comprises multiple hit abundance score vectors, with the rows of the hit abundance score matrix 8500 corresponding to respective different ones of the biological samples and the columns of the hit abundance score matrix 8500 corresponding to respective different ones of the target genomic sequences. The biclustering operation in this embodiment produces a reordered matrix 8502 that includes a first bicluster 8502A also denoted Bicluster A and a second bicluster 8502B also denoted Bicluster B. Other types of biclustering operations producing different types of outputs can be used in other embodiments.

The distributed data processing system 8400 is able to detect diseases caused by patterns of gene units in reads of biological samples that may be in different genomes. For example, the system 8400 can detect a disease caused by a combination of pathogens collectively providing a particular pattern of gene units {a, b, c} where each of the gene units is sampled from a different microorganism potentially associated with a different genome but within a common microbiome, as described in conjunction with the embodiments of FIGS. 81 and 82. The biological sample in such an arrangement may comprise, for example, a sample of water or another type of fluid taken from a microbiome that includes several different bacteria, such as bacteria Ba, Bb and Bc comprising respective ones of the gene units a, b and c of the set of gene units {a, b, c}. Alternative approaches that are able to process gene units from only a single genome would be unable to detect diseases of this type.

Accordingly, in some embodiments, one or more of the biological samples may each represent a microbiome containing genomic material from multiple distinct microorganisms that inhabit the microbiome. The distributed data analytics in such embodiments is performed across multiple reads from the multiple distinct microorganisms within the microbiome. Such distributed data analytics is advantageously performed without the need for reassembly of the genomic material identified in the different reads generated by different sequencing centers into genomes of respective ones of the distinct microorganisms.

As indicated above, the distributed data processing system 8400 comprises a worldwide arrangement of sequencing centers in multiple data zones 8300. Each of the sequencing centers can be configured to sequence biological samples from entire microbiomes, potentially generating millions of reads and performing local analytics such as comparing sequences of reads to local databases of known virulence factors.

In some embodiments, the previously-described WWH framework is leveraged to create a distributed application in which results of the local analytics in the form of virulence profiles based on the reads generated in the respective data zones are transmitted to a designated data zone for performance of global analytics. Such virulence profiles illustratively include information such as the abundance of certain virulence factors within the microbiome, and do not contain any private or personal data.

The global analytics illustratively utilizes biclustering operations to uncover common patterns of virulence factors across several microbiomes, not only potentially identifying onset of outbreaks but also new combinations of virulence factors that were not known before, potentially characterizing new diseases.

This approach allows researchers and public health organizations to potentially identify the early onset of outbreaks and also uncover new combinations of virulence factors that may characterize new diseases. It also provides enhanced collaborative arrangements in which different geographically dispersed research groups simultaneously investigate different variants of a new disease.

As one example, the system 8400 and other embodiments disclosed herein can be applied to pharmaceutical industry research and development involving multi-disciplinary approaches to characterizing diseases, infections or contaminations for purposes of developing drugs, vaccines and other types of treatments. These systems and associated distributed data analytics techniques can be applied in numerous other contexts.

Illustrative embodiments can provide a number of other significant advantages relative to conventional arrangements.

For example, some embodiments provide metagenomics-based biological surveillance systems that are faster and more accurate than conventional biological surveillance systems. Moreover, metagenomics-based biological surveillance systems in some embodiments are implemented in a decentralized and privacy-preserving manner. These and other metagenomics-based biological surveillance systems advantageously overcome disadvantages of conventional practice, which as indicated previously often relies primarily on culture-based isolation sequencing and furthermore fails to provide mechanisms for coordinated processing over multiple geographically-distributed sequencing facilities.

Such arrangements are highly useful in providing rapid detection and control of geographically-dispersed waterborne or food-borne diseases, infections or contaminations that may be accelerated due to climate change, as well as in numerous other contexts, such as other contexts relating to public health, vaccine development, clinical diagnosis and treatment of patients, and product safety and compliance. For example, global warming is extending the geographic range of mosquitoes and ticks that harbor and transmit infectious diseases, resulting in outbreaks of malaria, dengue and yellow fever in new locations. In addition, due to its disastrous effect on local agricultural produce as well as weather-induced disasters such as river flooding, climate change is causing mass migration, leading to increased population density, not only of humans, but of disease vectors like rodents and skin parasites that carry pathogenic viruses and bacteria. These factors, along with poor sanitation, malnutrition, lack of access to vaccines, and exposure to contaminated water and food have created a favorable setting for the emergence and transmission of infectious diseases. Metagenomics-based surveillance functionality as disclosed herein advantageously helps to combat these and other emerging issues relating to global warming and climate change.

A metagenomics-based surveillance system in an illustrative embodiment can utilize the data scattered across multiple sequencing centers located worldwide, while preserving data privacy and adjusting for genome plasticity.

The use of WWH nodes in some embodiments leverages one or more frameworks supported by Hadoop YARN, such as MapReduce, Spark, Hive, MPI and numerous others, to support distributed computations while also minimizing data movement, adhering to bandwidth constraints in terms of speed, capacity and cost, and satisfying security policies as well as policies relating to governance, risk management and compliance.

It is to be appreciated that the particular types of system features and functionality as illustrated in the drawings and described above are exemplary only, and numerous other arrangements may be used in other embodiments.

It was noted above that portions of an information processing system as disclosed herein may be implemented using one or more processing platforms. Illustrative embodiments of such platforms will now be described in greater detail. These and other processing platforms may be used to implement at least portions of other information processing systems in other embodiments of the invention. A given such processing platform comprises at least one processing device comprising a processor coupled to a memory.

One illustrative embodiment of a processing platform that may be used to implement at least a portion of an information processing system comprises cloud infrastructure including virtual machines implemented using a hypervisor that runs on physical infrastructure. The cloud infrastructure further comprises sets of applications running on respective ones of the virtual machines under the control of the hypervisor. It is also possible to use multiple hypervisors each providing a set of virtual machines using at least one underlying physical machine. Different sets of virtual machines provided by one or more hypervisors may be utilized in configuring multiple instances of various components of the system.

These and other types of cloud infrastructure can be used to provide what is also referred to herein as a multi-tenant environment. One or more system components such as processing nodes 102 and metagenomics sequencing centers 104, or portions thereof, can be implemented as respective tenants of such a multi-tenant environment.

In some embodiments, the cloud infrastructure additionally or alternatively comprises a plurality of containers implemented using container host devices. For example, a given container of cloud infrastructure illustratively comprises a Docker container or other type of LXC. The containers may be associated with respective tenants of a multi-tenant environment of the system 100, although in other embodiments a given tenant can have multiple containers. The containers may be utilized to implement a variety of different types of functionality within the system 100. For example, containers can be used to implement respective cloud compute nodes or cloud storage nodes of a cloud computing and storage system. The compute nodes or storage nodes may be associated with respective cloud tenants of a multi-tenant environment of system 100. Containers may be used in combination with other virtualization infrastructure such as virtual machines implemented using a hypervisor.

Another illustrative embodiment of a processing platform that may be used to implement at least a portion of an information processing system comprises a plurality of processing devices which communicate with one another over at least one network. The network may comprise any type of network, including by way of example a global computer network such as the Internet, a WAN, a LAN, a satellite network, a telephone or cable network, a cellular network, a wireless network such as a WiFi or WiMAX network, or various portions or combinations of these and other types of networks.

As mentioned previously, some networks utilized in a given embodiment may comprise high-speed local networks in which associated processing devices communicate with one another utilizing PCIe cards of those devices, and networking protocols such as InfiniBand, Gigabit Ethernet or Fibre Channel.

Each processing device of the processing platform comprises a processor coupled to a memory. The processor may comprise a microprocessor, a microcontroller, an application-specific integrated circuit (ASIC), a field-programmable gate array (FPGA) or other type of processing circuitry, as well as portions or combinations of such circuitry elements. The memory may comprise random access memory (RAM), read-only memory (ROM) or other types of memory, in any combination. The memory and other memories disclosed herein should be viewed as illustrative examples of what are more generally referred to as "processor-readable storage media" storing executable program code of one or more software programs.

Articles of manufacture comprising such processor-readable storage media are considered embodiments of the present invention. A given such article of manufacture may comprise, for example, a storage array, a storage disk or an integrated circuit containing RAM, ROM or other electronic memory, or any of a wide variety of other types of computer program products. The term "article of manufacture" as used herein should be understood to exclude transitory, propagating signals.

Also included in the processing device is network interface circuitry, which is used to interface the processing device with the network and other system components, and may comprise conventional transceivers.

Again, these particular processing platforms are presented by way of example only, and other embodiments may include additional or alternative processing platforms, as well as numerous distinct processing platforms in any combination, with each such platform comprising one or more computers, servers, storage devices or other processing devices.

It should therefore be understood that in other embodiments different arrangements of additional or alternative elements may be used. At least a subset of these elements may be collectively implemented on a common processing platform, or each such element may be implemented on a separate processing platform.

Also, numerous other arrangements of computers, servers, storage devices or other components are possible in an information processing system as disclosed herein. Such components can communicate with other elements of the information processing system over any type of network or other communication media.

As indicated previously, components of an information processing system as disclosed herein can be implemented at least in part in the form of one or more software programs stored in memory and executed by a processor of a processing device. For example, at least portions of the functionality of a given metagenomics sequencing center or worldwide data node in a particular embodiment are illustratively implemented in the form of software running on respective processing devices.

It should again be emphasized that the above-described embodiments of the invention are presented for purposes of illustration only. Many variations and other alternative embodiments may be used. For example, the disclosed techniques are applicable to a wide variety of other types of information processing systems, processing and storage platforms, biological surveillance systems, processing nodes, sequencing centers, sample sources and other components. Also, the particular configurations of system and device elements, associated processing operations and other functionality illustrated in the drawings can be varied in other embodiments. Moreover, the various assumptions made above in the course of describing the illustrative embodiments should also be viewed as exemplary rather than as requirements or limitations of the invention. Numerous other alternative embodiments within the scope of the appended claims will be readily apparent to those skilled in the art.

What is claimed is:

1. A method comprising:
obtaining reads of biological samples of respective sample sources wherein each of the biological samples contains genomic material from a plurality of distinct microorganisms within an environment of a corresponding one of the sample sources; and
performing distributed data analytics to characterize an actual or potential outbreak of at least one of a disease, an infection and a contamination that involves genomic material from multiple ones of the distinct microorganisms in one or more of the sample sources;
wherein performing distributed data analytics comprises:
performing local analytics in respective ones of a plurality of data zones; and
performing global analytics utilizing results of the local analytics performed in the respective data zones;
wherein each of the data zones comprises one or more sequencing centers utilized to generate a corresponding subset of the reads within that data zone;
wherein the local analytics performed in a given one of the data zones utilize reads of one or more of the biological samples sequenced in the one or more sequencing centers of the given data zone;
wherein the local analytics performed in the given data zone comprise analyzing the reads of the one or more biological samples against a local set of known gene units;
wherein at least one result of the global analytics comprises a graph in which nodes correspond to respective biological samples and edges between the nodes characterize epidemiological relationships between the biological samples, the edges being weighted by sample-to-sample comparison scores of metagenomics sequencing results for the biological samples; and
wherein the method is implemented by a distributed data processing system comprising a plurality of processing devices configured to communicate with one another over at least one network.

2. The method of claim 1 wherein the local set of known gene units for the given data zone comprises locally-available pre-processed sequenced genomic data collected from reads of the one or more biological samples sequenced in the one or more sequencing centers of the given data zone.

3. The method of claim 2 wherein at least one known gene unit in the local set of known gene units for the given data zone is augmented with metadata comprising one or more of patient symptoms, time and location.

4. The method of claim 1 wherein the reads of the biological samples comprise respective sets of gene units sequenced from those biological samples in corresponding ones of a plurality of sequencing centers.

5. The method of claim 1 wherein the data zones comprise respective geographically-distributed regional data centers each configured to perform local analytics utilizing locally accessible data resources of its corresponding data zone and wherein the results of the local analytics performed in the respective data zones preserve for each of the data zones at least one specified policy of that data zone relating to at least one of privacy, security, governance, risk and compliance.

6. The method of claim 1 wherein at least one additional result of the global analytics comprises global view information characterizing relationships between a first set of reads of a first set of one or more biological samples sequenced in a first set of one or more sequencing centers of a first one of the plurality of data zones and one or more additional sets of reads of one or more additional sets of one or more biological samples sequenced in one or more additional sets of one or more sequencing centers of one or more additional ones of the plurality of data zones.

7. The method of claim 6 wherein the global view information comprises one or more portions of the graph in which the nodes correspond to respective biological samples sequenced by respective ones of the first and one or more additional sets of sequencing centers and the edges between the nodes are weighted by the sample-to-sample comparison scores of the metagenomics sequencing results for the first and one or more additional sets of one or more biological samples.

8. The method of claim 6 wherein the global view information comprises a global epidemiological graph computed utilizing a plurality of local epidemiological graphs provided as results of the local analytics performed in respective ones of the plurality of data zones.

9. The method of claim 6 further comprising utilizing the global view information to at least one of:
predict a spread pattern for the actual or potential outbreak of the at least one disease, infection and contamination; and
identify failures in one or more preventive or sanitary controls.

10. The method of claim 6 wherein performing the global analytics utilizing the results of the local analytics performed in the respective data zones comprises applying a community contact detection algorithm in conjunction with generating the global view information.

11. A method comprising:
obtaining reads of biological samples of respective sample sources wherein each of the biological samples contains genomic material from a plurality of distinct microorganisms within an environment of a corresponding one of the sample sources; and performing distributed data analytics to characterize an actual or potential outbreak of at least one of a disease, an infection and a contamination that involves genomic material from multiple ones of the distinct microorganisms in one or more of the sample sources;

wherein performing distributed data analytics comprises:
performing local analytics in respective ones of a plurality of data zones; and
performing global analytics utilizing results of the local analytics performed in the respective data zones;

wherein each of the data zones comprises one or more sequencing centers utilized to generate a corresponding subset of the reads within that data zone;

wherein the local analytics performed in a given one of the data zones utilize reads of one or more of the biological samples sequenced in the one or more sequencing centers of the given data zone;

wherein the local analytics performed in the given data zone comprise analyzing the reads of the one or more biological samples against a local set of known gene units;

wherein at least one result of the global analytics comprises at least one of a genomic comparison component and an epidemiologic comparison component characterizing relationships between a first set of reads of a first set of one or more biological samples sequenced in a first set of one or more sequencing centers of a first one of the plurality of data zones and one or more additional sets of reads of one or more additional sets of one or more biological samples sequenced in one or more additional sets of one or more sequencing centers of one or more additional ones of the plurality of data zones; and wherein the method is implemented by a distributed data processing system comprising a plurality of processing devices configured to communicate with one another over at least one network.

12. The method of claim 11 wherein the genomic comparison component comprises hit abundance score vectors for respective ones of a plurality of biological samples that are identified as being related to the at least one disease, infection and contamination based at least in part on the first and one or more additional sets of biological samples sequenced in the first and one or more additional sets of one or more sequencing centers, wherein the hit abundance score vector for a given one of the plurality of biological samples comprises a plurality of entries corresponding to respective occurrence frequencies of at least one read of the given biological sample in respective target gene units.

13. The method of claim 11 wherein the epidemiologic comparison component comprises a patient graph in which nodes corresponding to patients are connected in the patient graph based at least in part on patient comparative indexes.

14. The method of claim 11 wherein at least one additional result of the global analytics further comprises a combination of portions of the genomic comparison component with portions of the epidemiologic comparison component that characterizes the actual or potential outbreak of the at least one disease, infection and contamination.

15. The method of claim 11 wherein performing the global analytics further comprises generating an outbreak graph for the at least one disease, infection and contamination utilizing both the genomic comparison component and the epidemiologic comparison component.

16. The method of claim 15 wherein performing the global analytics further comprises applying a community contact detection algorithm as a preprocessing operation prior to generating the outbreak graph.

17. The method of claim 11 wherein performing the global analytics further comprises applying a biclustering operation to a hit abundance score matrix comprising a plurality of hit abundance score vectors based at least in part on epidemiological data associated with different ones of a plurality of patients.

18. The method of claim 11 further comprising utilizing one or more results of the global analytics to associate a particular patient with the at least one disease, infection and contamination based at least in part on statistical decision making utilizing respective portions of the genomic comparison component and the epidemiologic comparison component.

19. A computer program product comprising a non-transitory processor-readable storage medium having stored therein program code of one or more software programs, wherein the program code when executed by a distributed data processing system comprising a plurality of processing devices configured to communicate with one another over at least one network causes said distributed data processing system:

to obtain reads of biological samples of respective sample sources wherein each of the biological samples contains genomic material from a plurality of distinct microorganisms within an environment of a corresponding one of the sample sources; and to perform distributed data analytics to characterize an actual or potential outbreak of at least one of a disease, an infection and a contamination that involves genomic material from multiple ones of the distinct microorganisms in one or more of the sample sources;

wherein performing distributed data analytics comprises:
performing local analytics in respective ones of a plurality of data zones; and
performing global analytics utilizing results of the local analytics performed in the respective data zones;

wherein each of the data zones comprises one or more sequencing centers utilized to generate a corresponding subset of the reads within that data zone;

wherein the local analytics performed in a given one of the data zones utilize reads of one or more of the biological samples sequenced in the one or more sequencing centers of the given data zone;

wherein the local analytics performed in the given data zone comprise analyzing the reads of the one or more biological samples against a local set of known gene units; and wherein at least one result of the global analytics comprises a graph in which nodes correspond to respective biological samples and edges between the nodes characterize epidemiological relationships between the biological samples, the edges being weighted by sample-to-sample comparison scores of metagenomics sequencing results for the biological samples.

20. An apparatus comprising:
a distributed data processing system comprising a plurality of processing devices configured to communicate with one another over at least one network;

wherein said distributed data processing system is configured:
to obtain reads of biological samples of respective sample sources wherein each of the biological samples contains genomic material from a plurality of distinct microorganisms within an environment of a corresponding one of the sample sources; and to perform distributed data analytics to characterize an actual or potential outbreak of at least one of a disease, an infection and a contamination that involves genomic material from multiple ones of the distinct microorganisms in one or more of the sample sources;

wherein performing distributed data analytics comprises:
performing local analytics in respective ones of a plurality of data zones; and
performing global analytics utilizing results of the local analytics performed in the respective data zones;

wherein each of the data zones comprises one or more sequencing centers utilized to generate a corresponding subset of the reads within that data zone;

wherein the local analytics performed in a given one of the data zones utilize reads of one or more of the biological samples sequenced in the one or more sequencing centers of the given data zone;

wherein the local analytics performed in the given data zone comprise analyzing the reads of the one or more biological samples against a local set of known gene units; and wherein at least one result of the global analytics comprises a graph in which nodes correspond to respective biological samples and edges between the nodes characterize epidemiological relationships between the biological samples, the edges being weighted by sample-to-sample comparison scores of metagenomics sequencing results for the biological samples.

\* \* \* \* \*